United States Patent
Araki et al.

(10) Patent No.: US 9,440,933 B2
(45) Date of Patent: Sep. 13, 2016

(54) AZOLE DERIVATIVE, METHOD FOR PRODUCING SAME, INTERMEDIATE COMPOUND, AND AGRICULTURAL OR HORTICULTURAL CHEMICAL AGENT AND INDUSTRIAL MATERIAL PROTECTING AGENT

(71) Applicant: KUREHA CORPORATION, Tokyo (JP)

(72) Inventors: Nobuyuki Araki, Tokyo (JP); Taiji Miyake, Tokyo (JP); Eiyu Imai, Tokyo (JP); Emiko Obata, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 0 days.

(21) Appl. No.: 14/691,279

(22) Filed: Apr. 20, 2015

(65) Prior Publication Data

US 2015/0299144 A1 Oct. 22, 2015

Related U.S. Application Data

(62) Division of application No. 14/124,546, filed as application No. PCT/JP2012/064534 on Jun. 6, 2012, now Pat. No. 9,035,069.

(30) Foreign Application Priority Data

Jun. 7, 2011 (JP) .................................. 2011-127759

(51) Int. Cl.
| | |
|---|---|
| *C07D 249/08* | (2006.01) |
| *C07D 249/12* | (2006.01) |
| *C07D 233/56* | (2006.01) |
| *A01N 43/653* | (2006.01) |
| *C07D 233/60* | (2006.01) |
| *C07D 405/06* | (2006.01) |
| *A01N 43/50* | (2006.01) |
| *A01N 43/80* | (2006.01) |
| *C07D 405/04* | (2006.01) |

(52) U.S. Cl.
CPC ............ *C07D 249/12* (2013.01); *A01N 43/50* (2013.01); *A01N 43/653* (2013.01); *A01N 43/80* (2013.01); *C07D 233/56* (2013.01); *C07D 233/60* (2013.01); *C07D 249/08* (2013.01); *C07D 405/04* (2013.01); *C07D 405/06* (2013.01)

(58) Field of Classification Search
CPC ................................................... C07D 249/08
See application file for complete search history.

(56) References Cited

U.S. PATENT DOCUMENTS 4,503,063 A 3/1985 Richardson et al.
4,547,214 A 10/1985 Crowley et al.
4,904,682 A 2/1990 Kramer et al.
4,938,792 A 7/1990 Kumazawa et al.
5,028,254 A 7/1991 Kumazawa et al.

(Continued)

FOREIGN PATENT DOCUMENTS

CN 1044814 A 8/1990
CN 103562187 A 2/2014

(Continued)

OTHER PUBLICATIONS

Extended European Search Report for European Application No. 12797440.0 dated Nov. 19, 2014.
U.S. Appl. No. 14/359,449, filed May 20, 2014.
International Search Report, issued in PCT/JP2012/064534, dated Jul. 31, 2012.
Japanese Reasons for Refusal for Application No. 2013-545903, dated Nov. 17, 2015 with English language translation.
Chinese Office Action and Search Report dated Jan. 23, 2015, for Chinese Application No. 201280056290.0 with the English translation.
English translation of International Preliminary Report on Patentability and Written Opinion issued Jun. 19, 2014, in PCT International Application No. PCT/JP2012/079778.

(Continued)

*Primary Examiner* — Michael Barker
*Assistant Examiner* — Karen Cheng
(74) *Attorney, Agent, or Firm* — Birch, Stewart, Kolasch & Birch, LLP

(57) ABSTRACT

Provided is an azole derivative superior in disease-controlling activity contained as an active ingredient in agricultural or horticultural chemical agents.
The azole derivative according to the present invention is represented by the following General Formula (I):

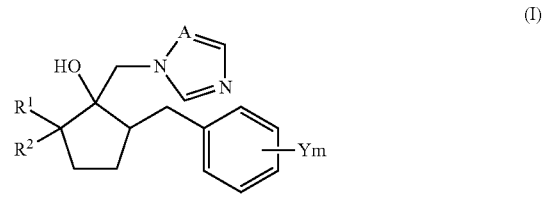

(in Formula (I), $R^1$ represents an unsubstituted or substituted $C_1$-$C_6$-alkyl group;
$R^2$ represents a carbonyl group-containing functional group, wherein the carbon atom in the carbonyl group is bound to the carbon atom in the cyclopentane ring substituted with $R^1$ and to a hydrogen atom, a hydroxyl group, $R^3$, $OR^3$, or $NR^3R^4$;
$R^3$ and $R^4$ each represent a $C_1$-$C_6$-alkyl group, a $C_2$-$C_6$-alkenyl group, or a $C_2$-$C_6$-alkynyl group;
Y represents a halogen atom, a $C_1$-$C_4$-alkyl group, a $C_1$-$C_4$-haloalkyl group, a $C_1$-$C_4$-alkoxy group, a $C_1$-$C_4$-haloalkoxy group, a phenyl group, a cyano group, or a nitro group;
m is 0 to 5; and
A represents a nitrogen atom or a methine group).

1 Claim, 1 Drawing Sheet

(56) References Cited

U.S. PATENT DOCUMENTS

| | | | |
|---|---|---|---|
| 5,047,548 | A | 9/1991 | Richardson et al. |
| 5,159,118 | A | 10/1992 | Kumazawa et al. |
| 5,239,089 | A | 8/1993 | Kumazawa et al. |
| 5,256,683 | A | 10/1993 | Hutt et al. |
| 5,292,764 | A | 3/1994 | Arahira et al. |
| 5,380,743 | A | 1/1995 | Hutt et al. |
| 5,414,105 | A | 5/1995 | Kumazawa et al. |
| 5,639,918 | A | 6/1997 | Hutt et al. |
| 2011/0124877 | A1 | 5/2011 | Ito et al. |
| 2014/0179517 | A1 | 6/2014 | Araki et al. |

FOREIGN PATENT DOCUMENTS

| | | |
|---|---|---|
| DE | 39 02 031 A1 | 7/1990 |
| DE | 4320498 A1 | 12/1994 |
| EP | 0 046 633 A1 | 3/1982 |
| EP | 0 086 917 A1 | 8/1983 |
| EP | 0 106 515 A2 | 4/1984 |
| EP | 0 267 778 A2 | 5/1988 |
| EP | 0 313 983 A2 | 5/1989 |
| EP | 0341954 A1 | 11/1989 |
| EP | 0 488 348 A1 | 6/1992 |
| EP | 0 329 367 B1 | 10/1993 |
| IL | 85428 A | 12/1992 |
| JP | 58-134079 A | 8/1983 |
| JP | 59-82376 A | 5/1984 |
| JP | 1-93574 A | 4/1989 |
| JP | 01149776 A | 6/1989 |
| JP | 1-186871 A | 7/1989 |
| JP | 1-301664 A | 12/1989 |
| JP | 2-42003 A | 2/1990 |
| JP | 04202190 A | 7/1992 |
| JP | 5-271197 A | 10/1993 |
| WO | WO 2009/088070 A1 | 7/2009 |
| WO | WO 2010/023862 A1 | 3/2010 |
| WO | WO 2010/074021 A1 | 7/2010 |
| WO | WO 2011/070771 A1 | 6/2011 |

OTHER PUBLICATIONS

Extended European Search Report issued Jun. 17, 2015, in European Patent Application No. 12851782.8.

Second Office Action issued Jul. 16, 2015, in Chinese Patent Application No. 201280056290.0, with English translation.

International Search Report of PCT/JP2012/079778 dated Dec. 11, 2012.

U.S. Office Action for U.S. Appl. No. 14/359,449 dated Sep. 8, 2015.

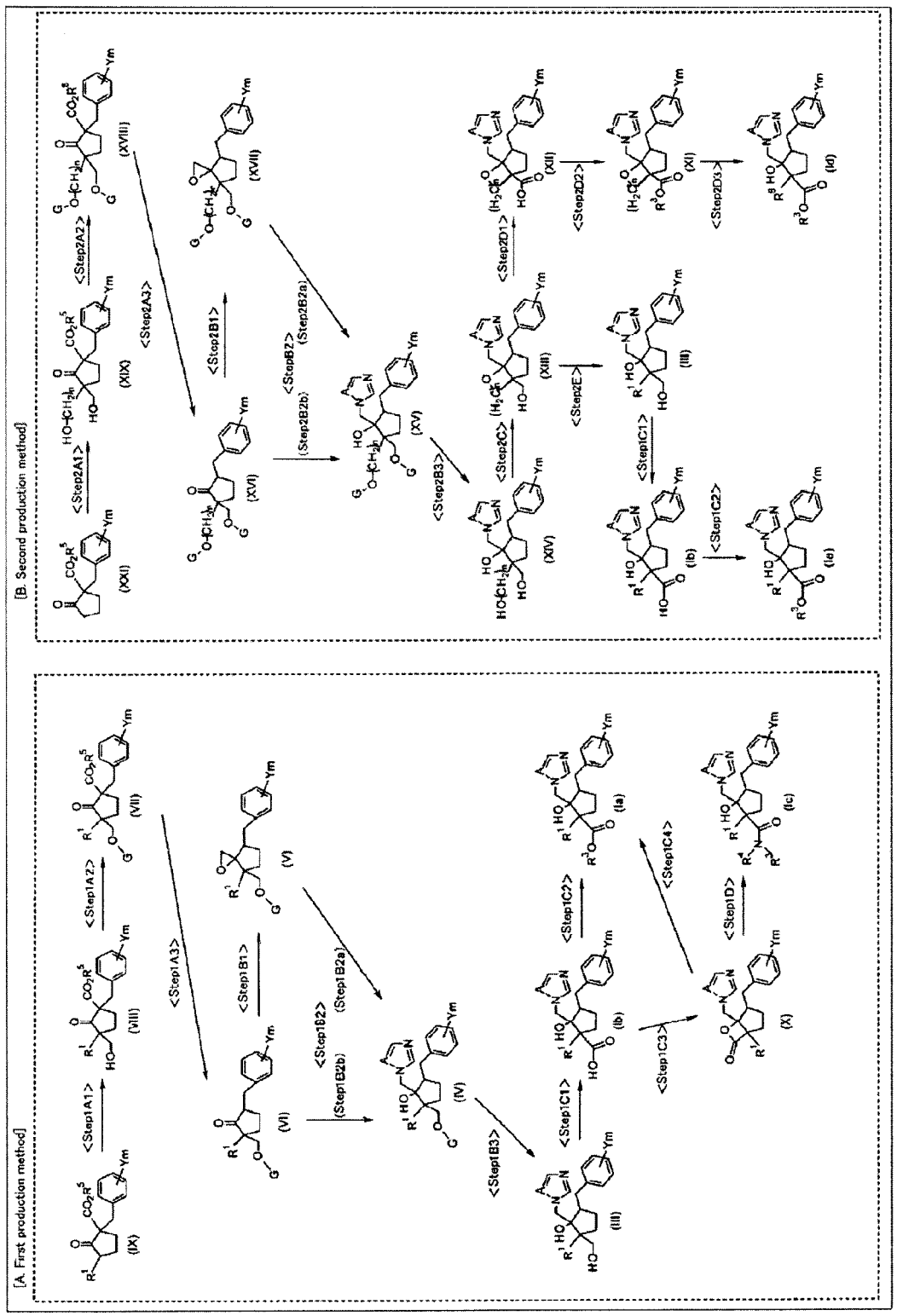

AZOLE DERIVATIVE, METHOD FOR PRODUCING SAME, INTERMEDIATE COMPOUND, AND AGRICULTURAL OR HORTICULTURAL CHEMICAL AGENT AND INDUSTRIAL MATERIAL PROTECTING AGENT

CROSS REFERENCE TO RELATED APPLICATIONS

This application is a Divisional application of co-pending U.S. application Ser. No. 14/124,546 filed on Jan. 8, 2014, which is the National Phase of PCT/JP2012/064534 filed on Jun. 6, 2012, which claims priority under 35 U.S.C 119(a) to Patent Application No. 2011-127759 filed in Japan on Jun. 7, 2011, all of which are hereby expressly incorporated by reference into the present application.

TECHNICAL FIELD

The present invention relates to a new azole derivative. It also relates to an agricultural or horticultural chemical agent and an industrial material-protecting agent containing the derivative as an active ingredient, and a method for producing the derivative. It also relates to an intermediate compound thereof.

BACKGROUND ART

Some kinds of 2-substituted-5-benzyl-1-azolylmethylcyclopentanol derivatives are known to have sterilizing activity (see, for example, Patent Documents 1 and 2).

In addition, some compounds included in 2-(halogenated hydrocarbon-substituted)-5-benzyl-1-azolylmethylcyclopentanol derivatives are reported to show anti-seizure or anxiolytic activity (see Patent Document 3). There is no description on agricultural or horticultural chemical agents and industrial material-protecting agents and the compounds included in the scope of the present invention are not disclosed specifically in Patent Document 3.

CITATION LIST

Patent Literature

[PTL 1] Japanese Unexamined Application Publication No. 1-93574
[PTL 2] Japanese Unexamined Application Publication No. 1-186871
[PTL 3] Germany Patent Application Publication No. 3902031
[PTL 4] Japanese Unexamined Application Publication No. 05-271197
[PTL 5] Japanese Unexamined Application Publication No. 01-301664

SUMMARY OF INVENTION

Technical Problem

There has been a demand for an agricultural or horticultural disease-controlling agent that is less toxic to human and animals and superior in handling stability, and shows high controlling activity to a wide variety of plant diseases. There are also demands for a plant growth-regulating agent regulating growth of various farm crops and horticultural plants and thus increasing the yield and improving the quality thereof and also for an industrial material-protecting agent protecting industrial materials from various hazardous microorganisms that erode the materials.

Objects of the present invention are to provide an azole derivative that meets the demands above, a production method thereof, an intermediate compound thereof, and an agricultural or horticultural chemical agent and an industrial material-protecting agent containing the same.

Solution to Problem

To achieve the objects above, the inventors have studied the chemical structure and the physiological activity of many azole derivatives. As a result, they have found that an azole derivative represented by the following General Formula (I) shows favorable activity and made the present invention. The present invention that was made based on the new findings contains the following inventions:

The azole derivative according to the present invention is characterized by having a structure represented by the following General Formula (I):

[C.1]

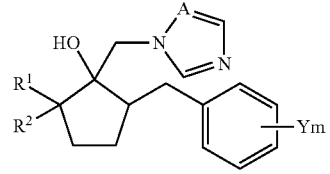

(I)

(in Formula (I), $R^1$ represents an unsubstituted or substituted $C_1$-$C_6$-alkyl group;
$R^2$ represents a carbonyl group-containing functional group, wherein the carbon atom in the carbonyl group is bound to the carbon atom in the cyclopentane ring substituted with $R^1$ and to $R^3$, $OR^3$, or $NR^3R^4$;
$R^3$ and $R^4$ each represent a hydrogen atom, a $C_1$-$C_6$-alkyl group, a $C_2$-$C_6$-alkenyl group, or a $C_2$-$C_6$-alkynyl group;
Y represents a halogen atom, a $C_1$-$C_4$-alkyl group, a $C_1$-$C_4$-haloalkyl group, a $C_1$-$C_4$-alkoxy group, a $C_1$-$C_4$-haloalkoxy group, a phenyl group, a cyano group, or a nitro group;
m is 0 to 5; and
A represents a nitrogen atom or a methine group.)

The azole derivative according to the present invention in the configuration above has a favorable effect of showing favorable sterilizing activity to many plant disease-causing microbes.

Preferably in the azole derivative according to the present invention of General Formula (I) above, $R^2$ is $COOR^3$, and $R^3$ is a $C_1$-$C_3$-alkyl group, a $C_2$-$C_3$-alkenyl group or a $C_2$-$C_3$-alkynyl group.

Also preferably in the azole derivative according to the present invention of General Formula (I) above, $R^2$ is $CONR^3R^4$, and $R^3$ and $R^4$ each are independently a hydrogen atom, a $C_1$-$C_3$-alkyl group, a $C_2$-$C_3$-alkenyl group, or a $C_2$-$C_3$-alkynyl group.

Also preferably in the azole derivative according to the present invention of General Formula (I) above, $R^1$ is a halogen atom-substituted $C_1$-$C_6$-alkyl group.

Also preferably in the azole derivative according to the present invention of General Formula (I) above, $R^1$ is an unsubstituted alkyl group.

Also in the azole derivative according to the present invention of General Formula (I) above, the number of carbons in $R^1$ is preferably 1 to 4.

Preferably in General Formula (I) above, Y is a halogen atom and m is 1.

The method for producing the azole derivative according to the present invention, wherein $R^2$ is $COOR^3$, is characterized by comprising an esterification step of esterifying the carboxyl group contained in the carboxylic acid compound represented by the following General Formula (Ib). Thus, the esterification step is a step of converting the carboxyl group contained in a carboxylic acid compound to $COOR^3$. As $R^2$ is a carboxyl group when $R^3$ is a hydrogen atom, $R^3$ here is not a hydrogen atom.

[C.2]

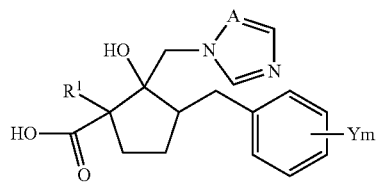

(Ib)

(in Formula (Ib), $R^1$, Y, m, and A are the same as $R^1$, Y, m, and A in Formula (I) and $R^3$ represents a $C_1$-$C_6$-alkyl group, a $C_2$-$C_6$-alkenyl group, or a $C_2$-$C_6$-alkynyl group).

The method for producing the azole derivative described above preferably comprises an oxidation step of preparing the carboxylic acid compound by oxidizing the hydroxymethyl group contained in the intermediate compound represented by the following General Formula (III).

[C.3]

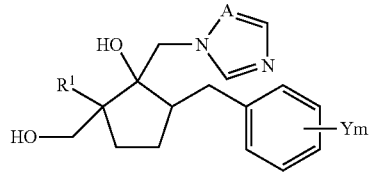

(III)

(in Formula (III), $R^1$, Y, m, and A are the same as $R^1$, Y, m, and A in Formula (Ib).)

The method of producing the azole derivative according to the present invention, wherein $R^2$ is $COOR^3$ is characterized by comprising an esterification step of esterifying the carboxyl group contained in a carboxylic acid compound represented by the following General Formula (XII) and a ring-opening step of opening the ring of the ester compound represented by the following General Formula (XI) obtained in the esterification step with a halogen acid. Thus, the esterification step is a step of converting the carboxyl group contained in the carboxylic acid compound to $COOR^3$. As $R^2$ is a carboxyl group when $R^3$ is hydrogen atom, $R^3$ here is not a hydrogen atom.

[C.4]

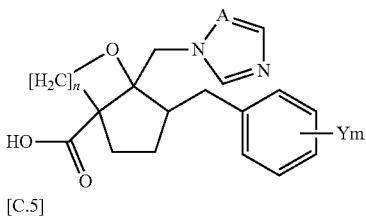

(XII)

[C.5]

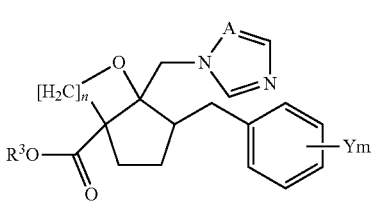

(XI)

(in Formulae (XI) and (XII), $R^3$, Y, m, and A are the same as $R^1$, Y, m, and A in Formula (I). n is 1 to 6. In Formula (XI), $R^3$ represents a $C_1$-$C_6$-alkyl group, a $C_2$-$C_6$-alkenyl group, or a $C_2$-$C_6$-alkynyl group.)

The method for producing an azole derivative described above preferably comprises an oxidation step of preparing the carboxylic acid compound represented by the following General Formula (XII) by oxidizing the hydroxymethyl group contained the intermediate compound represented by the following General Formula (XIII).

[C.6]

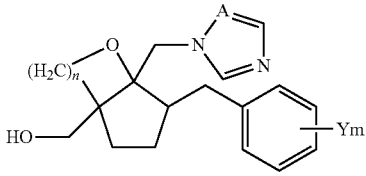

(XIII)

(in Formula (XIII), Y, m, n, and A are the same as Y, m, n, and A in Formula (XII).)

The method for producing the azole derivative according to the present invention, wherein $R^2$ is $COOR^3$, is characterized by comprising a ring-opening step of opening the ring of the lactone compound represented by the following General Formula (X) with a metal alcoholate represented by $R^3O^-Ma^+$.

[C. 7]

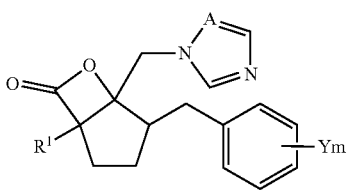

(X)

(in Formula (X), $R^1$, Y, m, and A are the same as $R^1$, Y, m, and A in Formula (I) and $R^3$ represents a $C_1$-$C_6$-alkyl group, a $C_2$-$C_6$-alkenyl group, or a $C_2$-$C_6$-alkynyl group and Ma represents an alkali metal).

The method for producing the azole derivative according to the present invention, wherein $R^2$ is $CONR^3R^4$, is characterized by comprising a ring-opening step of opening the ring of the lactone compound represented by the following General Formula (X) with an amine compound represented by $NHR^3R^4$.

[C. 8]

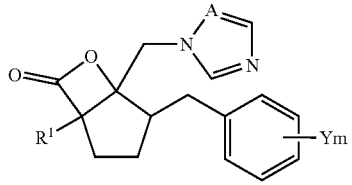
(X)

(in Formula (X), $R^1$, Y, m, and A are the same as $R^1$, Y, m, and A in Formula (I). $R^3$ and $R^4$ each represent a hydrogen atom, a $C_1$-$C_6$-alkyl group, a $C_2$-$C_6$-alkenyl group, or a $C_2$-$C_6$-alkynyl group.)

The method for producing an azole derivative described above preferably comprises a condensation step of preparing the compound represented by the General Formula (X) above by condensing the carboxylic acid compound represented by the following General Formula (Ib) with a condensing agent.

[C. 9]

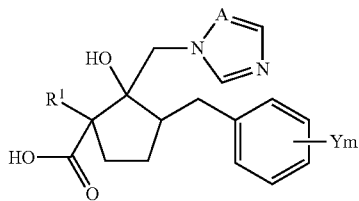
(Ib)

(in Formula (Ib), $R^1$, Y, m, and A are the same as $R^1$, Y, m, and A in Formula (X).)

In addition, the intermediate compound represented by the following General Formula (Ib) is also included in the scope of the present invention.

[C. 10]

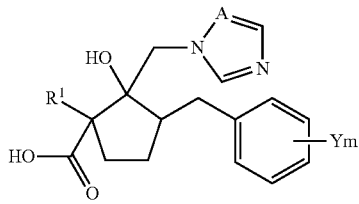
(Ib)

(in Formula (Ib), $R^1$, Y, m, and A are the same as $R^1$, Y, m, and A in Formula (I).)

In addition, the intermediate compound represented by the following General Formula (X) is also included in the scope of the present invention.

[C. 11]

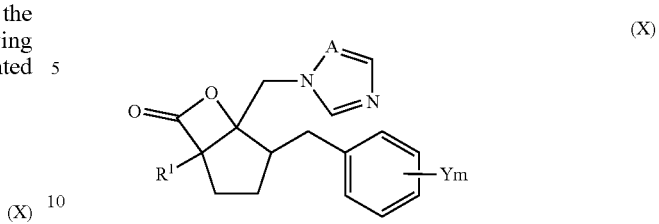
(X)

(in Formula (X), $R^1$, Y, m, and A are the same as $R^1$, Y, m, and A in Formula (I).)

In addition, the intermediate compound represented by the following General Formula (XI) for production of the azole derivative according to the present invention, wherein $R^2$ is $COOR^3$ and $R^1$ is a halogen atom-substituted $C_1$-$C_6$-alkyl group, is also included in the scope of the present invention.

[C. 12]

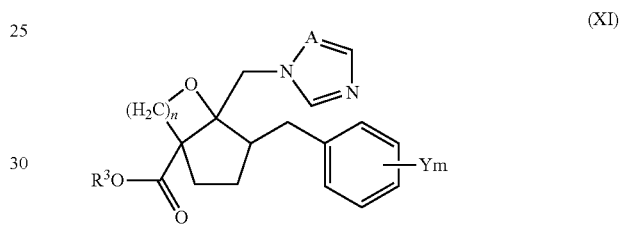
(XI)

(in Formula (XI), Y, m, and A are the same as Y, m, and A in Formula (I); $R^3$ represents a hydrogen atom, a $C_1$-$C_6$-alkyl group, a $C_2$-$C_6$-alkenyl group, or a $C_2$-$C_6$-alkynyl group; and n is 1 to 6.)

Agricultural or horticultural chemical agents or industrial material-protecting agents containing the azole derivative according to the present invention as an active ingredient are also included in the scope of the present invention. The agricultural or horticultural chemical agent can be used for seed treatment. In addition, the seeds treated with the agricultural or horticultural chemical agent are also included in the scope of the present invention.

Unless specified otherwise, the same codes are allocated respectively to the same functional groups (or atoms) in respective General Formulae in the present description and others and detailed description thereof is eliminated. For example, $R^1$ in General Formula (I) is identical with $R^1$ in another General Formula, unless specified otherwise. The same applies to other functional groups (or atoms), in addition to $R^1$.

Advantageous Effects of Invention

The azole derivative according to the present invention shows favorable sterilizing activity to many plant disease-causing microbes. Thus, agricultural or horticultural chemical agents containing the azole derivative according to the present invention as an active ingredient have an favorable effect of showing high controlling activity to a wide variety of plant diseases.

The agricultural or horticultural chemical agents containing the azole derivative according to the present invention as an active ingredient also have an favorable effect of regulating growth of various farm crops and horticultural plants, thus increasing the yield and improving the quality thereof.

The industrial material-protecting agents containing the azole derivative according to the present invention as an active ingredient have additionally a favorable effect of protecting industrial materials from a variety of hazardous microorganisms eroding them further effectively.

BRIEF DESCRIPTION OF DRAWINGS

FIG. 1 is a chart briefly showing first and second production methods for the compound (I) according to the present invention.

BRIEF DESCRIPTION OF DRAWINGS

Hereinafter, favorable embodiments of the present invention will be described. The embodiments below are some of the typical embodiments of the present invention and it should be understood that the scope of the present invention is not restricted thereby.

1. Azole Derivative

The azole derivative according to the present invention represented by the following General Formula (I) (hereinafter, referred to as compound (I)) will be described. The compound (I) has a substituted or unsubstituted alkyl group and a carbonyl group-containing functional group on the 2-position of the cyclopentane ring.

[C. 13]

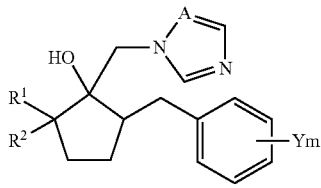

(I)

(1) $R^1$

First, the substituted or unsubstituted alkyl group ($R^1$) bound to the 2-position of the cyclopentane ring will be described. Examples of $R^1$ include $C_1$-$C_6$-alkyl groups and $C_1$-$C_6$-haloalkyl groups.

The $C_1$-$C_6$-alkyl group is not particularly limited, if it is an alkyl group having 1 to 6 carbon atoms, but preferably a $C_1$-$C_4$-alkyl group. Typical examples thereof include methyl group, ethyl group, (1-methyl)ethyl group, n-propyl group, 1-methylpropyl group, 2-methylpropyl group, n-butyl group, 1-methylbutyl group, 2-methylbutyl group, 1-ethylpropyl group, 1,1-dimethylethyl group, and the like. When $R^1$ is a $C_1$-$C_6$-alkyl group, the compound (I) is a 2-acyl-2-alkyl-5-benzyl-1-azolylmethylcyclopentanol derivative.

The $C_1$-$C_6$-haloalkyl group is not particularly limited, if it is a haloalkyl group having 1 to 6 carbon atoms, but preferably a $C_1$-$C_4$-haloalkyl group. Typical examples thereof are halogen-substituted $C_1$-$C_6$-alkyl groups such as chloromethyl group, dichloromethyl group, trichloromethyl group, 2-chloroethyl group, 1-chloroethyl group, 2,2-dichloroethyl group, 1,2-dichloroethyl group, 2,2,2-trichloroethyl group, 3-chloropropyl group, 2,3-dichloropropyl group, 1-chloro-1-methylethyl group, 2-chloro-1-methylethyl group, 2-chloropropyl group, 4-chlorobutyl group, 5-chloropentyl group, fluoromethyl group, difluoromethyl group, trifluoromethyl group, 2-fluoroethyl group, 1-fluoroethyl group, 2,2-difluoroethyl group, 1,2-difluoroethyl group, 2,2,2-trifluoroethyl group, 3-fluoropropyl group, 2,3-difluoropropyl group, 1-fluoro-1-methylethyl group, 2-fluoro-1-methylethyl group, 2-fluoropropyl group, 3,3,3-trifluoropropyl group, 2,2,3,3-tetrafluoropropyl group, 2,2,3,3,3-pentafluoropropyl group, 4-fluorobutyl group, 5-fluoropentyl group, bromomethyl group, dibromomethyl group, tribromomethyl group, 2-bromoethyl group, 1-bromoethyl group, 2,2-dibromoethyl group, 1,2-dibromoethyl group, 2,2,2-tribromoethyl group, 3-bromopropyl group, 2,3-dibromopropyl group, 1-bromo-1-methylethyl group, 2-bromo-1-methylethyl group, 2-bromopropyl group, 4-bromobutyl group, 5-bromopentyl group, iodomethyl group, diiodomethyl group, 2-iodoethyl group, 1-iodoethyl group, 2,2-diiodoethyl group, 1,2-diiodoethyl group, 2,2,2-triiodoethyl group, 3-iodopropyl group, 2,3-diiodopropyl group, 1-iodo-1-methylethyl group, 2-iodo-1-methylethyl group, 2-iodopropyl group, 4-iodobutyl group, and the like. When $R^1$ is a $C_1$-$C_6$-haloalkyl group, the compound (I) is a 2-acyl-2-haloalkyl-5-benzyl-1-azolylmethylcyclopentanol derivative.

(2) $R^2$

Hereinafter, the carbonyl group-containing functional group ($R^2$) bound to the 2-position of the cyclopentane ring will be described. The carbon atom of the carbonyl group in $R^2$ is bound to the carbon atom in the cyclopentane ring substituted with $R^1$ and also to $R^3$, $OR^3$, or $NR^3R^4$. Thus, the carbon atom of the carbonyl group in $R^2$ is bound to the carbon atom substituted with $R^1$. Accordingly, the carbonyl group in $R^2$ is located at the position closest to the cyclopentane ring in the functional group represented by $R^2$.

Examples of $R^3$ and $R^4$ include a hydrogen atom, $C_1$-$C_6$-alkyl groups, $C_2$-$C_6$-alkenyl groups, $C_2$-$C_6$-alkynyl groups, unsubstituted and substituted benzyl groups, unsubstituted and substituted phenethyl groups, unsubstituted and substituted phenyl groups, and the like. When the carbon atom of the carbonyl group in $R^2$ is bound to $NR^3R^4$, $R^3$ and $R^4$ may be the same as or different from each other.

Typical examples of the groups when the carbon atom of the carbonyl group in $R^2$ is bound to $R^3$, $OR^3$, or $NR^3R^4$ are shown below:

When the carbon atom of the carbonyl group in $R^2$ is bound to a hydrogen atom (when $R^3$ is a hydrogen atom), $R^2$ is a formyl group ($R^2$=—CHO).

When the carbon atom of the carbonyl group in $R^2$ is bound to $OR^3$ and $R^3$ is a hydrogen atom, $R^2$ is a carboxyl group ($R^2$=—COOH).

When the carbon atom of the carbonyl group in $R^2$ is bound to $R^3$ and $R^3$ is not a hydrogen atom, $R^2$ is, for example, acetyl group, propionyl group, butyryl group, isobutyryl group, pentanoyl group, hexanoyl group, heptanoyl group, or the like.

When the carbon atom of the carbonyl group in $R^2$ is bound to $OR^3$ and $R^3$ is not a hydrogen atom, $R^2$ is, for example, methoxycarbonyl group, ethoxycarbonyl group, propoxycarbonyl group, butoxycarbonyl group, pentoxycarbonyl group, hexanoxycarbonyl group, or the like.

When the carbon atom of the carbonyl group in $R^2$ is bound to $NR^3R^4$, $R^2$ is, for example, dimethylamido group, ethylmethylamido group, methylpropylamido group, butylmethylamido group, methylpentylamido group, hexylmethylamido group, diethylamido group, ethylpropylamido group, butylethylamido group, ethylpentylamido group, ethylhexylamido group, dipropylamido group, butylpropylamido group, pentylpropylamido group, hexylpropylamido group, dibutylamido group, butylpentylamido group, butylhexylamido group, dipropylamido group, hexylpropylamido group, dihexylamido group, methylamido group, ethylamido group, propylamido group, butylamido group, pentylamido group, hexylamido group, or the like.

(3) Y.m

Examples of Y include the following substituent groups:

Halogen atoms, such as chlorine atom, fluorine atom, bromine atom, iodine atom, and the like.

$C_1$-$C_4$-alkyl groups, such as methyl group, ethyl group, n-propyl group, 1-methylethyl group, 2-methylpropyl group, n-butyl group, 1,1-dimethylethyl group, and the like.

$C_1$-$C_4$-haloalkyl groups, such as trifluoromethyl group, 1,1,2,2,2-pentafluoroethyl group, chloromethyl group, trichloromethyl group, bromomethyl group, and the like.

$C_1$-$C_4$-alkoxy groups, such as methoxy group, ethoxy group, n-propoxy group, and the like.

$C_1$-$C_4$-haloalkoxy groups, such as trifluoromethoxy group, difluoromethoxy group, 1,1,2,2,2-pentafluoroethoxy group, 2,2,2-trifluoroethoxy group, and the like.

Y may be a phenyl group, a cyano group, or a nitro group.

Y is preferably a halogen atom, a $C_1$-$C_3$-haloalkyl group, a $C_1$-$C_3$-haloalkoxy group, a $C_1$-$C_3$-alkyl group, or a $C_1$-$C_3$-alkoxy group, particularly preferably a halogen atom, a $C_1$-$C_2$-haloalkyl group, or a $C_1$-$C_2$-haloalkoxy group.

m is an integer of 0 to 5. When m is 2 or more, Y may be the same as or different from each other. Here, m is preferably 0 to 3, more preferably 0 to 2. In particular, m is more preferably 1.

(4) A

A is, for example, a nitrogen atom or a methine group. More preferably, A is a nitrogen atom.

(5) Stereoisomers

The compound (I) has stereoisomers represented by the following General Formulae (CC), (TT), (CT), and (TC). The compound (I) may be an isomer or a mixture of isomers. In the following General Formulae, the relative configuration in which 1-hydroxyl group and 2-alkyl group ($R^1$) are cis-oriented and 1-hydroxyl group and 5-benzyl group are cis-oriented is indicated by (CC). Alternatively, the relative configuration in which 1-hydroxyl group and 2-alkyl group ($R^1$) are trans-oriented and 1-hydroxyl group and 5-benzyl group are trans-oriented is indicated by (TT). Alternatively, the relative configuration in which 1-hydroxyl group and 2-alkyl group ($R^1$) are cis-oriented and 1-hydroxyl group and 5-benzyl group are trans-oriented is indicated by (CT). Yet alternatively, the relative configuration in which 1-hydroxyl group and 2-alkyl group ($R^1$) are trans-oriented and 1-hydroxyl group and 5-benzyl group are cis-oriented is indicated by (TC). In the present description or others, the carbon bound to a hydroxyl group is the 1-position of the cyclopentane ring.

[C. 14]

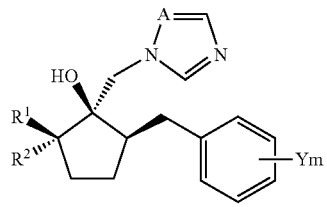

CC

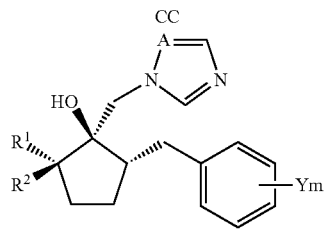

TT

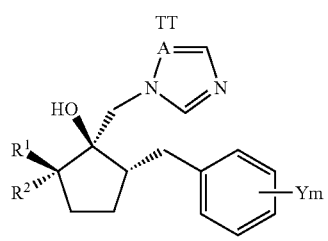

CT

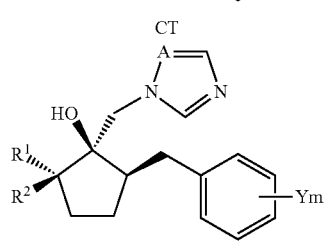

TC (6) Typical Examples

Typical examples of the compound (I), which are different in $R^1$, $R^2$, Ym, A, and isomer type described above, include the following compounds shown in Tables 1 to 12.

In the Tables below:

1) Column of $R^1$ $R^1$ is shown as a substituent group. Each substituent group shown in the table binds to the cyclopentane ring of compound (I) with the carbon atom at the left end of $R^1$ where a hydrogen atom is deficient.

2) Column of $R^2$ $R^2$ is shown as a substituent group. Each substituent group shown in the table binds to the cyclopentane ring of compound (I) with the carbon atom bound to the oxygen atom of $R^2$.

3) Column of Ym

"-" indicates that the compound is unsubstituted (m=0). The number before "-" (hyphen) indicates the binding site of the substituent on the phenyl ring, when the phenyl ring has a substituent, relative to the position (1-position) bound to the carbon atom bound to the cyclopentane ring.

TABLE 1

| Compound number | $R^1$ | $R^2$ | Ym | A | Type |
|---|---|---|---|---|---|
| I-1 | $CH_3$ | COOH | 4-Cl | N | CC |
| I-2 | $CH_3$ | $COOCH_3$ | 4-Cl | N | CC |
| I-3 | $CH_3$ | $COOCH_2CH_3$ | 4-Cl | N | CC |
| I-4 | $CH_3$ | $COOCH_2CH=CH_2$ | 4-Cl | N | CC |
| I-5 | $CH_3$ | $COOCH_2C\equiv CH$ | 4-Cl | N | CC |
| I-6 | $CH_3$ | $COOCH_2CH_2CH_3$ | 4-Cl | N | CC |
| I-7 | $CH_3$ | $COOCH(CH_3)_2$ | 4-Cl | N | CC |
| I-8 | $CH_3$ | $COOCH_2CH_2CH_2CH_3$ | 4-Cl | N | CC |
| I-9 | $CH_3$ | $COOCH_2CH(CH_3)CH_3$ | 4-Cl | N | CC |
| I-10 | $CH_3$ | $COOCH(CH_3)CH_2CH_3$ | 4-Cl | N | CC |
| I-11 | $CH_3$ | $COOC(CH_3)_3$ | 4-Cl | N | CC |
| I-12 | $CH_3$ | $COOCH_2CH_2CH_2CH_2CH_3$ | 4-Cl | N | CC |
| I-13 | $CH_3$ | $COOCH(CH_3)_2CH_2CH_3$ | 4-Cl | N | CC |
| I-14 | $CH_3$ | $COOCH_2C(CH_3)_3$ | 4-Cl | N | CC |
| I-15 | $CH_3$ | $COOCH_2CH=CH(CH_3)$ | 4-Cl | N | CC |
| I-16 | $CH_3$ | $COOCH_2C(CH_3)=CH_2$ | 4-Cl | N | CC |
| I-17 | $CH_3$ | $COOCH_2C\equiv CCH_3$ | 4-Cl | N | CC |
| I-18 | $CH_3$ | $CONHCH_3$ | 4-Cl | N | CC |
| I-19 | $CH_3$ | $CONHCH_2CH_3$ | 4-Cl | N | CC |
| I-20 | $CH_3$ | $CONHCH_2CH_2CH_3$ | 4-Cl | N | CC |
| I-21 | $CH_3$ | $CONHCH(CH_3)_2$ | 4-Cl | N | CC |
| I-22 | $CH_3$ | $CONHCH_2CH=CH_2$ | 4-Cl | N | CC |
| I-23 | $CH_3$ | $CONHCH_2C\equiv CH$ | 4-Cl | N | CC |
| I-24 | $CH_3$ | $CON(CH_3)_2$ | 4-Cl | N | CC |
| I-25 | $CH_3$ | $CON(CH_2CH_3)_2$ | 4-Cl | N | CC |
| I-26 | $CH_3$ | $CON(CH_3)CH_2CH_3$ | 4-Cl | N | CC |
| I-27 | $CH_3$ | CHO | 4-Cl | N | CC |
| I-28 | $CH_3$ | $COCH_3$ | 4-Cl | N | CC |
| I-29 | $C_2H_5$ | COOH | 4-Cl | N | CC |
| I-30 | $C_2H_5$ | $COOCH_3$ | 4-Cl | N | CC |
| I-31 | $C_2H_5$ | $COOCH_2CH_3$ | 4-Cl | N | CC |
| I-32 | $C_2H_5$ | $COOCH_2CH=CH_2$ | 4-Cl | N | CC |
| I-33 | $C_2H_5$ | $COOCH_2C\equiv CH$ | 4-Cl | N | CC |
| I-34 | $C_2H_5$ | $COOCH_2CH_2CH_3$ | 4-Cl | N | CC |
| I-35 | $C_2H_5$ | $COOCH(CH_3)_2$ | 4-Cl | N | CC |
| I-36 | $C_2H_5$ | $CONHCH_3$ | 4-Cl | N | CC |
| I-37 | $C_3H_7$ | COOH | 4-Cl | N | CC |
| I-38 | $C_3H_7$ | $COOCH_3$ | 4-Cl | N | CC |
| I-39 | $C_3H_7$ | $COOCH_2CH_3$ | 4-Cl | N | CC |
| I-40 | $C_3H_7$ | $COOCH_2CH=CH_2$ | 4-Cl | N | CC |
| I-41 | $C_3H_7$ | $COOCH_2C\equiv CH$ | 4-Cl | N | CC |
| I-42 | $C_3H_7$ | $COOCH_2CH_2CH_3$ | 4-Cl | N | CC |
| I-43 | $C_3H_7$ | $COOCH(CH_3)_2$ | 4-Cl | N | CC |
| I-44 | $C_3H_7$ | $CONHCH_3$ | 4-Cl | N | CC |

TABLE 2

| Compound number | $R^1$ | $R^2$ | Ym | A | Type |
|---|---|---|---|---|---|
| I-45 | $ClCH_2$ | COOH | 4-Cl | N | CC |
| I-46 | $ClCH_2$ | $COOCH_3$ | 4-Cl | N | CC |
| I-47 | $ClCH_2$ | $COOCH_2CH_3$ | 4-Cl | N | CC |
| I-48 | $ClCH_2$ | $COOCH_2CH_2CH_3$ | 4-Cl | N | CC |
| I-49 | $BrCH_2$ | COOH | 4-Cl | N | CC |
| I-50 | $BrCH_2$ | $COOCH_3$ | 4-Cl | N | CC |
| I-51 | $BrCH_2$ | $COOCH_2CH_3$ | 4-Cl | N | CC |
| I-52 | $CH_3$ | COOH | 4-F | N | CC |
| I-53 | $CH_3$ | $COOCH_3$ | 4-F | N | CC |
| I-54 | $CH_3$ | $COOCH_2CH_3$ | 4-F | N | CC |
| I-55 | $CH_3$ | $COOCH_2CH=CH_2$ | 4-F | N | CC |
| I-56 | $CH_3$ | $COOCH_2C\equiv CH$ | 4-F | N | CC |
| I-57 | $CH_3$ | $COOCH_2CH_2CH_3$ | 4-F | N | CC |
| I-58 | $CH_3$ | $COOCH(CH_3)_2$ | 4-F | N | CC |
| I-59 | $CH_3$ | $COOC(CH_3)_3$ | 4-F | N | CC |
| I-60 | $CH_3$ | $COOCH_2CH=CH(CH_3)$ | 4-F | N | CC |
| I-61 | $CH_3$ | $CONHCH_3$ | 4-F | N | CC |
| I-62 | $CH_3$ | $CONHCH_2CH_3$ | 4-F | N | CC |
| I-63 | $CH_3$ | $CONHCH_2CH_2CH_3$ | 4-F | N | CC |
| I-64 | $CH_3$ | $CONHCH(CH_3)_2$ | 4-F | N | CC |
| I-65 | $C_2H_5$ | COOH | 4-F | N | CC |
| I-66 | $C_2H_5$ | $COOCH_3$ | 4-F | N | CC |
| I-67 | $C_2H_5$ | $COOCH_2CH_3$ | 4-F | N | CC |
| I-68 | $C_2H_5$ | $COOCH_2CH_2CH_3$ | 4-F | N | CC |
| I-69 | $C_2H_5$ | $COOCH(CH_3)_2$ | 4-F | N | CC |
| I-70 | $C_2H_5$ | $CONHCH_3$ | 4-F | N | CC |
| I-71 | $C_3H_7$ | COOH | 4-F | N | CC |
| I-72 | $C_3H_7$ | $COOCH_3$ | 4-F | N | CC |
| I-73 | $C_3H_7$ | $COOCH_2CH_3$ | 4-F | N | CC |
| I-74 | $C_3H_7$ | $COOCH_2CH_2CH_3$ | 4-F | N | CC |
| I-75 | $C_3H_7$ | $COOCH(CH_3)_2$ | 4-F | N | CC |
| I-76 | $C_3H_7$ | $CONHCH_3$ | 4-F | N | CC |
| I-77 | $ClCH_2$ | COOH | 4-F | N | CC |
| I-78 | $ClCH_2$ | $COOCH_3$ | 4-F | N | CC |
| I-79 | $ClCH_2$ | $COOCH_2CH_3$ | 4-F | N | CC |
| I-80 | $ClCH_2$ | $COOCH_2CH_2CH_3$ | 4-F | N | CC |
| I-81 | $BrCH_2$ | COOH | 4-F | N | CC |
| I-82 | $BrCH_2$ | $COOCH_3$ | 4-F | N | CC |
| I-83 | $BrCH_2$ | $COOCH_2CH_3$ | 4-F | N | CC |
| I-84 | $CH_3$ | COOH | 4-H | N | CC |
| I-85 | $CH_3$ | $COOCH_3$ | 4-H | N | CC |
| I-86 | $CH_3$ | $COOCH_2CH_3$ | 4-H | N | CC |
| I-87 | $CH_3$ | $COOCH_2CH=CH_2$ | 4-H | N | CC |
| I-88 | $CH_3$ | $COOCH_2C\equiv CH$ | 4-H | N | CC |
| I-89 | $CH_3$ | $COOCH_2CH_2CH_3$ | 4-H | N | CC |
| I-90 | $CH_3$ | $COOCH(CH_3)_2$ | 4-H | N | CC |
| I-91 | $CH_3$ | $CONHCH_3$ | 4-H | N | CC |

TABLE 3

| Compound number | $R^1$ | $R^2$ | Ym | A | Type |
|---|---|---|---|---|---|
| I-92 | $C_2H_5$ | COOH | 4-H | N | CC |
| I-93 | $C_2H_5$ | $COOCH_3$ | 4-H | N | CC |
| I-94 | $C_2H_5$ | $COOCH_2CH_3$ | 4-H | N | CC |
| I-95 | $C_2H_5$ | $COOCH_2CH_2CH_3$ | 4-H | N | CC |
| I-96 | $C_2H_5$ | $COOCH(CH_3)_2$ | 4-H | N | CC |
| I-97 | $C_2H_5$ | $CONHCH_3$ | 4-H | N | CC |
| I-98 | $C_3H_7$ | COOH | 4-H | N | CC |
| I-99 | $C_3H_7$ | $COOCH_3$ | 4-H | N | CC |
| I-100 | $C_3H_7$ | $COOCH_2CH_3$ | 4-H | N | CC |
| I-101 | $C_3H_7$ | $COOCH_2CH=CH_2$ | 4-H | N | CC |
| I-102 | $C_3H_7$ | $COOCH_2C\equiv CH$ | 4-H | N | CC |
| I-103 | $C_3H_7$ | $COOCH_2CH_2CH_3$ | 4-H | N | CC |
| I-104 | $C_3H_7$ | $COOCH(CH_3)_2$ | 4-H | N | CC |
| I-105 | $C_3H_7$ | $CONHCH_3$ | 4-H | N | CC |
| I-106 | $ClCH_2$ | COOH | 4-H | N | CC |
| I-107 | $ClCH_2$ | $COOCH_3$ | 4-H | N | CC |
| I-108 | $ClCH_2$ | $COOCH_2CH_3$ | 4-H | N | CC |
| I-109 | $ClCH_2$ | $COOCH_2CH_2CH_3$ | 4-H | N | CC |
| I-110 | $BrCH_2$ | COOH | 4-H | N | CC |
| I-111 | $BrCH_2$ | $COOCH_3$ | 4-H | N | CC |
| I-112 | $BrCH_2$ | $COOCH_2CH_3$ | 4-H | N | CC |
| I-113 | $CH_3$ | $COOCH_3$ | 2-Cl | N | CC |
| I-114 | $CH_3$ | $COOCH_3$ | 3-Cl | N | CC |
| I-115 | $CH_3$ | $COOCH_3$ | 2-F | N | CC |
| I-116 | $CH_3$ | $COOCH_3$ | 3-F | N | CC |
| I-117 | $CH_3$ | $COOCH_3$ | 2,4-Cl | N | CC |
| I-118 | $CH_3$ | $COOCH_3$ | 3,4-Cl | N | CC |
| I-119 | $CH_3$ | $COOCH_3$ | 2,4-F | N | CC |
| I-120 | $CH_3$ | $COOCH_3$ | 3,4-F | N | CC |
| I-121 | $CH_3$ | $COOCH_3$ | 4-Me | N | CC |
| I-122 | $CH_3$ | $COOCH_3$ | 4-Ph | N | CC |
| I-123 | $CH_3$ | $COOCH_3$ | $4-CF_3$ | N | CC |
| I-124 | $CH_3$ | $COOCH_3$ | $4-CF_3O$ | N | CC |
| I-125 | $CH_3$ | $COOCH_3$ | 4-Br | N | CC |
| I-126 | $CH_3$ | $COOCH_3$ | 4-Cl | CH | CC |
| I-127 | $CH_3$ | $COOCH_2CH_3$ | 4-Cl | CH | CC |
| I-128 | $C_2H_5$ | $COOCH_3$ | 4-Cl | CH | CC |
| I-129 | $C_3H_7$ | $COOCH_3$ | 4-Cl | CH | CC |
| I-130 | $ClCH_2$ | $COOCH_3$ | 4-Cl | CH | CC |

TABLE 4

| Compound number | R¹ | R² | Ym | A | Type |
|---|---|---|---|---|---|
| I-131 | $CH_3$ | COOH | 4-Cl | N | TC |
| I-132 | $CH_3$ | $COOCH_3$ | 4-Cl | N | TC |
| I-133 | $CH_3$ | $COOCH_2CH_3$ | 4-Cl | N | TC |
| I-134 | $CH_3$ | $COOCH_2CH=CH_2$ | 4-Cl | N | TC |
| I-135 | $CH_3$ | $COOCH_2C\equiv CH$ | 4-Cl | N | TC |
| I-136 | $CH_3$ | $COOCH_2CH_2CH_3$ | 4-Cl | N | TC |
| I-137 | $CH_3$ | $COOCH(CH_3)_2$ | 4-Cl | N | TC |
| I-138 | $CH_3$ | $COOCH_2CH_2CH_2CH_3$ | 4-Cl | N | TC |
| I-139 | $CH_3$ | $COOCH_2CH(CH_3)CH_3$ | 4-Cl | N | TC |
| I-140 | $CH_3$ | $COOCH(CH_3)CH_2CH_3$ | 4-Cl | N | TC |
| I-141 | $CH_3$ | $COOC(CH_3)_3$ | 4-Cl | N | TC |
| I-142 | $CH_3$ | $COOCH_2CH_2CH_2CH_2CH_3$ | 4-Cl | N | TC |
| I-143 | $CH_3$ | $COOCH(CH_3)_2CH_2CH_3$ | 4-Cl | N | TC |
| I-144 | $CH_3$ | $COOCH_2C(CH_3)_3$ | 4-Cl | N | TC |
| I-145 | $CH_3$ | $COOCH_2CH=CH(CH_3)$ | 4-Cl | N | TC |
| I-146 | $CH_3$ | $COOCH_2C(CH_3)=CH_2$ | 4-Cl | N | TC |
| I-147 | $CH_3$ | $COOCH_2C\equiv CCH_3$ | 4-Cl | N | TC |
| I-148 | $CH_3$ | $CONHCH_3$ | 4-Cl | N | TC |
| I-149 | $CH_3$ | $CONHCH_2CH_3$ | 4-Cl | N | TC |
| I-150 | $CH_3$ | $CONHCH_2CH_2CH_3$ | 4-Cl | N | TC |
| I-151 | $CH_3$ | $CONHCH(CH_3)_2$ | 4-Cl | N | TC |
| I-152 | $CH_3$ | $CONHCH_2CH=CH_2$ | 4-Cl | N | TC |
| I-153 | $CH_3$ | $CONHCH_2C\equiv CH$ | 4-Cl | N | TC |
| I-154 | $CH_3$ | $CON(CH_3)_2$ | 4-Cl | N | TC |
| I-155 | $CH_3$ | $CON(CH_2CH_3)_2$ | 4-Cl | N | TC |
| I-156 | $CH_3$ | $CON(CH_3)CH_2CH_3$ | 4-Cl | N | TC |
| I-157 | $CH_3$ | CHO | 4-Cl | N | TC |
| I-158 | $CH_3$ | $COCH_3$ | 4-Cl | N | TC |
| I-159 | $C_2H_5$ | COOH | 4-Cl | N | TC |
| I-160 | $C_2H_5$ | $COOCH_3$ | 4-Cl | N | TC |
| I-161 | $C_2H_5$ | $COOCH_2CH_3$ | 4-Cl | N | TC |
| I-162 | $C_2H_5$ | $COOCH_2CH=CH_2$ | 4-Cl | N | TC |
| I-163 | $C_2H_5$ | $COOCH_2C\equiv CH$ | 4-Cl | N | TC |
| I-164 | $C_2H_5$ | $COOCH_2CH_2CH_3$ | 4-Cl | N | TC |
| I-165 | $C_2H_5$ | $COOCH(CH_3)_2$ | 4-Cl | N | TC |
| I-166 | $C_2H_5$ | $CONHCH_3$ | 4-Cl | N | TC |
| I-167 | $C_3H_7$ | COOH | 4-Cl | N | TC |
| I-168 | $C_3H_7$ | $COOCH_3$ | 4-Cl | N | TC |
| I-169 | $C_3H_7$ | $COOCH_2CH_3$ | 4-Cl | N | TC |
| I-170 | $C_3H_7$ | $COOCH_2CH=CH_2$ | 4-Cl | N | TC |
| I-171 | $C_3H_7$ | $COOCH_2C\equiv CH$ | 4-Cl | N | TC |
| I-172 | $C_3H_7$ | $COOCH_2CH_2CH_3$ | 4-Cl | N | TC |
| I-173 | $C_3H_7$ | $COOCH(CH_3)_2$ | 4-Cl | N | TC |
| I-174 | $C_3H_7$ | $CONHCH_3$ | 4-Cl | N | TC |

TABLE 5

| Compound number | R¹ | R² | Ym | A | Type |
|---|---|---|---|---|---|
| I-175 | $ClCH_2$ | COOH | 4-Cl | N | TC |
| I-176 | $ClCH_2$ | $COOCH_3$ | 4-Cl | N | TC |
| I-177 | $ClCH_2$ | $COOCH_2CH_3$ | 4-Cl | N | TC |
| I-178 | $ClCH_2$ | $COOCH_2CH_2CH_3$ | 4-Cl | N | TC |
| I-179 | $BrCH_2$ | COOH | 4-Cl | N | TC |
| I-180 | $BrCH_2$ | $COOCH_3$ | 4-Cl | N | TC |
| I-181 | $BrCH_2$ | $COOCH_2CH_3$ | 4-Cl | N | TC |
| I-182 | $CH_3$ | COOH | 4-F | N | TC |
| I-183 | $CH_3$ | $COOCH_3$ | 4-F | N | TC |
| I-184 | $CH_3$ | $COOCH_2CH_3$ | 4-F | N | TC |
| I-185 | $CH_3$ | $COOCH_2CH=CH_2$ | 4-F | N | TC |
| I-186 | $CH_3$ | $COOCH_2C\equiv CH$ | 4-F | N | TC |
| I-187 | $CH_3$ | $COOCH_2CH_2CH_3$ | 4-F | N | TC |
| I-188 | $CH_3$ | $COOCH(CH_3)_2$ | 4-F | N | TC |
| I-189 | $CH_3$ | $COOC(CH_3)_3$ | 4-F | N | TC |
| I-190 | $CH_3$ | $COOCH_2CH=CH(CH_3)$ | 4-F | N | TC |
| I-191 | $CH_3$ | $CONHCH_3$ | 4-F | N | TC |
| I-192 | $CH_3$ | $CONHCH_2CH_3$ | 4-F | N | TC |
| I-193 | $CH_3$ | $CONHCH_2CH_2CH_3$ | 4-F | N | TC |
| I-194 | $CH_3$ | $CONHCH(CH_3)_2$ | 4-F | N | TC |
| I-195 | $C_2H_5$ | COOH | 4-F | N | TC |
| I-196 | $C_2H_5$ | $COOCH_3$ | 4-F | N | TC |
| I-197 | $C_2H_5$ | $COOCH_2CH_3$ | 4-F | N | TC |
| I-198 | $C_2H_5$ | $COOCH_2CH_2CH_3$ | 4-F | N | TC |
| I-199 | $C_2H_5$ | $COOCH(CH_3)_2$ | 4-F | N | TC |
| I-200 | $C_2H_5$ | $CONHCH_3$ | 4-F | N | TC |
| I-201 | $C_3H_7$ | COOH | 4-F | N | TC |
| I-202 | $C_3H_7$ | $COOCH_3$ | 4-F | N | TC |
| I-203 | $C_3H_7$ | $COOCH_2CH_3$ | 4-F | N | TC |
| I-204 | $C_3H_7$ | $COOCH_2CH_2CH_3$ | 4-F | N | TC |
| I-205 | $C_3H_7$ | $COOCH(CH_3)_2$ | 4-F | N | TC |
| I-206 | $C_3H_7$ | $CONHCH_3$ | 4-F | N | TC |
| I-207 | $ClCH_2$ | COOH | 4-F | N | TC |
| I-208 | $ClCH_2$ | $COOCH_3$ | 4-F | N | TC |
| I-209 | $ClCH_2$ | $COOCH_2CH_3$ | 4-F | N | TC |
| I-210 | $ClCH_2$ | $COOCH_2CH_2CH_3$ | 4-F | N | TC |
| I-211 | $BrCH_2$ | COOH | 4-F | N | TC |
| I-212 | $BrCH_2$ | $COOCH_3$ | 4-F | N | TC |
| I-213 | $BrCH_2$ | $COOCH_2CH_3$ | 4-F | N | TC |
| I-214 | $CH_3$ | COOH | 4-H | N | TC |
| I-215 | $CH_3$ | $COOCH_3$ | 4-H | N | TC |
| I-216 | $CH_3$ | $COOCH_2CH_3$ | 4-H | N | TC |
| I-217 | $CH_3$ | $COOCH_2CH=CH_2$ | 4-H | N | TC |
| I-218 | $CH_3$ | $COOCH_2C\equiv CH$ | 4-H | N | TC |
| I-219 | $CH_3$ | $COOCH_2CH_2CH_3$ | 4-H | N | TC |
| I-220 | $CH_3$ | $COOCH(CH_3)_2$ | 4-H | N | TC |
| I-221 | $CH_3$ | $CONHCH_3$ | 4-H | N | TC |

TABLE 6

| Compound number | R¹ | R² | Ym | A | Type |
|---|---|---|---|---|---|
| I-222 | $C_2H_5$ | COOH | 4-H | N | TC |
| I-223 | $C_2H_5$ | $COOCH_3$ | 4-H | N | TC |
| I-224 | $C_2H_5$ | $COOCH_2CH_3$ | 4-H | N | TC |
| I-225 | $C_2H_5$ | $COOCH_2CH_2CH_3$ | 4-H | N | TC |
| I-226 | $C_2H_5$ | $COOCH(CH_3)_2$ | 4-H | N | TC |
| I-227 | $C_2H_5$ | $CONHCH_3$ | 4-H | N | TC |
| I-228 | $C_3H_7$ | COOH | 4-H | N | TC |
| I-229 | $C_3H_7$ | $COOCH_3$ | 4-H | N | TC |
| I-230 | $C_3H_7$ | $COOCH_2CH_3$ | 4-H | N | TC |
| I-231 | $C_3H_7$ | $COOCH_2CH=CH_2$ | 4-H | N | TC |
| I-232 | $C_3H_7$ | $COOCH_2C\equiv CH$ | 4-H | N | TC |
| I-233 | $C_3H_7$ | $COOCH_2CH_2CH_3$ | 4-H | N | TC |
| I-234 | $C_3H_7$ | $COOCH(CH_3)_2$ | 4-H | N | TC |
| I-235 | $C_3H_7$ | $CONHCH_3$ | 4-H | N | TC |
| I-236 | $ClCH_2$ | COOH | 4-H | N | TC |
| I-237 | $ClCH_2$ | $COOCH_3$ | 4-H | N | TC |
| I-238 | $ClCH_2$ | $COOCH_2CH_3$ | 4-H | N | TC |
| I-239 | $ClCH_2$ | $COOCH_2CH_2CH_3$ | 4-H | N | TC |
| I-240 | $BrCH_2$ | COOH | 4-H | N | TC |
| I-241 | $BrCH_2$ | $COOCH_3$ | 4-H | N | TC |
| I-242 | $BrCH_2$ | $COOCH_2CH_3$ | 4-H | N | TC |
| I-243 | $CH_3$ | $COOCH_3$ | 2-Cl | N | TC |
| I-244 | $CH_3$ | $COOCH_3$ | 3-Cl | N | TC |
| I-245 | $CH_3$ | $COOCH_3$ | 2-F | N | TC |
| I-246 | $CH_3$ | $COOCH_3$ | 3-F | N | TC |
| I-247 | $CH_3$ | $COOCH_3$ | 2,4-Cl | N | TC |
| I-248 | $CH_3$ | $COOCH_3$ | 3,4-Cl | N | TC |
| I-249 | $CH_3$ | $COOCH_3$ | 2,4-F | N | TC |
| I-250 | $CH_3$ | $COOCH_3$ | 3,4-F | N | TC |
| I-251 | $CH_3$ | $COOCH_3$ | 4-Me | N | TC |
| I-252 | $CH_3$ | $COOCH_3$ | 4-Ph | N | TC |
| I-253 | $CH_3$ | $COOCH_3$ | 4-$CF_3$ | N | TC |
| I-254 | $CH_3$ | $COOCH_3$ | 4-$CF_3$O | N | TC |
| I-255 | $CH_3$ | $COOCH_3$ | 4-Br | N | TC |
| I-256 | $CH_3$ | $COOCH_3$ | 4-Cl | CH | TC |
| I-257 | $CH_3$ | $COOCH_2CH_3$ | 4-Cl | CH | TC |
| I-258 | $C_2H_5$ | $COOCH_3$ | 4-Cl | CH | TC |
| I-259 | $C_3H_7$ | $COOCH_3$ | 4-Cl | CH | TC |
| I-260 | $ClCH_2$ | $COOCH_3$ | 4-Cl | CH | TC |

TABLE 7

| Compound number | R$^1$ | R$^2$ | Ym | A | Type |
|---|---|---|---|---|---|
| I-261 | CH$_3$ | COOH | 4-Cl | N | CT |
| I-262 | CH$_3$ | COOCH$_3$ | 4-Cl | N | CT |
| I-263 | CH$_3$ | COOCH$_2$CH$_3$ | 4-Cl | N | CT |
| I-264 | CH$_3$ | COOCH$_2$CH=CH$_2$ | 4-Cl | N | CT |
| I-265 | CH$_3$ | COOCH$_2$C≡CH | 4-Cl | N | CT |
| I-266 | CH$_3$ | COOCH$_2$CH$_2$CH$_3$ | 4-Cl | N | CT |
| I-267 | CH$_3$ | COOCH(CH$_3$)$_2$ | 4-Cl | N | CT |
| I-268 | CH$_3$ | COOCH$_2$CH$_2$CH$_2$CH$_3$ | 4-Cl | N | CT |
| I-269 | CH$_3$ | COOCH$_2$CH(CH$_3$)CH$_3$ | 4-Cl | N | CT |
| I-270 | CH$_3$ | COOCH(CH$_3$)CH$_2$CH$_3$ | 4-Cl | N | CT |
| I-271 | CH$_3$ | COOC(CH$_3$)$_3$ | 4-Cl | N | CT |
| I-272 | CH$_3$ | COOCH$_2$CH$_2$CH$_2$CH$_2$CH$_3$ | 4-Cl | N | CT |
| I-273 | CH$_3$ | COOCH(CH$_3$)$_2$CH$_2$CH$_3$ | 4-Cl | N | CT |
| I-274 | CH$_3$ | COOCH$_2$C(CH$_3$)$_3$ | 4-Cl | N | CT |
| I-275 | CH$_3$ | COOCH$_2$CH=CH(CH$_3$) | 4-Cl | N | CT |
| I-276 | CH$_3$ | COOCH$_2$C(CH$_3$)=CH$_2$ | 4-Cl | N | CT |
| I-277 | CH$_3$ | COOCH$_2$C≡CCH$_3$ | 4-Cl | N | CT |
| I-278 | CH$_3$ | CONHCH$_3$ | 4-Cl | N | CT |
| I-279 | CH$_3$ | CONHCH$_2$CH$_3$ | 4-Cl | N | CT |
| I-280 | CH$_3$ | CONHCH$_2$CH$_2$CH$_3$ | 4-Cl | N | CT |
| I-281 | CH$_3$ | CONHCH(CH$_3$)$_2$ | 4-Cl | N | CT |
| I-282 | CH$_3$ | CONHCH$_2$CH=CH$_2$ | 4-Cl | N | CT |
| I-283 | CH$_3$ | CONHCH$_2$C≡CH | 4-Cl | N | CT |
| I-284 | CH$_3$ | CON(CH$_3$)$_2$ | 4-Cl | N | CT |
| I-285 | CH$_3$ | CON(CH$_2$CH$_3$)$_2$ | 4-Cl | N | CT |
| I-286 | CH$_3$ | CON(CH$_3$)CH$_2$CH$_3$ | 4-Cl | N | CT |
| I-287 | CH$_3$ | CHO | 4-Cl | N | CT |
| I-288 | CH$_3$ | COCH$_3$ | 4-Cl | N | CT |
| I-289 | C$_2$H$_5$ | COOH | 4-Cl | N | CT |
| I-290 | C$_2$H$_5$ | COOCH$_3$ | 4-Cl | N | CT |
| I-291 | C$_2$H$_5$ | COOCH$_2$CH$_3$ | 4-Cl | N | CT |
| I-292 | C$_2$H$_5$ | COOCH$_2$CH=CH$_2$ | 4-Cl | N | CT |
| I-293 | C$_2$H$_5$ | COOCH$_2$C≡CH | 4-Cl | N | CT |
| I-294 | C$_2$H$_5$ | COOCH$_2$CH$_2$CH$_3$ | 4-Cl | N | CT |
| I-295 | C$_2$H$_5$ | COOCH(CH$_3$)$_2$ | 4-Cl | N | CT |
| I-296 | C$_2$H$_5$ | CONHCH$_3$ | 4-Cl | N | CT |
| I-297 | C$_3$H$_7$ | COOH | 4-Cl | N | CT |
| I-298 | C$_3$H$_7$ | COOCH$_3$ | 4-Cl | N | CT |
| I-299 | C$_3$H$_7$ | COOCH$_2$CH$_3$ | 4-Cl | N | CT |
| I-300 | C$_3$H$_7$ | COOCH$_2$CH=CH$_2$ | 4-Cl | N | CT |
| I-301 | C$_3$H$_7$ | COOCH$_2$C≡CH | 4-Cl | N | CT |
| I-302 | C$_3$H$_7$ | COOCH$_2$CH$_2$CH$_3$ | 4-Cl | N | CT |
| I-303 | C$_3$H$_7$ | COOCH(CH$_3$)$_2$ | 4-Cl | N | CT |
| I-304 | C$_3$H$_7$ | CONHCH$_3$ | 4-Cl | N | CT |

TABLE 8

| Compound number | R$^1$ | R$^2$ | Ym | A | Type |
|---|---|---|---|---|---|
| I-305 | ClCH$_2$ | COOH | 4-Cl | N | CT |
| I-306 | ClCH$_2$ | COOCH$_3$ | 4-Cl | N | CT |
| I-307 | ClCH$_2$ | COOCH$_2$CH$_3$ | 4-Cl | N | CT |
| I-308 | ClCH$_2$ | COOCH$_2$CH$_2$CH$_3$ | 4-Cl | N | CT |
| I-309 | BrCH$_2$ | COOH | 4-Cl | N | CT |
| I-310 | BrCH$_2$ | COOCH$_3$ | 4-Cl | N | CT |
| I-311 | BrCH$_2$ | COOCH$_2$CH$_3$ | 4-Cl | N | CT |
| I-312 | CH$_3$ | COOH | 4-F | N | CT |
| I-313 | CH$_3$ | COOCH$_3$ | 4-F | N | CT |
| I-314 | CH$_3$ | COOCH$_2$CH$_3$ | 4-F | N | CT |
| I-315 | CH$_3$ | COOCH$_2$CH=CH$_2$ | 4-F | N | CT |
| I-316 | CH$_3$ | COOCH$_2$C≡CH | 4-F | N | CT |
| I-317 | CH$_3$ | COOCH$_2$CH$_2$CH$_3$ | 4-F | N | CT |
| I-318 | CH$_3$ | COOCH(CH$_3$)$_2$ | 4-F | N | CT |
| I-319 | CH$_3$ | COOC(CH$_3$)$_3$ | 4-F | N | CT |
| I-320 | CH$_3$ | COOCH$_2$CH=CH(CH$_3$) | 4-F | N | CT |
| I-321 | CH$_3$ | CONHCH$_3$ | 4-F | N | CT |
| I-322 | CH$_3$ | CONHCH$_2$CH$_3$ | 4-F | N | CT |
| I-323 | CH$_3$ | CONHCH$_2$CH$_2$CH$_3$ | 4-F | N | CT |
| I-324 | CH$_3$ | CONHCH(CH$_3$)$_2$ | 4-F | N | CT |
| I-325 | C$_2$H$_5$ | COOH | 4-F | N | CT |
| I-326 | C$_2$H$_5$ | COOCH$_3$ | 4-F | N | CT |
| I-327 | C$_2$H$_5$ | COOCH$_2$CH$_3$ | 4-F | N | CT |
| I-328 | C$_2$H$_5$ | COOCH$_2$CH$_2$CH$_3$ | 4-F | N | CT |
| I-329 | C$_2$H$_5$ | COOCH(CH$_3$)$_2$ | 4-F | N | CT |
| I-330 | C$_2$H$_5$ | CONHCH$_3$ | 4-F | N | CT |
| I-331 | C$_3$H$_7$ | COOH | 4-F | N | CT |
| I-332 | C$_3$H$_7$ | COOCH$_3$ | 4-F | N | CT |
| I-333 | C$_3$H$_7$ | COOCH$_2$CH$_3$ | 4-F | N | CT |
| I-334 | C$_3$H$_7$ | COOCH$_2$CH$_2$CH$_3$ | 4-F | N | CT |
| I-335 | C$_3$H$_7$ | COOCH(CH$_3$)$_2$ | 4-F | N | CT |
| I-336 | C$_3$H$_7$ | CONHCH$_3$ | 4-F | N | CT |
| I-337 | ClCH$_2$ | COOH | 4-F | N | CT |
| I-338 | ClCH$_2$ | COOCH$_3$ | 4-F | N | CT |
| I-339 | ClCH$_2$ | COOCH$_2$CH$_3$ | 4-F | N | CT |
| I-340 | ClCH$_2$ | COOCH$_2$CH$_2$CH$_3$ | 4-F | N | CT |
| I-341 | BrCH$_2$ | COOH | 4-F | N | CT |
| I-342 | BrCH$_2$ | COOCH$_3$ | 4-F | N | CT |
| I-343 | BrCH$_2$ | COOCH$_2$CH$_3$ | 4-F | N | CT |
| I-344 | CH$_3$ | COOH | 4-H | N | CT |
| I-345 | CH$_3$ | COOCH$_3$ | 4-H | N | CT |
| I-346 | CH$_3$ | COOCH$_2$CH$_3$ | 4-H | N | CT |
| I-347 | CH$_3$ | COOCH$_2$CH=CH$_2$ | 4-H | N | CT |
| I-348 | CH$_3$ | COOCH$_2$C≡CH | 4-H | N | CT |
| I-349 | CH$_3$ | COOCH$_2$CH$_2$CH$_3$ | 4-H | N | CT |
| I-350 | CH$_3$ | COOCH(CH$_3$)$_2$ | 4-H | N | CT |
| I-351 | CH$_3$ | CONHCH$_3$ | 4-H | N | CT |

TABLE 9

| Compound number | R$^1$ | R$^2$ | Ym | A | Type |
|---|---|---|---|---|---|
| I-352 | C$_2$H$_5$ | COOH | 4-H | N | CT |
| I-353 | C$_2$H$_5$ | COOCH$_3$ | 4-H | N | CT |
| I-354 | C$_2$H$_5$ | COOCH$_2$CH$_3$ | 4-H | N | CT |
| I-355 | C$_2$H$_5$ | COOCH$_2$CH$_2$CH$_3$ | 4-H | N | CT |
| I-356 | C$_2$H$_5$ | COOCH(CH$_3$)$_2$ | 4-H | N | CT |
| I-357 | C$_2$H$_5$ | CONHCH$_3$ | 4-H | N | CT |
| I-358 | C$_3$H$_7$ | COOH | 4-H | N | CT |
| I-359 | C$_3$H$_7$ | COOCH$_3$ | 4-H | N | CT |
| I-360 | C$_3$H$_7$ | COOCH$_2$CH$_3$ | 4-H | N | CT |
| I-361 | C$_3$H$_7$ | COOCH$_2$CH=CH$_2$ | 4-H | N | CT |
| I-362 | C$_3$H$_7$ | COOCH$_2$C≡CH | 4-H | N | CT |
| I-363 | C$_3$H$_7$ | COOCH$_2$CH$_2$CH$_3$ | 4-H | N | CT |
| I-364 | C$_3$H$_7$ | COOCH(CH$_3$)$_2$ | 4-H | N | CT |
| I-365 | C$_3$H$_7$ | CONHCH$_3$ | 4-H | N | CT |
| I-366 | ClCH$_2$ | COOH | 4-H | N | CT |
| I-367 | ClCH$_2$ | COOCH$_3$ | 4-H | N | CT |
| I-368 | ClCH$_2$ | COOCH$_2$CH$_3$ | 4-H | N | CT |
| I-369 | ClCH$_2$ | COOCH$_2$CH$_2$CH$_3$ | 4-H | N | CT |
| I-370 | BrCH$_2$ | COOH | 4-H | N | CT |
| I-371 | BrCH$_2$ | COOCH$_3$ | 4-H | N | CT |
| I-372 | BrCH$_2$ | COOCH$_2$CH$_3$ | 4-H | N | CT |
| I-373 | CH$_3$ | COOCH$_3$ | 2-Cl | N | CT |
| I-374 | CH$_3$ | COOCH$_3$ | 3-Cl | N | CT |
| I-375 | CH$_3$ | COOCH$_3$ | 2-F | N | CT |
| I-376 | CH$_3$ | COOCH$_3$ | 3-F | N | CT |
| I-377 | CH$_3$ | COOCH$_3$ | 2,4-Cl | N | CT |
| I-378 | CH$_3$ | COOCH$_3$ | 3,4-Cl | N | CT |
| I-379 | CH$_3$ | COOCH$_3$ | 2,4-F | N | CT |
| I-380 | CH$_3$ | COOCH$_3$ | 3,4-F | N | CT |
| I-381 | CH$_3$ | COOCH$_3$ | 4-Me | N | CT |
| I-382 | CH$_3$ | COOCH$_3$ | 4-Ph | N | CT |
| I-383 | CH$_3$ | COOCH$_3$ | 4-CF$_3$ | N | CT |
| I-384 | CH$_3$ | COOCH$_3$ | 4-CF$_3$O | N | CT |
| I-385 | CH$_3$ | COOCH$_3$ | 4-Br | N | CT |
| I-386 | CH$_3$ | COOCH$_3$ | 4-Cl | CH | CT |
| I-387 | CH$_3$ | COOCH$_2$CH$_3$ | 4-Cl | CH | CT |
| I-388 | C$_2$H$_5$ | COOCH$_3$ | 4-Cl | CH | CT |
| I-389 | C$_3$H$_7$ | COOCH$_3$ | 4-Cl | CH | CT |
| I-390 | ClCH$_2$ | COOCH$_3$ | 4-Cl | CH | CT |

TABLE 10

| Compound number | R¹ | R² | Ym | A | Type |
|---|---|---|---|---|---|
| I-391 | $CH_3$ | COOH | 4-Cl | N | TT |
| I-392 | $CH_3$ | $COOCH_3$ | 4-Cl | N | TT |
| I-393 | $CH_3$ | $COOCH_2CH_3$ | 4-Cl | N | TT |
| I-394 | $CH_3$ | $COOCH_2CH=CH_2$ | 4-Cl | N | TT |
| I-395 | $CH_3$ | $COOCH_2C\equiv CH$ | 4-Cl | N | TT |
| I-396 | $CH_3$ | $COOCH_2CH_2CH_3$ | 4-Cl | N | TT |
| I-397 | $CH_3$ | $COOCH(CH_3)_2$ | 4-Cl | N | TT |
| I-398 | $CH_3$ | $COOCH_2CH_2CH_2CH_3$ | 4-Cl | N | TT |
| I-399 | $CH_3$ | $COOCH_2CH(CH_3)CH_3$ | 4-Cl | N | TT |
| I-400 | $CH_3$ | $COOCH(CH_3)CH_2CH_3$ | 4-Cl | N | TT |
| I-401 | $CH_3$ | $COOC(CH_3)_3$ | 4-Cl | N | TT |
| I-402 | $CH_3$ | $COOCH_2CH_2CH_2CH_2CH_3$ | 4-Cl | N | TT |
| I-403 | $CH_3$ | $COOCH(CH_3)_2CH_2CH_3$ | 4-Cl | N | TT |
| I-404 | $CH_3$ | $COOCH_2C(CH_3)_3$ | 4-Cl | N | TT |
| I-405 | $CH_3$ | $COOCH_2CH=CH(CH_3)$ | 4-Cl | N | TT |
| I-406 | $CH_3$ | $COOCH_2C(CH_3)=CH_2$ | 4-Cl | N | TT |
| I-407 | $CH_3$ | $COOCH_2C\equiv CCH_3$ | 4-Cl | N | TT |
| I-408 | $CH_3$ | $CONHCH_3$ | 4-Cl | N | TT |
| I-409 | $CH_3$ | $CONHCH_2CH_3$ | 4-Cl | N | TT |
| I-410 | $CH_3$ | $CONHCH_2CH_2CH_3$ | 4-Cl | N | TT |
| I-411 | $CH_3$ | $CONHCH(CH_3)_2$ | 4-Cl | N | TT |
| I-412 | $CH_3$ | $CONHCH_2CH=CH_2$ | 4-Cl | N | TT |
| I-413 | $CH_3$ | $CONHCH_2C\equiv CH$ | 4-Cl | N | TT |
| I-414 | $CH_3$ | $CON(CH_3)_2$ | 4-Cl | N | TT |
| I-415 | $CH_3$ | $CON(CH_2CH_3)_2$ | 4-Cl | N | TT |
| I-416 | $CH_3$ | $CON(CH_3)CH_2CH_3$ | 4-Cl | N | TT |
| I-417 | $CH_3$ | CHO | 4-Cl | N | TT |
| I-418 | $CH_3$ | $COCH_3$ | 4-Cl | N | TT |
| I-419 | $C_2H_5$ | COOH | 4-Cl | N | TT |
| I-420 | $C_2H_5$ | $COOCH_3$ | 4-Cl | N | TT |
| I-421 | $C_2H_5$ | $COOCH_2CH_3$ | 4-Cl | N | TT |
| I-422 | $C_2H_5$ | $COOCH_2CH=CH_2$ | 4-Cl | N | TT |
| I-423 | $C_2H_5$ | $COOCH_2C\equiv CH$ | 4-Cl | N | TT |
| I-424 | $C_2H_5$ | $COOCH_2CH_2CH_3$ | 4-Cl | N | TT |
| I-425 | $C_2H_5$ | $COOCH(CH_3)_2$ | 4-Cl | N | TT |
| I-426 | $C_2H_5$ | $CONHCH_3$ | 4-Cl | N | TT |
| I-427 | $C_3H_7$ | COOH | 4-Cl | N | TT |
| I-428 | $C_3H_7$ | $COOCH_3$ | 4-Cl | N | TT |
| I-429 | $C_3H_7$ | $COOCH_2CH_3$ | 4-Cl | N | TT |
| I-430 | $C_3H_7$ | $COOCH_2CH=CH_2$ | 4-Cl | N | TT |
| I-431 | $C_3H_7$ | $COOCH_2C\equiv CH$ | 4-Cl | N | TT |
| I-432 | $C_3H_7$ | $COOCH_2CH_2CH_3$ | 4-Cl | N | TT |
| I-433 | $C_3H_7$ | $COOCH(CH_3)_2$ | 4-Cl | N | TT |
| I-434 | $C_3H_7$ | $CONHCH_3$ | 4-Cl | N | TT |

TABLE 11

| Compound number | R¹ | R² | Ym | A | Type |
|---|---|---|---|---|---|
| I-435 | $ClCH_2$ | COOH | 4-Cl | N | TT |
| I-436 | $ClCH_2$ | $COOCH_3$ | 4-Cl | N | TT |
| I-437 | $ClCH_2$ | $COOCH_2CH_3$ | 4-Cl | N | TT |
| I-438 | $ClCH_2$ | $COOCH_2CH_2CH_3$ | 4-Cl | N | TT |
| I-439 | $BrCH_2$ | COOH | 4-Cl | N | TT |
| I-440 | $BrCH_2$ | $COOCH_3$ | 4-Cl | N | TT |
| I-441 | $BrCH_2$ | $COOCH_2CH_3$ | 4-Cl | N | TT |
| I-442 | $CH_3$ | COOH | 4-F | N | TT |
| I-443 | $CH_3$ | $COOCH_3$ | 4-F | N | TT |
| I-444 | $CH_3$ | $COOCH_2CH_3$ | 4-F | N | TT |
| I-445 | $CH_3$ | $COOCH_2CH=CH_2$ | 4-F | N | TT |
| I-446 | $CH_3$ | $COOCH_2C\equiv CH$ | 4-F | N | TT |
| I-447 | $CH_3$ | $COOCH_2CH_2CH_3$ | 4-F | N | TT |
| I-448 | $CH_3$ | $COOCH(CH_3)_2$ | 4-F | N | TT |
| I-449 | $CH_3$ | $COOC(CH_3)_3$ | 4-F | N | TT |
| I-450 | $CH_3$ | $COOCH_2CH=CH(CH_3)$ | 4-F | N | TT |
| I-451 | $CH_3$ | $CONHCH_3$ | 4-F | N | TT |
| I-452 | $CH_3$ | $CONHCH_2CH_3$ | 4-F | N | TT |
| I-453 | $CH_3$ | $CONHCH_2CH_2CH_3$ | 4-F | N | TT |
| I-454 | $CH_3$ | $CONHCH(CH_3)_2$ | 4-F | N | TT |
| I-455 | $C_2H_5$ | COOH | 4-F | N | TT |
| I-456 | $C_2H_5$ | $COOCH_3$ | 4-F | N | TT |
| I-457 | $C_2H_5$ | $COOCH_2CH_3$ | 4-F | N | TT |
| I-458 | $C_2H_5$ | $COOCH_2CH_2CH_3$ | 4-F | N | TT |
| I-459 | $C_2H_5$ | $COOCH(CH_3)_2$ | 4-F | N | TT |
| I-460 | $C_2H_5$ | $CONHCH_3$ | 4-F | N | TT |
| I-461 | $C_3H_7$ | COOH | 4-F | N | TT |
| I-462 | $C_3H_7$ | $COOCH_3$ | 4-F | N | TT |
| I-463 | $C_3H_7$ | $COOCH_2CH_3$ | 4-F | N | TT |
| I-464 | $C_3H_7$ | $COOCH_2CH_2CH_3$ | 4-F | N | TT |
| I-465 | $C_3H_7$ | $COOCH(CH_3)_2$ | 4-F | N | TT |
| I-466 | $C_3H_7$ | $CONHCH_3$ | 4-F | N | TT |
| I-467 | $ClCH_2$ | COOH | 4-F | N | TT |
| I-468 | $ClCH_2$ | $COOCH_3$ | 4-F | N | TT |
| I-469 | $ClCH_2$ | $COOCH_2CH_3$ | 4-F | N | TT |
| I-470 | $ClCH_2$ | $COOCH_2CH_2CH_3$ | 4-F | N | TT |
| I-471 | $BrCH_2$ | COOH | 4-F | N | TT |
| I-472 | $BrCH_2$ | $COOCH_3$ | 4-F | N | TT |
| I-473 | $BrCH_2$ | $COOCH_2CH_3$ | 4-F | N | TT |
| I-474 | $CH_3$ | COOH | 4-H | N | TT |
| I-475 | $CH_3$ | $COOCH_3$ | 4-H | N | TT |
| I-476 | $CH_3$ | $COOCH_2CH_3$ | 4-H | N | TT |
| I-477 | $CH_3$ | $COOCH_2CH=CH_2$ | 4-H | N | TT |
| I-478 | $CH_3$ | $COOCH_2C\equiv CH$ | 4-H | N | TT |
| I-479 | $CH_3$ | $COOCH_2CH_2CH_3$ | 4-H | N | TT |
| I-480 | $CH_3$ | $COOCH(CH_3)_2$ | 4-H | N | TT |
| I-481 | $CH_3$ | $CONHCH_3$ | 4-H | N | TT |

TABLE 12

| Compound number | R¹ | R² | Ym | A | Type |
|---|---|---|---|---|---|
| I-482 | $C_2H_5$ | COOH | 4-H | N | TT |
| I-483 | $C_2H_5$ | $COOCH_3$ | 4-H | N | TT |
| I-484 | $C_2H_5$ | $COOCH_2CH_3$ | 4-H | N | TT |
| I-485 | $C_2H_5$ | $COOCH_2CH_2CH_3$ | 4-H | N | TT |
| I-486 | $C_2H_5$ | $COOCH(CH_3)_2$ | 4-H | N | TT |
| I-487 | $C_2H_5$ | $CONHCH_3$ | 4-H | N | TT |
| I-488 | $C_3H_7$ | COOH | 4-H | N | TT |
| I-489 | $C_3H_7$ | $COOCH_3$ | 4-H | N | TT |
| I-490 | $C_3H_7$ | $COOCH_2CH_3$ | 4-H | N | TT |
| I-491 | $C_3H_7$ | $COOCH_2CH=CH_2$ | 4-H | N | TT |
| I-492 | $C_3H_7$ | $COOCH_2C\equiv CH$ | 4-H | N | TT |
| I-493 | $C_3H_7$ | $COOCH_2CH_2CH_3$ | 4-H | N | TT |
| I-494 | $C_3H_7$ | $COOCH(CH_3)_2$ | 4-H | N | TT |
| I-495 | $C_3H_7$ | $CONHCH_3$ | 4-H | N | TT |
| I-496 | $ClCH_2$ | COOH | 4-H | N | TT |
| I-497 | $ClCH_2$ | $COOCH_3$ | 4-H | N | TT |
| I-498 | $ClCH_2$ | $COOCH_2CH_3$ | 4-H | N | TT |
| I-499 | $ClCH_2$ | $COOCH_2CH_2CH_3$ | 4-H | N | TT |
| I-500 | $BrCH_2$ | COOH | 4-H | N | TT |
| I-501 | $BrCH_2$ | $COOCH_3$ | 4-H | N | TT |
| I-502 | $BrCH_2$ | $COOCH_2CH_3$ | 4-H | N | TT |
| I-503 | $CH_3$ | $COOCH_3$ | 2-Cl | N | TT |
| I-504 | $CH_3$ | $COOCH_3$ | 3-Cl | N | TT |
| I-505 | $CH_3$ | $COOCH_3$ | 2-F | N | TT |
| I-506 | $CH_3$ | $COOCH_3$ | 3-F | N | TT |
| I-507 | $CH_3$ | $COOCH_3$ | 2,4-Cl | N | TT |
| I-508 | $CH_3$ | $COOCH_3$ | 3,4-Cl | N | TT |
| I-509 | $CH_3$ | $COOCH_3$ | 2,4-F | N | TT |
| I-510 | $CH_3$ | $COOCH_3$ | 3,4-F | N | TT |
| I-511 | $CH_3$ | $COOCH_3$ | 4-Me | N | TT |
| I-512 | $CH_3$ | $COOCH_3$ | 4-Ph | N | TT |
| I-513 | $CH_3$ | $COOCH_3$ | 4-$CF_3$ | N | TT |
| I-514 | $CH_3$ | $COOCH_3$ | 4-$CF_3O$ | N | TT |
| I-515 | $CH_3$ | $COOCH_3$ | 4-Br | N | TT |
| I-516 | $CH_3$ | $COOCH_3$ | 4-Cl | CH | TT |
| I-517 | $CH_3$ | $COOCH_2CH_3$ | 4-Cl | CH | TT |
| I-518 | $C_2H_5$ | $COOCH_3$ | 4-Cl | CH | TT |
| I-519 | $C_3H_7$ | $COOCH_3$ | 4-Cl | CH | TT |
| I-520 | $ClCH_2$ | $COOCH_3$ | 4-Cl | CH | TT |

2. Method for Producing Azole Derivative

Hereinafter, the method for producing the compound (I) will be described. The compound (I) can be produced by the first or second production method described below. In the present embodiment, the solvent, base, acid, and others used in the steps of the production method will be first described before specific description of the production methods. The solvent, base, acid, and others used in the steps of the production methods according to the present invention may be the followings, unless specified otherwise.

(1) Solvent

The solvent for use is not particularly limited, if it is inert to the reaction, and examples thereof normally include ethers such as diethyl ether, tetrahydrofuran (hereinafter, referred to as THF), and dioxane; alcohols such as methanol, ethanol, and isopropanol; aromatic hydrocarbons such as benzene, toluene, and xylene; aliphatic hydrocarbons such as petroleum ether, hexane, and methylcyclohexane; amides such as N,N-dimethylformamide (hereinafter, referred to as DMF), N,N-dimethylacetamide, and N-methyl-2-pyrrolidinone; and the like. In addition, for example, water, acetonitrile, ethyl acetate, acetic anhydride, acetic acid, pyridine, or dimethylsulfoxide may be used as the solvent. These solvents may be used, as two or more of them are mixed.

The solvent may be a solvent composition containing solvents that do not form a homogeneous layer. In such a case, a phase-transfer catalyst, such as a common quaternary ammonium salt or crown ether, may be added to the reaction system.

(2) Base or Acid

A base or an acid may be added to the solvent described above.

The base for use is not particularly limited. Examples of the bases include alkali metal carbonate salts such as sodium carbonate, sodium bicarbonate, potassium carbonate, and potassium bicarbonate; alkali-earth metal carbonate salts such as calcium carbonate and barium carbonate; alkali metal hydroxides such as sodium hydroxide and potassium hydroxide; alkali metals such as lithium, sodium, and potassium; alkali metal alkoxides such as sodium methoxide, sodium ethoxide, and potassium t-butoxide; alkali metal hydrogen compounds such as sodium hydride, potassium hydride, and lithium hydride; organic alkali metal compounds such as n-butyllithium; alkali metals such as sodium, potassium, and lithium; alkali metal amides such as lithium diisopropylamide; organic amines such as triethylamine, pyridine, 4-dimethylaminopyridine, N,N-dimethylaniline, and 1,8-diazabicyclo-7-[5.4.0]undecene; and the like.

The acid for use is not particularly limited. Examples of the acids include inorganic acids such as hydrochloric acid, hydrobromic acid, hydroiodic acid, and sulfuric acid; organic acids such as formic acid, acetic acid, butyric acid, trifluoroacetic acid, and p-toluenesulfonic acid; Lewis acids such as lithium chloride, lithium bromide, rhodium chloride, aluminum chloride, and boron trifluoride; and the like.

(3) First Production Method for Compound (I)

A first production method for the compound (I) will be described below with reference to FIG. 1. FIG. 1 is a chart showing the first and second production methods for the compound (I). More specifically, it is possible according to the first production method for the compound (I) to produce selectively, among the compounds (I), a compound represented by the following General Formula (Ia) (hereinafter, referred to as "compound (Ia)"), a compound represented by the following General Formula (Ib) (hereinafter, referred to as "compound (Ib)"), and a compound represented by the following General Formula (Ic) (hereinafter, referred to as "compound (Ic)"). The compound (Ia) is a compound (I) wherein $R^2$ is $COOR^3$. Alternatively, the compound (Ib) is a compound (I) wherein $R^2$ is COOH. Alternatively, the compound (Ic) is a compound (I) wherein $R^2$ is $CONR^3R^4$.

[C. 15]

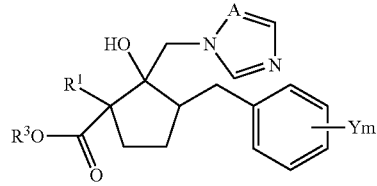

(Ia)

[C. 16]

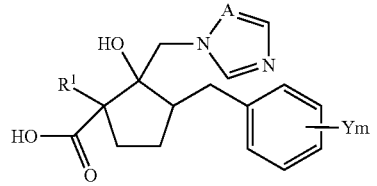

(Ib)

[C. 17]

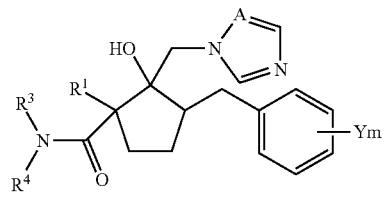

(Ic)

In the Formulae, $R^1$, $R^3$, $R^4$, Y, m, and A are the same as those described above.

As shown in FIG. 1, the first production method for the compound (I) comprises Steps 1A, 1B, 1C, and 1D. Each step may contain multiple substeps additionally. Hereinafter, each step and each substep in the first production method will be described in detail.

(3-1) Step 1A

First, Step 1A will be described briefly. Step 1A is a step of producing the compound represented by the following General Formula (VI) (hereinafter, referred to as "compound (VI)"). As shown in FIG. 1, Step 1A comprises Steps 1A1, 1A2, and 1A3.

Step 1A comprises a hydroxymethylation step of hydroxymethylating the ketoester compound represented by the following General Formula (IX) (hereinafter, referred to as "compound (IX)"), a protecting group-introducing step of introducing a protecting group to the hydroxyl group of the hydroxymethyl group-containing compound obtained (compound represented by the following General Formula (VIII), hereinafter referred to as "compound (VIII)"), and a carboxylic ester-removing step of preparing a carbonyl compound (VI) by hydrolysis and decarboxylation of the protecting group-introduced compound (compound represented by the following General Formula (VII), hereinafter referred to as "compound (VII)") (see the following Reaction Formula (1)).

[C. 18]

Reaction Formula (1)

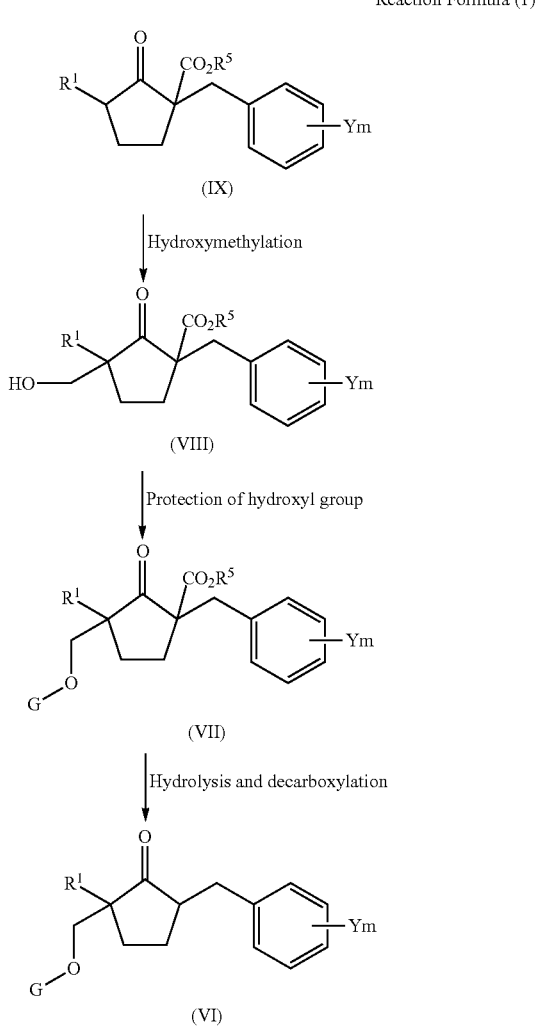

In the Formulae, Y, m, and $R^1$ are the same as those described above.

$R^5$ represents a $C_1$-$C_4$-alkyl group. Typical examples of the alkyl group of $R^5$ include methyl group, ethyl group, n-propyl group, 1-methylethyl group, 2-methylpropyl group, n-butyl group, 1,1-dimethylethyl group, and the like.

G, which represents a protecting group, is not particularly limited and examples thereof include alkoxymethyl groups such as methoxymethyl group and ethoxymethyl group; lower alkyl groups such as t-butyl group and methyl group; substituted and unsubstituted benzyl groups, and the like.

(3-1-1) Step 1A1 (Hydroxymethylation Step)

In the hydroxymethylation step of Step 1A, a method of reacting the compound (IX) with formaldehyde in solvent in the presence of a base is favorably used.

The amount of formaldehyde used with respect to 1 mole of the compound (IX) is normally 0.5 to 20 moles, preferably 0.8 to 10 moles.

Examples of the bases include, but are not limited to, alkali metal carbonate salts such as sodium carbonate and potassium carbonate; alkali metal hydroxides such as sodium hydroxide; organic bases such as triethylamine and the like. The amount of base used with respect to 1 mole of the compound (IX) is normally 0.1 to 10 moles and preferably 0.2 to 5 moles.

The reaction temperature is normally, preferably 0° C. to 250° C., more preferably 0° C. to 100° C. The reaction time is normally, preferably 0.1 hour to several days and more preferably 0.5 hours to 2 days.

The compound (IX) used may be prepared by a known method (e.g., method described in Patent Document 1).

(3-1-2) Step 1A2 (Protecting Group-Introducing Step)

Hereinafter, the step (step 1A2) of obtaining the compound (VII) by introducing a protecting group to the hydroxyl group of the compound (VIII) in Step 1A will be described.

The protecting group protecting the hydroxyl group is not particularly limited and examples thereof favorably used include alkoxymethyl groups such as methoxymethyl group and ethoxymethyl group and lower alkyl groups such as t-butyl group. These protecting groups are introduced under an acid catalysis condition. However, (a) for introduction of an alkoxymethyl group, it is preferable to protect the hydroxyl group of compound (VIII) by acetal exchange, using a formaldehyde dialkyl acetal. Alternatively, (b) for introduction of a t-butyl group, it is preferably to use a method of adding isobutene to the hydroxyl group of compound (VIII).

First, the case (a) will be described.

Examples of the acids include inorganic acids such as hydrochloric acid, phosphoric acid (including compounds giving an acid in contact with alcohol or water such as diphosphorus pentoxide), and sulfuric acid; and organic acids such as p-toluenesulfonic acid. It is preferable to use a formaldehyde dialkyl acetal in solvent or without solvent in the presence of the acid. In particular, it is more preferable to add a compound that can remove the alcohol generated, such as diphosphorus pentoxide.

The amount of formaldehyde dialkyl acetal used with respect to 1 mole of the compound (VIII) is normally 0.5 to 50 moles and preferably 0.8 to 10 moles. The amount of acid used with respect to 1 mole of the compound (VIII) is normally 0.01 to 10 moles and preferably 0.05 to 5 moles.

The reaction temperature is normally, preferably 0° C. to 250° C. and more preferably 0 to 150° C. The reaction time is normally, preferably 0.1 hour to several days and more preferably 0.5 hour to 2 days.

In the case of (b), it is preferable to make it react with isobutene in solvent in the presence of an inorganic acid such as hydrochloric acid, phosphoric acid, or sulfuric acid, or an organic acid such as p-toluenesulfonic acid or trifluoroacetic acid.

The amount of isobutene used with respect to 1 mole of the compound (VIII) is normally 0.5 to 100 moles and preferably 0.8 to 20 moles. The amount of acid used with respect to 1 mole of the compound (VIII) is normally 0.01 to 10 moles and preferably 0.05 to 5 moles.

The reaction temperature is normally, preferably 0° C. to 200° C. and more preferably 0 to 100° C. The reaction time is normally, preferably 0.1 hour to several days and more preferably 0.5 hour to 2 days.

(3-1-3) Step 1A3 (Carboxylic Ester-Removing Step)

Hereinafter, the step (step 1A3) of obtaining the compound (VI) from compound (VII) in the Step 1A will be described.

The reaction is preferably carried out in solvent in the presence of a base. The base normally used is an alkali-metal base such as sodium hydroxide or potassium hydroxide. The amount of base used with respect to 1 mole of the compound (VII) is normally 0.1 to 50 moles and preferably 0.2 to 20 moles.

The solvent normally used is water, a mixture of water and alcohol and the like, or a mixture of solvents that do not form a homogeneous layer (such as water and toluene; in this case, a phase-transfer catalyst, such as a common quaternary ammonium salt is preferably added to the reaction system).

The reaction temperature is normally, preferably 0° C. to refluxing point and more preferably room temperature to refluxing point. The reaction time is normally, preferably 0.1 hour to several days and more preferably 0.5 hour to 24 hours.

(3-2) Step 1B

Hereinafter, Step 1B in the first production method will be described below in detail. As shown in FIG. 1, Step 1B is a step of producing the compound represented by General Formula (III) (hereinafter, referred to as "compound (III)"). Step 1B comprises Steps 1B1, 1B2, and 1B3. Further as shown in FIG. 1, Step 1B2 comprises two routes: Step 1B2a and 1B2b. Hereinafter, production of the compound (III) via Steps 1B1, 1B2a, and additionally 1B3 will be described mainly as Step 1B, and the case via Step 1B2b will also be described as part of the description of Step 1B2. The compound (III) can be prepared, for example, according to Patent Document 4.

Step 1B comprises an oxirane-converting step of converting the carbonyl compound represented by the following General Formula (VI) (hereinafter, referred to as "compound (VI)") into an oxirane derivative, an azolylation step of reacting the oxirane derivative obtained (represented by the following General Formula (V); hereinafter referred to as "compound (V)") with a 1,2,4-triazole or imidazole compound represented by the following General Formula (II) (hereinafter, referred to as "compound (II)"), and a deprotecting step of deprotecting the protecting group on the azole compound obtained (represented by the following General Formula (IV); hereinafter referred to as "compound (IV)") (see the following Reaction Formula (2)).

[C. 19]

Reaction Formula (2)

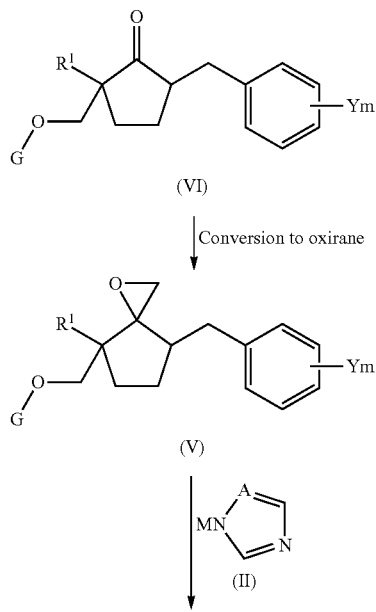

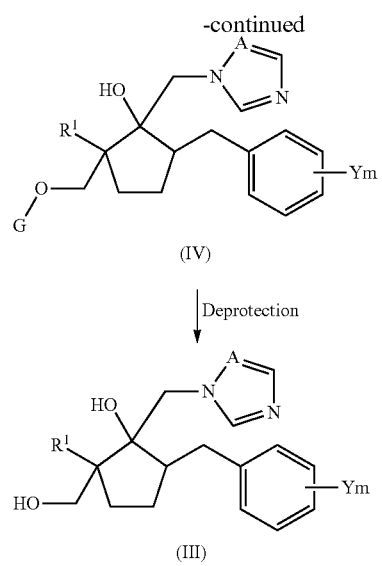

In the Formulae, Y, m, A, $R^1$, and G are the same as those described above.

M represents a hydrogen atom or an alkali metal.

(3-2-1) Step 1B1 (Oxirane-Converting Step)

The step (step 1B1) of obtaining the compound (V) by conversion of the compound (VI) to oxirane in the Step 1B will be described.

First, a method of reacting the compound (VI) with a sulfur ylide (e.g., a sulfonium methylide such as dimethylsulfonium methylide or a sulfoxonium methylide such as dimethylsulfoxonium methylide) in solvent will be described as a first synthetic method for favorable preparation of the compound (V).

The sulfonium methylide or sulfoxonium methylide for use can be prepared by reacting a sulfonium salt (e.g., trimethylsulfonium iodide or trimethylsulfonium bromide) or a sulfoxonium salt (e.g., trimethylsulfoxonium iodide or trimethylsulfoxonium bromide) with a base in solvent.

The amount of the sulfonium methylide or sulfoxonium methylide used with respect to 1 mole of the compound (VI) is preferably 0.5 to 5 moles and more preferably 0.8 to 2 moles.

The solvent for use is not particularly limited. Examples of the solvents include amides such as dimethylsulfoxide, N-methylpyrrolidone, and N,N-dimethylformamide; ethers such as tetrahydrofuran and dioxane; mixtures thereof, and the like.

The base used for generation of the sulfonium methylide or the sulfoxonium methylide is not particularly limited. Examples of the bases include metal hydrogen compound such as sodium hydride; alkali metal alkoxides such as sodium methoxide, sodium ethoxide, sodium t-butoxide, and potassium t-butoxide; and the like.

The reaction temperature and the reaction time may be determined arbitrarily, for example, according to the kinds of the solvent, compound (VI), sulfonium salt, sulfoxonium salt, and base used. The reaction temperature is favorably −100° C. to 200° C. and more preferably −50° C. to 150° C. The reaction time is preferably 0.1 hour to several days and more preferably 0.5 hour to 2 days.

Hereinafter, a method of reacting the compound (VI) with samarium diode and diiodomethane in solvent and treating the resulting mixture with a base will be described below as a second synthetic method for preparation of the compound (V).

The base for use is not particularly limited. The base for use is, for example, sodium hydroxide. The samarium diode for use can be prepared in reaction of metal samarium with 1,2-diiodoethane or diiodomethane in dehydrated solvent. The solvent for use is not particularly limited, and examples thereof include ethers such as tetrahydrofuran and the like.

The amount of base used with respect to 1 mole of the compound (VI) is not particularly limited, but normally, preferably 0.5 to 10 moles and more preferably 0.8 to 6 moles. In the case of treatment with a base, the reaction system may not be a dehydrated system and thus, for example, aqueous sodium hydroxide solution or the like may be used.

The reaction temperature and the reaction time can be determined arbitrarily according to the kinds of the solvent, compound (VI), base, and others used. The reaction temperature is preferably −100° C. to 150° C. and more preferably −50° C. to 100° C. The reaction time is preferably 0.1 hour to several days and more preferably 0.5 hour to 2 days.

(3-2-2) Step 1B2 (Azolylation Step)

Hereinafter, a step (step 1B2) of obtaining a compound (IV) by converting the compound (VI) into the azole derivative with the compound (II) in Step 1B will be described. As described above, Step 1B2 comprises two routes: Steps 1B2a and 1B2b. Hereinafter, the route of Step 1B2a will be described first.

(Step 1B2a)

In Step 1B2a, the compound (IV) is prepared by mixing the compound (V) with the compound (II) in solvent. More specifically, the compound (IV) is prepared, as a carbon-nitrogen bond is formed between the carbon atom constituting the oxirane ring of compound (V) and the nitrogen atom in 1,2,4-triazole or imidazole.

The solvent for use is not particularly limited and examples thereof include amides such as N-methylpyrrolidone, N,N-dimethylformamide, and the like.

The amount of the compound (II) used with respect to 1 mole of the compound (V) is normally, preferably 0.5 to 10 moles and more preferably 0.8 to 5 moles. A base may be added, as needed. The amount of base used with respect to 1 mole of the compound (II) is normally, preferably 0 to 5 moles (not including 0) and more preferably 0.5 to 2 moles.

The reaction temperature may be determined arbitrarily according to the solvent, base, and others used. The reaction temperature is preferably 0° C. to 250° C. and more preferably 10° C. to 150° C. The reaction time may be determined arbitrarily according to the solvent, base, and others used. The reaction time is preferably 0.1 hour to several days and more preferably 0.5 hour to 2 days.

(Step 1B2b)

Hereinafter, the case of the compound (IV) being produced via the route of Step 1B2b will be described. As described above, the compound (IV) can be prepared in stepwise reaction of the generated compound (V) with the compound (II). However, the oxirane-converting step of the first synthetic method, if carried out alone, may give oxetane derivative-like by-products and lead to reduction of the yield. For prevention of the reduction in yield, it is preferable to convert the compound (V) into the azolylated derivative, as it is generated (see the following Reaction Formula (3)).

[C. 20]

Reaction Formula (3)

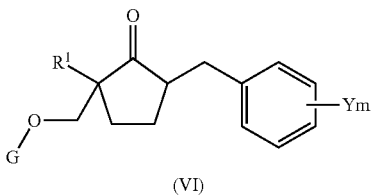

(VI)

(II)

Generation of sulfonium methylide or sulfoxonium methylide in reaction system

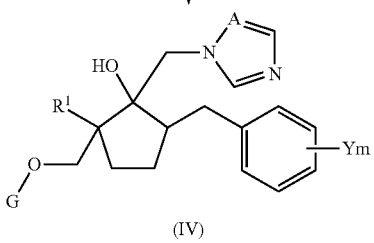

(IV)

In the Formulae, Y, m, A, $R^1$, G, and M are the same as those described above.

In this case, first, the compound (VI) and the compound (II) are dissolved in an amide bond-containing polar solvent, dimethylsulfoxide or a mixed solvent of a polar solvent and alcohol. Then, a trimethylsulfonium salt or a trimethylsulfoxonium salt is added thereto intermittently with a base, and the azolylation is carried out, as a sulfonium methylide such as dimethylsulfonium methylide or a sulfoxonium methylide such as dimethylsulfoxonium methylide and thus the compound (V) are generated in the reaction system.

The solvent for use is not particularly limited. Examples of favorable solvents include amide bond-containing polar solvents such as N-methylpyrrolidone and N,N-dimethylformamide, dimethylsulfoxide, mixed solvents of a polar solvent and alcohol, and the like. t-Butanol may be used as the alcohol.

The base used for generation of the sulfonium methylide or the sulfoxonium methylide is not particularly limited. Examples of the bases include metal hydrogen compounds such as sodium hydride, alkali metal alkoxides such as sodium methoxide, sodium ethoxide, sodium t-butoxide, potassium t-butoxide, and the like. Alkali-metal salts of 1,2,4-triazole or imidazole can also be used.

The reaction temperature may be determined arbitrarily according to the kinds of the solvent, compound (VI), sulfonium salt and sulfoxonium salt, base, and others used. The reaction temperature is preferably −100° C. to 250° C. and more preferably −50° C. to 200° C. The reaction time may be determined arbitrarily according to the kinds of the solvent, compound (VI), sulfonium salt and sulfoxonium salt, base, and others. The reaction time is preferably 0.1 hour to several days and more preferably 0.5 hour to 2 days.

The frequency of the intermittent addition of the trimethylsulfonium halide or trimethylsulfonium halide with the base is not particularly limited, if the object is achieved. The frequency is normally preferably, for example 2 to 20 times and more preferably 3 to 15 times. The total amount of the trimethylsulfonium salts or trimethylsulfoxonium salts used with respect to 1 mole of the compound (VI) is preferably 0.5 to 5 moles and more preferably 0.8 to 2 moles.

The amount of the compound (II) used with respect to 1 mole of the compound (VI) is normally, preferably 0.5 to 10 moles and more preferably 0.8 to 5 moles. A compound (II) in which M is an alkali metal is favorably used.

Detailed steps of the method of producing an azolylmethylcycloalkanol derivative, in which the azolylation is carried out, as the oxirane derivative is being generated, are described in Patent Document 5.

(3-2-3) Step 1B3 (Deprotecting Step)

Hereinafter, the step (step 1B3) of obtaining a compound (III) by deprotecting the protecting group of the compound (IV) in Step 1B will be described.

The condition favorable for deprotection varies according to the kind of the protecting group. For example if an alkoxymethyl group such as methoxymethyl group or ethoxymethyl group or a lower alkyl group such as t-butyl group or methyl group is used, it is preferably to perform deprotection in solvent under an acidic condition for example in the presence of hydrogen chloride or sulfuric acid.

The acids favorably used include hydrogen halides such as hydrogen chloride, inorganic acids such as sulfuric acid, and the like. The amount of the acid used is not particularly limited, but is normally 0.5 to 100 moles and more preferably 0.8 to 20 moles with respect to 1 mole of the compound (IV).

The reaction temperature is normally, preferably 0° C. to 200° C. and more preferably room temperature to 100° C. The reaction time is normally, preferably 0.1 hour to several days and more preferably 0.5 hour to 2 days.

(3-3) Step 1C

Hereinafter, Step 1C will be described briefly. Step 1C is a method of producing a compound (Ib) and a compound (Ia) among the azole derivatives according to the present invention. As shown in FIG. 1, Step 1C comprises four substep (steps 1C1, 1C2, 1C3, and 1C4). More specifically in Step 1C, first, the compound (Ib) is obtained in Step 1C1. There are two routes: a route (route 1) in which the compound (Ia) is prepared via Steps 1C1 to 1C2 and a route (route 2) in which the compound (Ia) is prepared via Steps 1C1 to 1C3 and additionally Step 1C4. Hereinafter, the routes 1 and 2 will be described in detail in that order.

(Route 1)

The route 1 comprises a carboxylic acid compound-forming step (oxidation step) of preparing the carboxylic acid compound by substituting a particular functional group of compound (III) with a carboxyl group and an esterification step of preparing the azole derivative represented by General Formula (Ia) above by esterifying the carboxylic acid compound.

In the present embodiment, a case where the compound represented by the following General Formula (III) is a compound having a hydroxymethyl group at the 2-position of the cyclopentane ring and the carboxylic acid compound-forming step is an oxidation step of preparing the carboxyl group by oxidation of the hydroxymethyl group will be described as an example (see Reaction Formula (4)).

[C. 21]

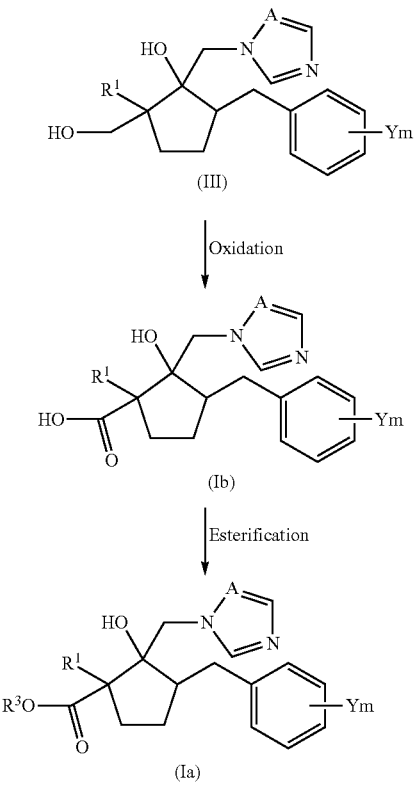

Reaction Formula (4)

In the Formulae, $R^1$, $R^3$, Y, m, and A are the same as those described above.

(3-3-1) Step 1C1 (Oxidation Step)

First, the step (step 1C1) of preparing the compound (Ib) by oxidizing the compound (III) in Step 1C will be described more in detail.

The oxidation method is not particularly limited, and examples thereof include method of using an oxidizing agent such as Jones reagent (chromic acid-sulfuric acid), a dichromate salt, pyridinium chlorochromate, pyridinium dichlorochromate, or a potassium permanganate salt, and use of Jones reagent is preferable.

The amount of oxidizing agent used with respect to 1 mole of the compound (III) is normally 0.3 to 20 moles and preferably 0.5 to 10 moles.

The solvent can be selected arbitrarily according to the kind of the oxidizing agent used. When the oxidizing agent is Jones reagent, a mixed solvent of acetone and water is used favorably.

The reaction temperature is normally, preferably −20° C. to 250° C. and more preferably −10 to 100° C. The reaction time is normally, preferably 0.1 hours to several days and more preferably 0.5 hours to 2 days.

(3-3-2) Step 1C2 (Esterification Step)

Hereinafter, the step (step 1C2) of obtaining a compound (Ia) by esterifying the compound (Ib) in Step 1C will be described.

The method of esterifying the compound (Ib) is not particularly limited and (a) a method of reacting it with diazomethane or a derivative thereof or (b) a method of reacting it with an azodicarboxylic acid derivative and a phosphine compound and then reacting the product with an alcohol represented by $R^3OH$ is used favorably.

First, method (a) will be described.

The compound (Ia) can be prepared in reaction with diazomethane or TMS diazomethane as reagent in an alcoholic solvent. TMS diazomethane is used favorably as the reagent.

The amount of TMS diazomethane used with respect to 1 mole of the compound (Ib) is normally 0.5 to 20 moles and preferably 0.8 to 10 moles.

The reaction temperature and the reaction time may be determined arbitrarily according to the reagents used. The reaction temperature is preferably −20° C. to 200° C. and more preferably −10° C. to 150° C. The reaction time is preferably 0.1 hour to several days and more preferably 0.5 hour to 2 days.

Hereinafter, method (b) will be described. The method (b) is a method of preparing the compound (Ia) using an esterification agent. Specifically, the method (b) is a method of preparing the compound (Ia) by reacting the compound (Ib) with an azodicarboxylate ester such as diethyl azodicarboxylate (DEAD) or diisopropyl azodicarboxylate (DIAD) and a phosphorus compound such as triphenylphosphine or tributylphosphine and then reacting the product with an alcohol represented by $R^3OH$. The esterification agent is preferably the combination of DEAD and triphenylphosphine.

The solvent for use is not particularly limited, and examples thereof include THF, diethyl ether, toluene, chloroform, and the like. The alcohol represented by $R^3OH$, a reaction reagent, may be used in a suitable amount, instead of using other solvents particularly.

The amount of the alcohol used can be determined arbitrarily according to the reagent and the solvent used. The amount of the alcohol used with respect to 1 mole of the compound (Ib) is preferably 0.5 to 100 moles and more preferably 0.8 to 5 moles.

The reaction temperature and the reaction time can be determined arbitrarily according to the reagents used. The reaction temperature is preferably −20° C. to 200° C. and more preferably −10° C. to 150° C. The reaction time is preferably 0.1 hour to several days and more preferably 0.5 hour to 2 days.

(Route 2)

Hereinafter, route 2 will be described in detail. As described above, the route 2 is a route of preparing the compound (Ia) from the compound (Ib) obtained in Step 1C1 via Steps 1C3 and 1C4. The Step 1C1 is identical with that in route 1 and thus, description thereof is eliminated.

The route 2 comprises a ring-closing step of preparing a compound (X) by closing the ring of the compound (Ib), which is obtained in the carboxylic acid compound-forming step of preparing a carboxylic acid compound by substituting a particular functional group of the compound (III) with a carboxyl group, with a condensing agent, and a ring-opening step of preparing an azole derivative represented by General Formula (Ia) in reaction of the compound (X) obtained (compound represented by the following General Formula (X), hereinafter referred to as "lactone compound (X)") with a metal alcoholate (see the following Reaction Formula (5)).

[C. 22]

Reaction Formula (5)

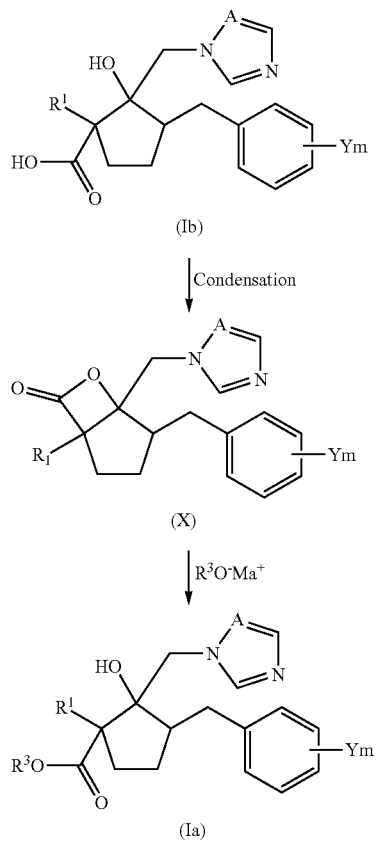

In the Formulae, Y, m, $R^1$, $R^3$, and A are the same as those described above.

(3-3-3) Step 1C3 (Condensation Step)

The step (step 1C3) of preparing the compound (X) by condensation of the compound (Ib) in Step 1A will be described.

The condensation method is not particularly limited and examples thereof include methods of using, for example, dicyclohexyl carbodiimide, 1-ethyl-3-(3-dimethylaminopropyl)carbodiimide (hereinafter, referred to as WSC), or diphenylphosphoryl azide as the condensing agent. Among the compounds above, 1-ethyl-3-(3-dimethylaminopropyl) carbodiimide is used favorably as the condensing agent. A catalyst such as hydroxybenzotriazole or dimethylaminopyridine may be used then.

The amount of the condensing agent used with respect to 1 mole of the compound (Ib) is normally 0.5 to 20 moles and preferably 0.8 to 10 moles.

The solvent can be determined arbitrarily according to the kind of the oxidizing agent used. For example when the condensing agent is WSC, THF or methylene chloride is used favorably.

The reaction temperature and the reaction time can be determined and used arbitrarily according to the reagents used. The reaction temperature is preferably −20° C. to 200° C. and more preferably −10° C. to 150° C. The reaction time is preferably 0.1 hour to several days and more preferably 0.5 hour to 2 days.

(3-3-4) Step 1C4 (Ring-Opening Step)

The step (step 1C4) of preparing the compound (Ia) in reaction of the compound (X) with a metal alcoholate in Step 1A will be described.

The metal alcoholate is a compound represented by $R^3O^-Ma^+$. $R^3$ is the same as that described above, except that it is not a hydrogen atom. $Ma^+$ represents an alkali metal, and sodium or lithium is preferable.

The metal alcoholate can be prepared in reaction of an alcohol ($R^3OH$) with an alkyl lithium, metal sodium, metal lithium, sodium hydride or the like in a solvent such as THF or diethyl ether. Particularly preferable is a method in reaction with metal lithium, and more preferable is a method in reaction with an alkyl lithium or the like.

The amount of the metal alcoholate used with respect to 1 mole of the lactone compound (X) is normally 0.5 to 20 moles and preferably 0.8 to 10 moles.

THF, diethyl ether, dioxane, or the like may be used as the solvent, but a solvent identical with that used in production of the metal alcoholate is used favorably.

The reaction temperature and the reaction time can be determined and used arbitrarily according to the reagents used. The reaction temperature is preferably −100° C. to 200° C. and more preferably −80° C. to 150° C. The reaction time is preferably 0.1 hour to several days and more preferably 0.5 hour to 2 days.

When $R^3$ is hydrogen atom, i.e., when $R^2$ is a carboxyl group, the compound (Ib) obtained in Step 1C1 is the final product and no additional step is needed after the step.

(3-4) Step 1D (Amidation Step)

Hereinafter, Step 1D will be described below. The Step 1D is a step of producing the compound (Ic) shown below by amidating the lactone compound (X) prepared in Step 1C3 (see Reaction Formula (6)). The steps to the Step 1C3 of preparing the lactone compound (X) in the first production method are the same as those described above and description thereof is eliminated.

[C. 23]

Reaction Formula (6)

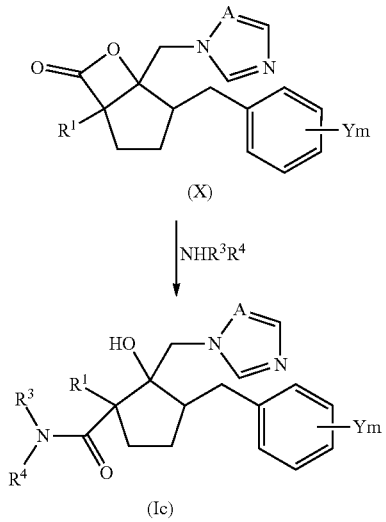

In the Formulae, $R^1$, $R^3$, $R^4$, Y, m, and A are the same as those described above.

The method of amidating the lactone compound (X) is not particularly limited and it is, for example, a method of reacting the lactone compound (X) with an amine compound represented by $R^3R^4NH$. In this way, the compound (Ic) can be prepared.

The amount of amine compounds used with respect to 1 mole of the compound (X) is normally 0.5 to 100 moles and preferably 0.8 to 80 moles.

The solvents favorably used include THF, methylene chloride, chloroform, toluene, and the like and THF is more preferable.

The reaction temperature and the reaction time can be determined and used arbitrarily according to the reagents used. The reaction temperature is preferably −20° C. to 200° C. and more preferably −10° C. to 150° C. The reaction time is preferably 0.1 hour to several days and more preferably 0.5 hour to 2 days.

(4) Second Production Method for Compound (I)

The second production method for the compound (I) will be described with reference to FIG. 1. More specifically, it is possible by the second production method for compound (I) to produce the compound represented by the following General Formula (Id) (hereinafter referred to as "compound (Id)") among the compounds (I) above. It is also possible by the second production method for compound (I) to produce a compound (Ia) and a compound (Ib) selectively. The compound (Id) is a compound (I) wherein $R^1$ is a haloalkyl group ($R^6$ in compound (Id)) and $R^2$ is $COOR^3$.

[C. 24]

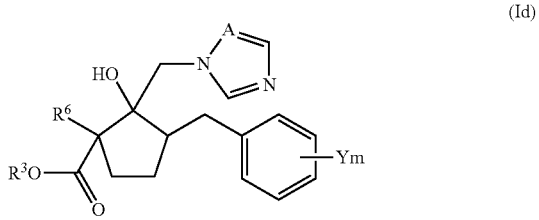

As shown in FIG. 1, the second production method for the compound (I) comprises Steps 2A, 2B, 2C, 2D, and 2E. Each step comprises multiple substeps additionally. Hereinafter, each step and each substep in the second production method will be described in detail.

(4-1) Step 2A

First, Step 2A will be described briefly. The Step 2A is a step of producing the compound represented by the following General Formula (XVI) (hereinafter referred to as "compound (XVI)"). As shown in FIG. 1, the Step 2A comprises Steps 2A1, 2A2, and 2A3.

The Step 2A comprises a hydroxyalkylating step of hydroxyalkylating the ketoester compound represented by the following General Formula (XXI) (hereinafter, referred to as "compound (XXI)"), a protecting group-introducing step of introducing a protecting group to the hydroxyl group of the hydroxyalkyl group-containing compound obtained (represented by the following General Formula (XIX); hereinafter referred to as "compound (XIX)"), and a carboxylic ester-removing step of preparing a carbonyl compound (XVI) by hydrolyzing and decarboxylating the protecting group-introduced compound (represented by the following General Formula (XVIII); hereinafter referred to as "compound (XVIII)") (see the following Reaction Formula (7)). The compound (XXI) can be obtained by benzylating the compound represented by the following General Formula (XXII).

[C. 25]

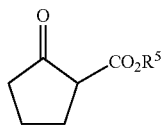
(XXII)

[C. 26]

Reaction Formula (7)

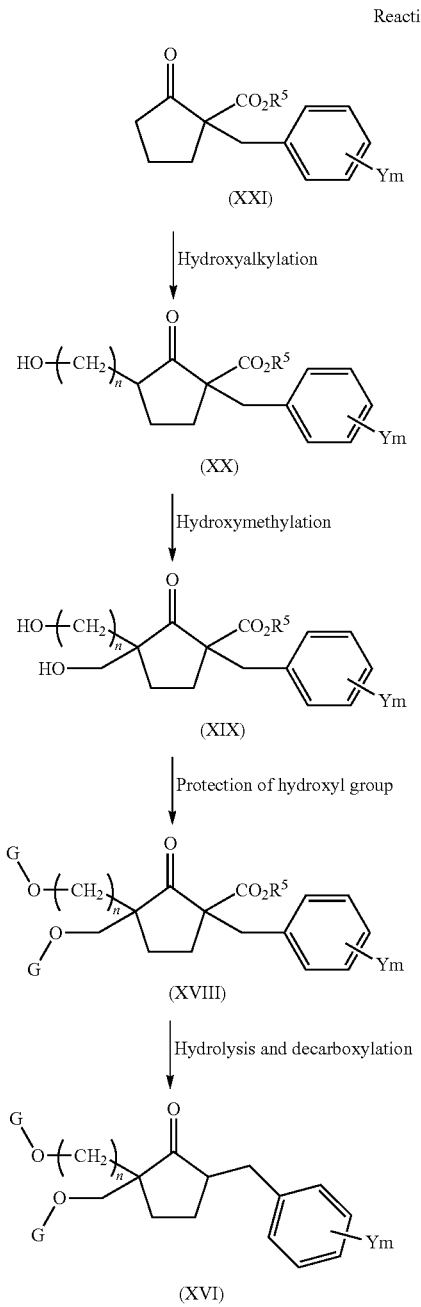

In the Formulae above, Y, m, n, G, and $R^5$ are the same as those described above.

(4-1-1) Step 2A1 (Hydroxyalkylating Step)

Hereinafter, first, the step (step 2A1) of preparing the compound (XIX) by hydroxyalkylating the compound (XXI) obtained from the compound represented by General Formula (XXII) (hereinafter, referred to as "compound (XXII)") in Step 2A will be described. The Step 2A1 comprises a step (step 2A1a) of preparing the compound (XX) by hydroxyalkylating the compound (XXI) and a step (step 2A1b) of preparing the compound (XIX) by hydroxymethylating the compound (XX) additionally. Hereinafter, Steps 2A1a and 2A1b will be described more in detail.

(Step 2A1a: First Hydroxyalkylating Step)

In Step 2A1a, the compound (XX) can be prepared in reaction of the compound (XXI) with a hydroxyalkyl halide in solvent in the presence of a base. The hydroxyl group of the hydroxyalkyl halide for use may be protected previously with a protecting group G.

The amount of hydroxyalkyl halide used with respect to 1 mole of the compound (XXI) is normally, preferably 0.5 to 20 moles and more preferably 0.8 to 10 moles.

Examples of the bases include, but are not limited to, alkali metal carbonate salts such as sodium carbonate and potassium carbonate; alkali metal hydroxides such as sodium hydroxide; organic bases such as triethylamine, and the like. The amount of base used with respect to 1 mole of the compound (XXI) is normally, preferably 0.1 to 10 moles and more preferably 0.2 to 5 moles.

The reaction temperature is normally, preferably 0° C. to 250° C. and more preferably 0 to 100° C. The reaction time is normally, preferably 0.1 hour to several days and more preferably 0.5 hour to 2 days.

The solvent is not particularly limited and examples thereof include ethers such as diethyl ether, tetrahydrofuran, and dioxane; aromatic hydrocarbons such as benzene, toluene, and xylene; water and the like. These solvents may be used as mixed, as needed. When the reaction system forms two phases, a phase-transfer catalyst, such as a common quaternary ammonium salt (e.g., benzyltriethylammonium chloride), is preferably used.

When the hydroxyalkyl group introduced is a hydroxymethyl group, the compound (XXI) is preferably reacted with formaldehyde or a formaldehyde derivative (hereinafter, referred to as formaldehyde or the like) in solvent in the presence of a base.

Examples of the formaldehyde derivatives include paraformaldehyde, 1,3,5-trioxane, formaldehyde dialkyl acetals, and the like.

The compound (XXI) for use may be a compound prepared by a known method (e.g., method described in Patent Document 1).

(Step 2A1b: Second Hydroxyalkylating Step (Hydroxymethylation Step))

The method of introducing a hydroxymethyl group in Step 2A1b may be a method of Step 2A1a wherein the hydroxyalkyl group used is a hydroxymethyl group.

When the hydroxyalkyl group introduced in the Step 2A1a is a hydroxymethyl group and bishydroxymethylation is carried out, the Step 2A1b may be eliminated. It is possible in this case to perform hydroxymethylation all at once by making the amount of hydroxymethyl halide twice larger in mole than that of the compound (XXI) in Step 2A1a. The formaldehyde or the like is favorably used twice larger in mole than the compound (XXI).

Although the case where the compound (XIX) is prepared via Steps 2A1a and then 2A1b was described above, the compound (XIX) may be prepared via Steps 2A1b and then 2A1a.

The amount of formaldehyde used with respect to 1 mole of the compound (XX) is normally, preferably 1.5 to 20 moles and more preferably 1.8 to 10 moles.

Examples of the bases include, but are not limited to, alkali metal carbonate salts such as sodium carbonate and potassium carbonate; alkali metal hydroxides such as sodium hydroxide; organic bases such as triethylamine and the like. The amount of base used with respect to 1 mole of the compound (XX) is normally, preferably 0.1 to 10 moles and more preferably 0.2 to 5 moles.

The reaction temperature is normally, preferably 0° C. to 250° C. and more preferably 0 to 100° C. The reaction time is normally, preferably 0.1 hour to several days and more preferably 0.5 hour to 2 days.

The compound (XX) for use may be a compound prepared by a known method (e.g., method described in Patent Document 1).

(4-1-2) Step 2A2 (Protecting Group-Introducing Step)

Hereinafter, the step (step 2A2) of preparing the compound (XVIII) by introducing a protecting group to the hydroxyl group of the compound (XIX) in Step 2A will be described.

The protecting group used for protection of hydroxyl group is not particularly limited. The protecting group is preferably an alkoxymethyl group such as methoxymethyl group or ethoxymethyl group, or a lower alkyl group such as t-butyl group. These protecting groups are introduced similarly to Step 1C2, except that two hydroxyl groups are protected simultaneously for example with an acetal or a ketal, and thus, description thereof is eliminated here. When two hydroxyl groups are protected simultaneously with an acetal or a ketal, the protecting groups are favorably introduced by a method of using a suitable aldehyde or ketone in the presence of an acid catalyst.

For example, when the protecting group is isopropylidene ketal, it is preferable to react the compound (XIX) with acetone or acetone dimethyl acetal, in solvent in the presence of an inorganic acid such as hydrochloric acid, phosphoric acid, or sulfuric acid, or an organic acid such as p-toluenesulfonic acid or trifluoroacetic acid.

The amount of acetone dimethyl acetal used with respect to 1 mole of the compound (XIX) is preferably 0.5 to 100 moles and more preferably, 0.8 to 20 moles. The amount of acid used with respect to 1 mole of the compound (XIX) is preferably 0.01 to 10 moles and more preferably 0.05 to 5 moles.

The reaction temperature is preferably 0° C. to 200° C. and more preferably 0° C. to 100° C. The reaction time is preferably 0.1 hour to several days and more preferably 0.5 hour to 2 days.

(4-1-3) Step 2A3 (Carboxylic Ester-Removing Step)

As a step identical with Step 1A3 in the first production method may be used as the step (step 2A3) of preparing the compound (XVI) by hydrolysis and decarboxylation of the compound (XVIII) in Step 2A, description thereof is eliminated here.

(4-2) Step 2B

Hereinafter, Step 2B in the second production method will be described below in detail. The Step 2B is a step of preparing the compound represented by the following General Formula (XIV) (hereinafter, referred to as "compound (XIV)"). As shown in FIG. 1, Step 2B comprises Steps 2B1, 2B2, and 2B3. As shown in FIG. 1, the Step 2B2 comprise two routes: Steps 2B2a and 2B2b.

The Step 2B comprises an oxirane-converting step of converting the carbonyl compound represented by the following General Formula (XVI) (hereinafter, referred to as "compound (XVI)") to an oxirane derivative, an azolylation step of reacting the oxirane derivative obtained (compound represented by the following General Formula (XVII); hereinafter referred to as "compound (XVII)") with a 1,2,4-triazole or imidazole compound represented by the following General Formula (II) ("compound (II)"), and a deprotecting step of deprotecting the protecting group of the azole compound obtained (represented by the following General Formula (XV); hereinafter referred to as "compound (XV)") (see the following Reaction Formula (8)).

[C. 27]

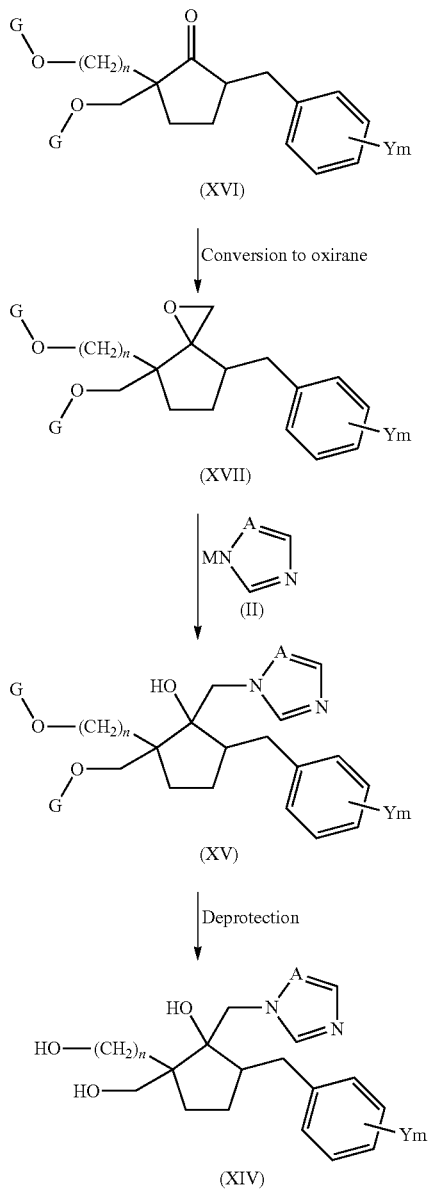

Reaction Formula (8)

In the Formulae above, definition description of Y, m, A, G, and n are the same as those described above.

(4-2-1) Step 2B1 (Oxirane-Converting Step)

The step (step 2B1) of preparing the compound (XVII) by converting the compound (XVI) to its oxirane derivative in Step 2B is identical with that in Step 1B1 described above and thus detailed description thereof is eliminated here.

(4-2-2) Step 2B2 (Azolylation Step)

Hereinafter, the step (step 2B2) of preparing the compound (XV) by converting the compound (XVII) into its azole derivative with the compound (II) in Step 2B will be described. The Step 2B2 comprises, as described above, two routes: Steps 2B2a and 2B2b.

The compound (XV) can be prepared in any route by a method similar to the Step 1B2a or 1B2b described above and thus description thereof is eliminated here.

(4-2-3) Step 2B3 (Deprotecting Step)

Hereinafter, the step (step 2B3) of preparing the compound (XIV) by deprotecting the protecting group in compound (XV) in Step 2B will be described.

Its favorable deprotection condition varies according to the kind of the protecting group. However, if an alkoxymethyl group such as methoxymethyl group or ethoxymethyl group, a lower alkyl group such as t-butyl group or methyl group, or a cyclic acetal or ketal protecting group such as methylene acetal or isopropylidene ketal is used, the deprotection is preferably carried out in solvent under an acidic condition, for example with hydrogen chloride or sulfuric acid.

Example of the acids favorably used in deprotection include hydrogen halides such as hydrogen chloride, inorganic acids such as sulfuric acid, and the like. The amount used is not particularly limited, but the amount of acid used with respect to 1 mole of the compound (XV) is normally 0.5 to 100 moles and preferably 0.8 to 20 moles.

The reaction temperature is normally, preferably 0° C. to 200° C. and more preferably room temperature to 100° C. The reaction time is normally, preferably 0.1 hour to several days and more preferably 0.5 hour to 2 days.

(4-3) Step 2C

Hereinafter, Step 2C of the second production method will be described below in detail. As shown in FIG. 1, the Step 2C is a step of producing the compound represented by the following General Formula (XIII) (hereinafter, referred to as "compound (XIII)").

The Step 2C comprises a ring-closing step of preparing the compound (XIII) by ring-closure of the hydroxyalkyl compound represented by the following General Formula (XIV) (hereinafter, referred to as "compound (XIV)") (see the following Reaction Formula (9)).

[C. 28]

Reaction Formula (9)

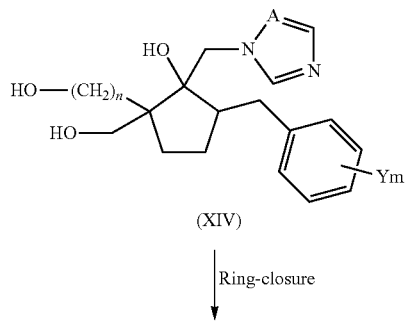

(XIV)

Ring-closure

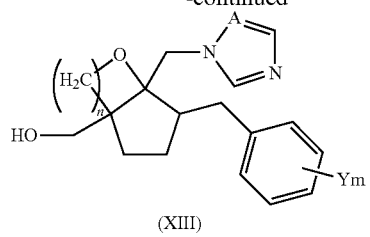

(XIII)

In the Formulae above, Y, m, n, and A are the same as those described above.

The synthetic method suitable for production of the compound (XIII) is, for example, a method of reacting the compound (XIV) with a sulfonyl chloride derivative in solvent in the presence of an excess amount of a base.

The sulfonyl chloride derivative for use may be, for example, p-toluenesulfonyl chloride or methanesulfonyl chloride. In particular, p-toluenesulfonyl chloride is used favorably.

The base is also not particularly limited. Examples of the bases favorably used include metal hydrogen compounds such as sodium hydride, alkali metal alkoxides such as sodium methoxide, sodium ethoxide, sodium t-butoxide, and potassium t-butoxide, and the like. In particular, sodium hydride can be used more favorably.

The amount of the sulfonyl chloride derivative used with respect to 1 mole of the compound (XIV) is preferably 1 to 2 moles. The amount of the base is preferably 2.5 to 10 moles and more preferably 2.8 to 6 moles.

The solvent is not particularly limited and examples of the solvents for use include amides such as N-methylpyrrolidone and N,N-dimethylformamide, ethers such as tetrahydrofuran and dioxane, dimethylsulfoxide and mixed solvents thereof. In particular, tetrahydrofuran is used favorably.

The reaction temperature may be determined arbitrarily according to the kinds of the solvent, compound (XIV), sulfonyl chloride derivative, base, and others used, but favorably −100° C. to 200° C. and more favorably −50° C. to 150° C. The reaction time may be determined arbitrarily according to the kinds of the solvent, sulfonyl chloride derivative, base, and others used, but favorably 0.1 hour to several days and more favorably 0.5 hour to 2 days.

(4-4) Step 2D

Hereinafter, Step 2D in the second production method will be described below in detail. The Step 2D is a method for producing the compound (Id) among the azole derivatives according to the present invention. As shown in FIG. 1, the Step 2D comprises three substeps (steps 2D1, 2D2, and 2D3).

In the Formulae above, $R^3$, Y, m, and A are the same as those described above. $R^6$ represents a $C_1$-$C_6$-haloalkyl group.

The Step 2D comprises a carboxylic acid compound-forming step of preparing the carboxylic acid compound (XII) represented by the following General Formula (XII) (hereinafter, referred to as "compound (XII)") by substituting a particular functional group of the compound represented by the following General Formula (XIII) (hereinafter, referred to as "compound (XIII)") with a carboxyl group, an esterification step of preparing the ester compound represented by General Formula (XI) (hereinafter, referred to as "compound (XI)") by esterifying the compound (XII) obtained, and an oxetane ring-opening step of preparing the desired compound (Id) by opening the ring of the obtained compound (XI) with an arbitrary halide ion.

In the present embodiment, a case where the following compound (XIII) is the compound having a hydroxymethyl group at the 2-position of the cyclopentane ring and the carboxylic acid compound-forming step is an oxidation step of preparing a carboxyl group by oxidizing a hydroxymethyl group will be described as an example (see Reaction Formula (10)). And, a case where the oxetane ring is opened with chloride ion is described as an example in Reaction Formula (10).

[C. 29]

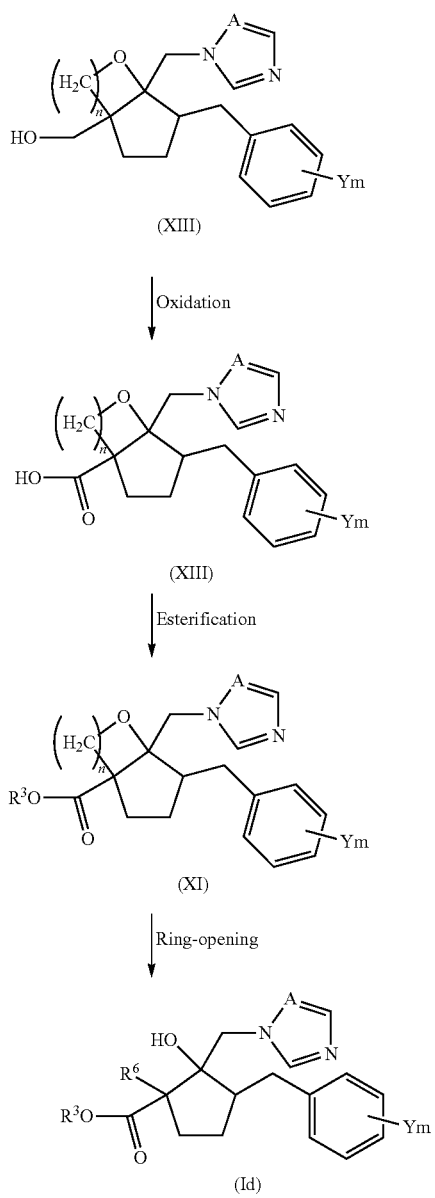

In the Formulae above, $R^3$, $R^6$, Y, m, and A are the same as those described above. n is 1 to 6. n is the same as the carbon number of the alkyl group in $R^6$.

(4-4-1) Step 2D1 (Oxidation Step)

Hereinafter, the step (step 2D1) of preparing the compound (XII) by oxidizing the compound (XIII) in the Step 2D will be first described more in detail.

The oxidation method is not particularly limited, and examples thereof include method of using an oxidizing agent such as Jones reagent (chromic acid-sulfuric acid), a dichromate salt, pyridinium chlorochromate, pyridinium dichlorochromate, or a potassium permanganate salt, and use of the Jones reagent is preferable.

The amount of oxidizing agent used with respect to 1 mole of the compound (XIII) is normally 0.3 to 20 moles, preferably 0.5 to 10 moles.

The solvent may be determined arbitrarily according to the kind of the oxidizing agent. When the oxidizing agent is Jones reagent, a mixed solvent of acetone and water is used favorably.

The reaction temperature is normally, preferably −20° C. to 250° C. and more preferably −10 to 100° C. The reaction time is normally, preferably 0.1 hour to several days and more preferably 0.5 hour to 2 days.

(4-4-2) Step 2D2 (Esterification Step)

Hereinafter, the step (step 2D2) of preparing the compound (XI) by esterifying compound (XII) in Step 2D will be described.

The method of esterifying the compound (XII) is not particularly limited and (a) a method of reacting it with diazomethane or a derivative thereof or (b) a method of reacting it with an azodicarboxylic acid derivative and a phosphine compound and then reacting the product with an alcohol represented by $R^3OH$ is used favorably.

First, method (a) will be described.

The compound (XI) can be prepared in a reaction using diazomethane or TMS diazomethane as reagent and adding a base to the reagent in ether-based solvent. The reagent for use is favorably TMS diazomethane.

The amount of the TMS diazomethane used with respect to 1 mole of the compound (XII) is normally 0.5 to 20 moles and preferably 0.8 to 10 moles.

The reaction temperature and the reaction time can be determined arbitrarily according to the reagents used. The reaction temperature is preferably −20° C. to 200° C. and more preferably −10° C. to 150° C. The reaction time is preferably 0.1 hour to several days and more preferably 0.5 hours to 2 days.

Hereinafter, method (b) will be described. The method (b) is a method of producing the compound (XI), using an esterification agent. More specifically, the method (b) is a method of producing the compound (XI) by reacting the compound (XII) with an azodicarboxylate ester such as diethyl azodicarboxylate (DEAD) or diisopropyl azodicarboxylate (DIAD) and a phosphorus compound such as triphenylphosphine or tributylphosphine and additionally reacting the product with an alcohol represented by $R^3OH$. The esterification agent for use is preferably a combination of DEAD and triphenylphosphine.

The solvent for use is not particularly limited, and examples thereof include THF, diethyl ether, toluene, chloroform, and the like. The alcohol represented by $R^3OH$, a reaction reagent, may be used in a suitable amount, instead of using other solvent particularly.

The amount of the alcohol used may be determined arbitrarily according to the solvent used. The amount of the alcohol used with respect to 1 mole of the compound (XII) is preferably 0.5 to 100 moles and more preferably 0.8 to 5 moles.

The reaction temperature and the reaction time can be determined arbitrarily according to the reagents used. The reaction temperature is preferably −20° C. to 200° C. and more preferably −10° C. to 150° C. The reaction time is preferably 0.1 hour to several days and more preferably 0.5 hour to 2 days.

(4-4-3) Step 2D3 (Ring-Opening Step)

Hereinafter, the step (step 2D3) of preparing the compound (Id) by opening the oxetane ring of the compound (XI) in Step 2D will be described in detail.

The compound (Id) can be prepared favorably by mixing a halogen acid to the compound (XI) in solvent, thus allowing ring-opening of the oxetane ring in the compound (XI) and generating a halogenated methyl group and a tertiary hydroxyl group.

The halogen acid is, for example, hydrogen chloride, hydrogen bromide, hydrogen fluoride, or hydrogen iodide. In particular, hydrogen chloride or hydrogen bromide is used favorably. The halogen acid may be introduced as a gas or as it is dissolved in a solvent. The compound (Id) may be prepared from the compound (XI), as the halogen acid is generated in the reaction system, by addition, to a halide salt, of an acid different in kind (such as toluenesulfonic acid, methanesulfonic acid, sulfuric acid, or the like).

The solvent is not particularly limited and examples thereof include amides such as N-methylpyrrolidone and N,N-dimethylformamide, alcohols such as methanol and ethanol, ethers such as tetrahydrofuran and dioxane, water, and the like. In particular, use of N,N-dimethylformamide is preferable.

The reaction temperature may be determined arbitrarily according to the solvent, base, and others used, but is favorably −20° C. to 250° C. and more favorably 50° C. to 80° C. The reaction time may be determined arbitrarily according to the solvent, base, and others used, but is favorably 0.1 hour to several days and more favorably 1 hour to 2 days.

When $R^3$ is a hydrogen atom, i.e., when $R^2$ is a carboxyl group, the compound (XII) obtained in Step 2D1 may be subjected to the ring-opening step without esterification.

(4-5) Step 2E (Ring-Opening Step)

Step 2D in the second production method described above is a method of preparing the compound (Id) in which $R^1$ is a halogen atom-substituted alkyl group, by opening the ring of compound (XIII) with an acid different in kind from the halogen acid or halide salt. Hereinafter, the method of preparing the compound (Ia) wherein $R^1$ is an unsubstituted alkyl group in the second production method will be described below as Step 2E.

As shown in FIG. 1, the Step 2E comprises a ring-opening step of preparing the compound (III) by reductive ring-opening of the compound (XIII). The reductive ring-opening of the compound (XIII) can be carried out, for example, using a metal hydride. More specifically, a metal hydride such as lithium aluminum hydride or sodium borohydride is favorably used. These hydrides may be used, as mixed with aluminum chloride.

However, the step of preparing the compound (Ia) from the compound (III) obtained in the Step 2E is the same as Step 1C in the first production method and was already described, and thus, description thereof is eliminated here.

3. Agricultural or Horticultural Chemical Agents and Industrial Material-Protecting Agents Hereinafter, usefulness of the agricultural or horticultural chemical agents and the industrial material-protecting agents (hereinafter, referred to also as "agricultural or horticultural chemical agents and others") containing the azole derivative according to the present invention (see compound (I)) as an active ingredient will be described.

(1) Plant Disease-Controlling Activity

The agricultural or horticultural chemical agents containing the compound (I) as an active ingredient show controlling activity to a wide variety of plant diseases. Examples of applicable diseases are those described below:

Soybean rust (*Phakopsora pachyrhizi, Phakopsora meibomiae*), rice blast (*Pyricularia grisea*), rice brown spot (*Cochliobolus miyabeanus*), rice bacterial leaf blight (*Xanthomonas oryzae*), rice sheath blight (*Rhizoctonia solani*), rice stem rot (*Helminthosporiumsigmoideun*), rice bakanae disease (*Gibberella fujikuroi*), rice seedling blight (*Pythium aphanidermatum*), apple powdery mildew (*Podosphaera leucotricha*), apple black spot (*Venturia inaequalis*), apple blossom blight (*Monilinia mali*), apple alternaria blotch (*Alternaria alternata*), apple valsa canker (*Valsa mali*), pear black spot (*Alternaria kikuchiana*), pear powdery mildew (*Phyllactinia pyri*), pear rust (*Gymnosporangium asiaticum*), pear scab (*Venturia nashicola*), grape powdery mildew (*Uncinula necator*), grape downy mildew (*Plasmoparaviticola*), grape ripe out (*Glomerella cingulata*), barley powdery mildew (*Erysiphe graminis* f. sp *hordei*), barley stem rust (*Puccinia graminis*), barley stripe rust (*Puccinia striiformis*), barley stripe (*Pyrenophora graminea*), barley scald (*Rhynchosporium secalis*), wheat powdery mildew (*Erysiphe graminis* f. sp *tritici*), wheat leaf rust (*Puccinia recondita*), wheat stripe rust (*Puccinia striiformis*), wheat eye spot (*Pseudocercosporella herpotrichoides*), wheat *fusarium* blight (*Fusarium graminearum, Microdochium nivale*), wheat glume blotch (*Phaeosphaeria nodorum*), wheat leaf blight (*Septoria tritici*), gourd powdery mildew (*Sphaerotheca fuliginea*), gourd anthracnose (*Colletotrichum lagenarium*), cucumber downy mildew (*Pseudoperonospora cubensis*), cucumber damping-off (*Phytophthora capsici*), tomato powdery mildew (*Erysiphe cichoracearum*), tomato early blight (*Alternaria solani*), eggplant powdery mildew (*Erysiphe cichoracearum*), strawberry powdery mildew (*Sphaerotheca humuli*), tobacco powdery mildew (*Erysiphe cichoracearum*), sugar beet cercospora leaf spot (*Cercospora beticola*), corn smut (*Ustilag maydis*), stone fruit brown rot (*Monilinia fructicola*), gray mold of various crop plants (*Botrytis cinerea*), sclerotinia rot (*Sclerotinia sclerotiorum*), and the like. In particular among them, they are more effective than a commercially available chemical Metconazole described in Patent Document 1 to important diseases of wheat: wheat leaf blight (*Septoria tritici*) and wheat leaf rust (*Puccinia recondita*) (see Test Examples 1 and 2 below).

Examples of applicable plants include wild plants, plant cultivars, plant and plant cultivars obtained by traditional breeding such as crossbreeding or protoplast fusion, and genetically engineered plants and plant cultivars obtained by gene manipulation. Examples of the genetically engineered plants and plant cultivars include herbicide-resistance crops, bug-resistant crops containing insecticidal protein-producing gene, disease-resistant crops containing a gene producing disease-resistance-inducing substance, flavor-improved crops, yield-improved crops, shelf life-improved crops, yield-improved crops, and the like. Typical examples of the genetically engineered plant cultivars include those under the registered trade names of ROUNDUP READY, LIBERTY LINK, CLEARFIELD, YIELDGARD, HERCULEX, BOLLGARD, and others.

(2) Plant Growth-Promoting Activity

The agricultural or horticultural chemical agents containing the compound (I) as an active ingredient show growth-regulating activity to a wide variety of crops and horticultural plants, increasing their yields and improving their qualities. Examples of these crop plants includes the following plants:

Wheats such as wheat, barley, and oat, rice, rapeseed, sugar cane, corn, maize, soy bean, pea, peanut, sugar beet, cabbage, garlic, Chinese radish, carrot, apple, pear, citrus fruits such as mandarin orange, orange, and lemon, peach, cherry, avocado, mango, papaya, red pepper, cucumber, melon, strawberry, tobacco, tomato, eggplant, lawn, chrysanthemum, azalea, and other decorative plants.

(3) Industrial Material-Protecting Activity

The industrial material-protecting agents containing the compound (I) as an active ingredient show an advantageous effect of protecting industrial materials from a wide variety of hazardous microorganisms that erode them. Examples of these microorganisms include the followings:

Paper and pulp-degrading microorganisms (including slime-forming microbes) such as *Aspergillus* sp., *Trichoderma* sp., *Penicillium* sp., *Geotrichum* sp., *Chaetomium* sp., *Cadophora* sp., *Ceratostomella* sp., *Cladosporium* sp., *Corticium* sp., *Lentinus* sp., *Lenzites* sp., *Phoma* sp., *Polysticus* sp., *Pullularia* sp., *Stereum* sp., *Trichosporium* sp., *Aerobacter* sp., *Bacillus* sp., *Desulfovibrio* sp., *Pseudomonas* sp. *Flavobacterium* sp., and *Micrococcus* sp.; fiber-degrading microorganisms such as *Aspergillus* sp., *Penicillium* sp., *Chaetomium* sp., *Myrothecium* sp., *Curvularia* sp., *Gliomastix* sp., *Memnoniella* sp., *Sarcopodium* sp., *Stachybotrys* sp., *Stemphylium* sp., *Zygorhynchus* sp., *Bacillus* sp., and *Staphylococcus* sp.;

wood-degrading microbes such as *Tyromyces palustris, Coriolus versicolor, Aspergillus* sp., *Penicillium* sp., *Rhizopus* sp., *Aureobasidium* sp., *Gliocladium* sp., *Cladosporium* sp., *Chaetomium* sp., and *Trichoderma* sp.;

leather-degrading microorganisms such as *Aspergillus* sp., *Penicillium* sp., *Chaetomium* sp., *Cladosporium* sp., *Mucor* sp., *Paecilomyces* sp., *Pilobus* sp., *Pullularia* sp., *Trichosporon* sp., and *Tricothecium* sp.;

rubber and plastic-degrading microorganisms such as *Aspergillus* sp., *Penicillium* sp., *Rhizopus* sp., *Trichoderma* sp., *Chaetomium* sp., *Myrothecium* sp., *Streptomyces* sp., *Pseudomonas* sp., *Bacillus* sp., *Micrococcus* sp., *Serratia* sp., *Margarinomyces* sp., and *Monascus* sp.; and paint-degrading microorganisms such as *Aspergillus* sp., *Penicillium* sp., *Cladosporium* sp., *Aureobasidium* sp., *Gliocladium* sp., *Botryodiplodia* sp., *Macrosporium* sp., *Monilia* sp., *Phoma* sp., *Pullularia* sp., *Sporotrichum* sp., *Trichoderma* sp., *Bacillus* sp., *Proteus* sp., *Pseudomonas* sp., and *Serratia* sp.

(4) Formulations (Agricultural or Horticultural Chemical Agents)

The agricultural or horticultural chemical agent containing the compound (I) as an active ingredient may contain various compound in addition to the compound (I). For example, the agricultural or horticultural chemical agent containing the compound (I) as an active ingredient may contain a solid carrier, a liquid carrier, a surfactant, and other formulation aids additionally. The agricultural or horticultural chemical agent containing the compound (I) as an active ingredient may be in any shape and examples thereof include powder, wettable powder, granule, emulsion, and the like.

The agricultural or horticultural chemical agent preferably contains the compound (I) as active ingredient in an amount of 0.1 to 95 wt % with respect to the total amount of the agricultural or horticultural chemical agent. The compound (I) as active ingredient is more preferably contained in an amount of 0.5 to 90 wt % and further more preferably 2 to 80 wt %.

The carriers, diluents, and surfactants used as formulation aides include the followings: Examples of the solid carriers include talc, kaolin, bentonite, diatomaceous earth, white carbon, clay, and the like. Examples of the liquid diluents include water, xylene, toluene, chlorobenzene, cyclohexane, cyclohexanone, dimethylsulfoxide, dimethylformamide, alcohol, and the like. The surfactant is favorably used according to its effect. For example, if the surfactant is an emulsifier, examples thereof for use include polyoxyethylene alkyl aryl ethers, polyoxyethylene sorbitan monolaurate, and the like; alternatively if the surfactant is a dispersant, examples thereof for use include lignin sulfonate salts, dibutylnaphthalene sulfonate salts, and the like; yet alternatively if it is a wetting agent, examples thereof for use include alkylsulfonate salts, alkylphenylsulfonate salts, and the like.

The formulation may be used as it is or as it is diluted to a particular concentration with a diluent such as water. If it is used as diluted, the concentration of the compound (I) in spray solution is desirably in the range of 0.001 to 1.0%.

The application amount of the compound (I) is preferably 20 to 5000 g, and more preferably 50 to 2000 g, to 1 ha of an agricultural or horticultural land, such as field, farm, orchard, or green house. The concentration and the amount of application vary according to the shape of formulation, period of application, application method, application site, crop applied, and the like, and thus, may be adjusted, independently of the range above.

In addition, the agricultural or horticultural chemical agent according to the present invention may be used as a composition increased in the activity as an agricultural or horticultural chemical agent, as the compound (I) is mixed with other active ingredients, such as fungicides, insecticides, miticides, or herbicides, exemplified below:

<Antimicrobial Substances>

Acibenzolar-S-methyl, 2-phenylphenol (OPP), azaconazole, azoxystrobin, amisulbrom, bixafen, benalaxyl, benomyl, benthiavalicarb-isopropyl, bicarbonate, biphenyl, bitertanol, blasticidin-S, borax, bordeaux solution, boscalid, bromuconazole, bronopol, bupirimate, sec-butylamine, calcium polysulfide, captafol, captan, carbendazim, carboxin, carpropamid, quinomethionate, chloroneb, chloropicrin, chlorothalonil, chlozolinate, cyazofamid, cyflufenamid, cymoxanil, cyproconazole, cyprodinil, dazomet, dekalb, dichlofluanid, diclocymet, diclomezine, dicloran, diethofencarb, difenoconazole, diflumetorim, dimethomorph, dimethoxystrobin, diniconazole, dinocap, diphenylamine, dithianon, dodemorph, dodine, edifenphos, epoxiconazole, ethaboxam, ethoxyquin, etridiazol, enestroburin, famoxadone, fenamidone, fenarimol, fenbuconazole, fenfuram, fenhexamid, fenoxanil, fenpiclonil, fenpropidine, fenpropimorph, fentin, ferbam, ferimzone, fluazinam, fludioxonil, flumorph, fluoromide, fluoxastrobin, fluquinconazole, flusilazole, flusulfamide, flutolanil, flutriafol, folpet, fosetyl-aluminum, fuberidazole, furalaxyl, furametpyr, fluopicolide, fluopyram, guazatine, hexachlorobenzene, hexaconazole, hymexazol, imazalil, imibenconazole, iminoctadine, ipconazole, iprobenfos, iprodione, iprovalicarb, isoprothiolane, isopyrazam, isotianil, kasugamycin, copper derivatives such as copper hydroxide, copper naphthenate, copper oxychloride, copper sulfate, copper oxide, and oxine-copper; kresoxim-methyl, mancocopper, mancozeb, maneb, mandipropamid, mepanipyrim, mepronil, metalaxyl, metconazole, metiram, metominostrobin, mildiomycin, myclobutanil, nitrothal-isopropyl, nuarimol, ofurace, oxadixyl, oxolinic acid, oxpoconazole, oxycarboxin, oxytetracycline, pefurazoate, orysastrobin, penconazole, pencycuron, penthiopyrad, pyribencarb, fthalide, picoxystrobin, piperalin, polyoxin, probenazole, prochloraz, procymidone, propamocarb, propiconazole, propineb, proquinazid, prothioconazole, pyraclostrobin, pyrazophos, pyrifenox, pyrimethanil, pyroquilone, quinoxyfen, quintozene, silthiofam, simeconazole, spiroxamine, sulfur and sulfur formulations, tebuconazole, tecloftalam, tecnazene, tetraconazole, thiabendazole, thiflu-zamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, amisulbrom, sedaxane, flutianil, valiphenal, ametoctradin, dimoxystrobin, metrafenone, hydroxyisoxazole, methasulfocarb, and the like.

<Insecticides/Miticides/Nematicides>

Abamectin, acephate, acrinathrin, alanycarb, aldicarb, allethrin, amitraz, avermectin, azadirachtin, azamethiphos, azinphos-ethyl, azinphos-methyl, azocyclotin, *Bacillus* films, *Bacillus subtilis, Bacillus thuringiensis*, bendiocarb, benfuracarb, bensultap, benzoximate, bifenazate, bifenthrin, bioallethrin, bioresmethrin, bistrifluron, buprofezin, butocarboxim, butoxycarboxim, cadusafos, carbaryl, carbofuran, carbosulfan, cartap, CGA 50439, chlordane, chlorethoxyfos, chlorfenapyr, chlorfenvinphos, chlorfluazuron, chlormephos, chlorpyrifos, chlorpyrifos-methyl, chromafenozide, clofentezine, clothianidin, chlorantraniliprole, coumaphos, cryolite, cyanophos, cycloprothrin, cyfluthrin, cyhalothrin, cyhexatin, cypermethrin, cyphenothrin, cyromazine, cyazypyr, cyenopyrafen, DCIP, DDT, deltamethrin, demeton-S-methyl, diafenthiuron, diazinon, dichlorophen, dichloropropene, dichlorvos, dicofol, dicrotophos, dicyclanil, diflubenzuron, dimethoate, dimethylvinphos, dinobuton, dinotefuran, emamectin, endosulfan, EPN, esfenvalerate, ethiofencarb, ethion, ethiprole, ethofenprox, ethoprophos, ethoxazole, famphur, fenamiphos, fenazaquin, fenbutatin oxide, fenitrothion, fenobucarb, fenothiocarb, fenoxycarb, fenpropathrin, fenpyroximate, fenthion, fenvalerate, fipronil, flonicamid, fluacrypyrim, flucycloxuron, flucythrinate, flufenoxuron, flumethrin, fluvalinate, flubendiamide, formetanate, fosthiazate, halfenprox, furathiocarb, halofenozide, gamma-HCH, heptenophos, hexaflumuron, hexythiazox, hydramethylnon, imidacloprid, imiprothrin, indoxacarb, isoprocarb, isoxathion, lufenuron, malathion, mecarbam, metam, methamidophos, methidathion, methiocarb, methomyl, methoprene, metosulam, methoxyfenozide, metolcarb, milbemectin, monocrotophos, naled, nicotine, nitenpyram, novaluron, noviflumuron, omethoate, oxamill, oxydemeton-methyl, parathion, permethrin, phenthoate, phorate, phosalone, phosmet, phosphamidon, phoxim, pirimicarb, pirimiphos-methyl, profenofos, propoxur, prothiofos, pymetrozine, pyraclofos, pyrethrin, pyridaben, pyridalyl, pyrimidifen, pyriproxyfen, pyrifluquinazon, pyriprole, quinalphos, silafluofen, spinosad, spirodiclofen, spiromesifen, spirotetramat, sulfluramid, sulfotep, SZI-121, tebufenozide, tebufenpyrad, tebupirimfos, teflubenzuron, tefluthrin, temephos, terbufos, tetrachlorvinphos, thiacloprid, thiamethoxam, thiodicarb, thiofanox, thiometon, tolfenpyrad, tralomethrin, tralopyril, triazamate, triazophos, trichlorfon, triflumuron, vamidothion, valiphenal, XMC, xylylcarb, imicyafos, lepimectin, and the like.

<Plant Growth-Regulating Agents>

Ancymidol, 6-benzylaminopurine, paclobutrazol, diclobutrazol, uniconazole, methylcyclopropene, mepiquat chloride, ethephon, chlormequat chloride, inabenfide, pro- hexadione and the salts thereof, trinexapac-ethyl, and the like. Plant hormones such as jasmonic acid, brassinosteroids, gibberellins, and the like.

(Industrial Material-Protecting Agents)

Alternatively, the industrial material-protecting agent containing the compound (I) as an active ingredient may contain various components in addition to the compound (I). The industrial material-protecting agent containing the compound (I) as an active ingredient can be used, as it is dissolved or dispersed in a suitable liquid carrier or as it is mixed with a solid carrier. The industrial material-protecting agent containing the compound (I) as an active ingredient may contain, as needed, emulsifiers, dispersants, spreading agents, penetrants, wetting agents, stabilizers, and the like additionally. In addition, the industrial material-protecting agent containing the compound (I) as an active ingredient may be in any shape and examples thereof include wettable powder, powder, granule, tablet, paste, suspension, spray, and the like. The industrial material-protecting agent containing the compound (I) as an active ingredient may contain other fungicides, insecticides, antidegradants, and others additionally.

The liquid carrier is not particularly limited, if it is inert to the active ingredient. Examples of the liquid carriers include water, alcohols (e.g., methyl alcohol, ethyl alcohol, ethylene glycol, cellosolve, etc.), ketones (e.g., acetone, methylethylketone, etc.), ethers (e.g., dimethyl ether, diethyl ether, dioxane, tetrahydrofuran, etc.), aromatic hydrocarbons (e.g., benzene, toluene, xylene, methylnaphthalene, etc.), aliphatic hydrocarbons (e.g., gasoline, kerosene, kerosene, machine oil, fuel oil, etc.), acid amides (e.g., dimethylformamide, N-methylpyrrolidone, etc.), halogenated hydrocarbons (e.g., chloroform, carbon tetrachloride, etc.), esters (e.g., ethyl acetate, fatty acid glycerol esters, etc.), nitriles (e.g., acetonitrile, etc.), dimethylsulfoxide, and the like.

Examples of the solid carriers for use include fine powders or granules of kaolin clay, bentonite, acid clay, pyrophyllite, talc, diatomaceous earth, calcite, urea, ammonium sulfate, and the like.

Examples of the emulsifiers and dispersants for use are surfactants such as soaps, alkylsulfonic acids, alkylarylsulfonic acids, dialkylsulfosuccinic acids, quaternary ammonium salts, oxyalkylamines, fatty acid esters, polyalkyleneoxide derivatives, anhydrosorbitol derivatives, and the like.

When the compound (I) is contained in a formulation as an active ingredient, the content thereof varies according to the shape of formulation and the purpose of application, but is preferably 0.1 to 99.9 wt % with respect to the total amount of the formulation. During actual use, the application concentration is preferably adjusted normally to 0.005 to 5 wt % and preferably 0.01 to 1 wt %, for example by addition of a solvent, a diluent, or a filler.

The agricultural or horticultural chemical agent and the industrial material-protecting agent may contain as active ingredients multiple compounds included in the scope of the compounds (I).

As described above, the azole derivatives represented by compound (I) show favorable sterilizing activity to many plant disease-causing microbes. The agricultural or horticultural disease-controlling agent containing an azole derivative represented by compound (I) as an active ingredient is safer to human and animals and superior in handling stability, and also shows high controlling activity to a wide variety of plant diseases. The agricultural or horticultural disease-controlling agent containing the azole derivative represented by compound (I) can prevent damages caused by plant diseases for example of straw and leave and also of seed by seed treatment. Seeds treated with the agricultural or horticultural disease-controlling agent containing the azole derivative represented by compound (I) are also included in the scope of the present invention.

As the compound (I) contains a 1,2,4-triazolyl group or an imidazolyl group, it forms an acid adduct salt or a metal complex with an inorganic or organic acid. The compound (I) may be used in the form of the acid adduct salt or the metal complex.

The compound (I) has at least 3 asymmetric carbons. Thus, it may be a mixture of the stereoisomers (enantiomers or diastereomers) or one of the stereoisomers, depending on the composition. Thus, at least one of these stereoisomers can be used as the active ingredient of the agricultural or horticultural chemical agents and others.

(Additional Remark)

The present invention is not limited to the embodiments described above and various modification is possible within the scope specified by the Claims. In other words, embodiments that can be obtained in combination of technical means appropriately modified within the scope specified by the Claims are also included in the technical scope of the present invention.

EXAMPLES

Hereinafter, the present invention will be described specifically with reference to Preparative Examples, Formulation Examples, and Test Examples. The present invention is not limited to the following Preparative Examples, Formulation Examples, and Test Examples, unless it is outside the scope of the Invention.

Preparative Example 1

Preparation of (1SR,2SR,3RS)-3-(4-chlorobenzyl)-2-hydroxy-1-methyl-2-(1H-1,2,4-triazol-1-ylmethyl)-1-cyclopentanecarboxylic acid (compound (I-1): $R^1$=$CH_3$, $R^2$=COOH, A=N, Ym=4-Cl, configuration: CC)

Chromic acid 6.03 g was dissolved in water 11.3 ml and conc. sulfuric acid 5.2 ml was added dropwise thereto gradually. The salt formed was dissolved by addition of water 1.8 ml, to give a Jones reagent. (1RS,2SR,3RS)-3-(4-chlorobenzyl)-2-hydroxy-1-methyl-2-(1H-1,2,4-triazol-1-ylmethyl)-1-cyclopentanemethanol (compound (III-1): $R^1$=$CH_3$, A=N, Ym=4-Cl, configuration: CC) prepared by a known method (e.g., JP-A No. H05-271197) 1.44 g was dissolved in acetone 45 ml; the Jones reagent prepared above 3.3 ml was added thereto; and the mixture was agitated at room temperature for 1.5 hours.

After the reaction, isopropyl alcohol was added thereto; the green insoluble matter generated was separated by filtration and washed with acetone; the filtrate and the washing water were combined; and the solution was neutralized with aqueous potassium hydroxide solution and extracted with chloroform. The organic layer was washed with saturated aqueous sodium chloride solution and water, and dried over anhydrous sodium sulfate. The solvent was removed by distillation and the residue was purified by silica gel column chromatography, to give the title compound.

Yield: 52.6%

$^1$H-NMR (250 MHz, CDCl$_3$) δ=0.75 (3H, s), 1.45-1.85 (3H, m), 2.04-2.18 (1H, m), 2.28-2.45 (1H, m), 2.60-2.85 (2H, m), 4.21 (1H, d, J=14.0 Hz), 4.68 (1H, d, J=14.0 Hz), 7.13 (2H, d, J=8.6 Hz), 7.24 (2H, d, J=8.6 Hz), 8.00 (1H, s), 8.25 (1H, s).

Preparative Example 2

Preparation of (1RS,2SR,3RS)-3-(4-chlorobenzyl)-2-hydroxy-1-methyl-2-(1H-1,2,4-triazol-1-ylmethyl)-1-cyclopentanecarboxylic acid (compound (I-131): $R^1$=$CH_3$, $R^2$=COOH, A=N, Ym=4-Cl, configuration: TC)

The title compound was prepared by a method similar to that for preparation of the compound (I-1) described above, except that (1SR,2SR,3RS)-3-(4-chlorobenzyl)-2-hydroxy-1-methyl-2-(1H-1,2,4-triazol-1-ylmethyl)-1-cyclopentanemethanol (compound number: (III-2): $R^1$=$CH_3$, A=N, Ym=4-Cl, configuration: TC) was used as the raw material, replacing (1RS,2SR,3RS)-3-(4-chlorobenzyl)-2-hydroxy-1-methyl-2-(1H-1,2,4-triazol-1-ylmethyl)-1-cyclopentanemethanol (compound number: (III-1).

Yield: 37.1%

$^1$H-NMR (400 MHz, CDCl$_3$) δ=1.43 (3H, s), 1.60-1.78 (2H, m), 1.85-1.98 (1H, m), 2.28-2.46 (2H, m), 2.78 (1H, dd, J=13.8, 9.1 Hz), 2.87 (1H, dd, J=13.8, 5.7 Hz), 4.13 (1H, d, J=14.3 Hz), 4.38 (1H, d, J=14.3 Hz), 7.18 (2H, d, J=8.5 Hz), 7.27 (2H, d, J=8.5 Hz), 7.93 (1H, s), 8.30 (1H, 5).

Preparative Example 3

Preparation of methyl-(1RS,2SR,3RS)-3-(4-chlorobenzyl)-2-hydroxy-1-methyl-2-(1H-1,2,4-triazol-1-ylmethyl)cyclopentanecarboxylate (compound (I-132): $R^1$=$CH_3$, $R^2$=$COOCH_3$, A=N, Ym=4-Cl, configuration: TC)

Under argon atmosphere, compound (I-131) (0.352 mmol) was suspended in dehydrated methanol 1.2 ml; dehydrated benzene 4.3 ml was added thereto for solubilization; 2.0 M solution of trimethylsilyl diazomethane in hexane (0.422 mmol) was added dropwise over 2 minutes. After heating and foaming subsided, the mixture was agitated at room temperature for 1 hour. After the reaction, the yellow homogeneous solution was distilled for removal of the solvent under reduced pressure, and the residue obtained was separated and purified by silica gel column chromatography, to give the title compound.

Yield: 80%

$^1$H-NMR (400 MHz, CDCl$_3$, TMS) δ=1.43 (3H, s), 1.62 (2H, m), 1.84 (1H, m), 2.25-2.41 (2H, m), 2.51 (1H, dd, J=13.7, 4.9 Hz), 2.60 (1H, dd, J=13.7, 10.0 Hz), 2.80 (1H, brs), 3.56 (3H, s), 4.21 (1H, d, J=14.3 Hz), 4.45 (1H, d, J=14.3 Hz), 7.12 (2H, d, J=8.4 Hz), 7.25 (2H, d, J=8.4 Hz), 7.95 (1H, s), 8.40 (1H, s)

Preparative Example 4

Preparation of methyl-(1RS,2RS,3SR)-3-(4-chlorobenzyl)-2-hydroxy-1-methyl-2-(1H-1,2,4-triazol-1-ylmethyl)cyclopentanecarboxylate (compound (I-2): $R^1$=$CH_3$, $R^2$=$COOCH_3$, A=N, Ym=4-Cl, configuration: CC)

Under argon atmosphere, compound (I-1) (0.292 mmol) was suspended in dehydrated methanol 1.0 ml; dehydrated benzene 3.6 ml was added thereto for solubilization; 2.0 M solution of trimethylsilyl diazomethane in hexane solution (0.350 mmol) was added dropwise over 2 minutes. After heating and foaming subsided, the mixture was agitated at room temperature for 2 hours. After the reaction, the yellow homogeneous solution was distilled under reduced pressure for removal of the solvent, and the residue obtained was separated and purified by silica gel column chromatography, to give the title compound.

Yield: 100%

$^1$H-NMR (400 MHz, CDCl$_3$, TMS) δ=0.70 (3H, s), 1.76-1.52 (3H, m), 2.05 (1H, m), 2.35 (1H, m), 2.66 (2H, m), 3.69 (3H, s), 4.21 (1H, d, J=14.1 Hz), 4.60 (1H, brs), 4.62 (1H, d, J=14.1 Hz), 7.10 (2H, d, J=8.5 Hz), 7.23 (2H, d, J=8.5 Hz), 8.00 (1H, s), 8.20 (1H, s)

Preparative Example 5

Preparation of ethyl-(1RS,2SR,3RS)-3-(4-chlorobenzyl)-2-hydroxy-1-methyl-2-(1H-1,2,4-triazol-1-ylmethyl)cyclopentanecarboxylate (compound (I-133): R$^1$=CH$_3$, R$^2$=COOC$_2$H$_5$, A=N, Ym=4-Cl, configuration: TC)

Under argon atmosphere, compound (I-131) (0.296 mmol) was dissolved in dehydrated THF 3.1 ml, and ethanol 0.709 mmol and triphenylphosphine (0.709 mmol) were added thereto. DEAD (0.709 mmol) was added dropwise to the suspension, as the mixture was ice-cooled and the yellow solution formed was agitated at room temperature for 0.5 hour. After the reaction, the solvent was removed by distillation under reduced pressure, and the residue obtained was separated and purified by silica gel column chromatography, to give the title compound.

$^1$H-NMR (400 MHz, CDCl$_3$, TMS) δ=1.22 (3H, t, J=7.1 Hz), 1.44 (3H, s), 1.65 (3H, m), 1.82 (1H, m), 2.27 (1H, m), 2.38 (1H, m), 2.48 (1H, dd, J=13.6, 4.7 Hz), 2.58 (1H, dd, J=13.6, 10.1 Hz), 3.98 (2H, q, J=7.1 Hz), 4.19 (1H, d, J=14.3 Hz), 4.42 (1H, d, J=14.3 Hz), 5.40 (1H, s), 7.12 (2H, d, J=8.4 Hz), 7.25 (2H, d, J=8.4 Hz), 7.86 (1H, s), 8.18 (1H, s)

Preparative Example 6

Preparation of allyl-(1RS,2SR,3RS)-3-(4-chlorobenzyl)-2-hydroxy-1-methyl-2-(1H-1,2,4-triazol-1-ylmethyl)cyclopentanecarboxylate (compound (I-134): R$^1$=CH$_3$, R$^2$=COOCH$_2$CH=CH$_2$, A=N, Ym=4-Cl, configuration: TC)

The title compound was prepared by a method similar to that for preparation of the compound (I-133) described above, except that ethanol was replaced with allyl alcohol.

Yield: 81%

$^1$H-NMR (400 MHz, CDCl$_3$, TMS) δ=1.46 (3H, s), 1.63 (2H, m), 1.83 (1H, m), 2.34 (2H, m), 2.46 (1H, dd, J=13.6 Hz, 4.7 Hz), 2.58 (1H, dd, J=13.6, 10.2 Hz), 4.20 (1H, d, J=14.3 Hz), 4.39 (1H, ddt, J=13.4, 5.7, 1.3 Hz), 4.43 (1H, d, J=14.3 Hz), 4.46 (1H, ddt, J=13.4, 5.7, 1.5 Hz), 5.25 (1H, ddd, J=10.5, 2.6, 1.3 Hz), 5.28 (1H, d, J=0.9 Hz), 5.31 (1H, ddd, J=17.2, 2.6, 1.5 Hz), 5.85 (1H, ddt, J=17.2, 10.5, 5.7 Hz), 7.12 (2H, d, J=8.4 Hz), 7.25 (2H, d, J=8.4 Hz), 7.85 (1H, s), 8.17 (1H, s)

Preparative Example 7

Preparation of 2-propynyl-(1RS,2SR,3RS)-3-(4-chlorobenzyl)-2-hydroxy-1-methyl-2-(1H-1,2,4-triazol-1-ylmethyl)cyclopentanecarboxylate (compound (I-135): R$^1$=CH$_3$, R$^2$=COOCH$_2$C≡CH, A=N, Ym=4-Cl, configuration: TC)

The title compound was prepared by a method similar to that for preparation of the compound (I-133) described above, except that ethanol was replaced with 2-propyn-1-ol.

Yield: 67%

$^1$H-NMR (400 MHz, CDCl$_3$, TMS) δ=1.46 (3H, s), 1.63 (2H, m), 1.83 (1H, m), 2.34 (2H, m), 2.41 (1H, dd, J=9.6, 4.6 Hz), 2.49 (1H, t, J=2.5 Hz, —CCH), 2.55 (1H, dd, J=13.9, 9.6 Hz), 4.21 (1H, d, J=14.3 Hz), 4.46 (1H, d, J=14.3 Hz), 4.51 (1H, dd, J=15.6 Hz, 2.5 Hz), 4.58 (1H, dd, J=15.6, 2.5 Hz), 5.00 (1H, d, J=0.6 Hz), 7.12 (2H, d, J=8.4 Hz, H-2, 6 of Ph), 7.24 (2H, d, J=8.4 Hz), 7.89 (1H, s), 8.16 (1H, s)

Preparative Example 8

Preparation of n-propyl-(1RS,2SR,3RS)-3-(4-chlorobenzyl)-2-hydroxy-1-methyl-2-(1H-1,2,4-triazol-1-ylmethyl)cyclopentanecarboxylate (compound (I-136): R$^1$=CH$_3$, R$^2$=COOC$_3$H$_7$, A=N, Ym=4-Cl, configuration: TC)

The title compound was prepared as pale yellow oily by a method similar to that for preparation of the compound (I-3) described above, except that ethanol was replaced with n-propanol.

Yield: quantitative.

$^1$H-NMR (400 MHz, CDCl$_3$, TMS) δ=0.94 (3H, t, J=7.4 Hz,), 1.44 (3H, s), 1.59 (5H, m), 1.83 (1H, m), 2.33 (2H, m,), 2.47 (1H, dd, J=13.6, 4.6 Hz), 2.58 (1H, dd, J=13.6, 10.1 Hz), 3.89 (2H, m), 4.19 (1H, d, J=14.3 Hz), 4.42 (1H, d, J=14.3 Hz), 5.40 (1H, s), 7.12 (2H, d, J=8.4 Hz), 7.24 (2H, d, J=8.4 Hz), 7.85 (1H, s), 8.17 (1H, s)

Preparative Example 9

Preparation of ethyl-(1RS,2RS,3SR)-3-(4-chlorobenzyl)-2-hydroxy-1-methyl-2-(1H-1,2,4-triazol-1-ylmethyl)cyclopentanecarboxylate (compound (I-3): R$^1$=CH$_3$, R$^2$=COOC$_2$H$_5$, A=N, Ym=4-Cl, configuration: CC)

The title compound was prepared by a method similar to that for preparation of the compound (I-133) described above, except that compound (I-131) was replaced with compound (I-1).

Yield: quantitative.

$^1$H-NMR (400 MHz, CDCl$_3$, TMS) δ=0.68 (3H, s), 1.26 (3H, t, J=7.1 Hz), 1.52 (1H, m), 1.71 (2H, m), 2.03 (1H, m), 2.36 (1H, m), 2.67 (2H, m), 4.14 (2H, q, J=7.1 Hz), 4.19 (1H, d, J=14.0 Hz), 4.59 (1H, s), 4.65 (1H, d, J=14.0 Hz), 7.10 (2H, d, J=8.5 Hz), 7.24 (2H, d, J=8.5 Hz), 7.98 (1H, s), 8.12 (1H, s)

Preparative Example 10

Preparation of allyl-(1RS,2RS,3SR)-3-(4-chlorobenzyl)-2-hydroxy-1-methyl-2-(1H-1,2,4-triazol-1-ylmethyl)cyclopentanecarboxylate (compound (I-4): R$^1$=CH$_3$, R$^2$=COOCH$_2$CH=CH$_2$, A=N, Ym=4-Cl, configuration: CC)

The title compound was prepared by a method similar to that for preparation of the compound (I-3) described above, except that ethanol was replaced with allyl alcohol.

Yield: 90%

$^1$H-NMR (400 MHz, CDCl$_3$, TMS) δ=0.69 (3H, s), 1.54 (1H, m), 1.73 (2H, m), 2.06 (1H, m), 2.37 (1H, m), 2.66 (1H, dd, J=13.9 Hz, 9.0 Hz), 2.71 (1H, dd, J=13.9, 6.2 Hz), 4.19 (1H, d, J=14.1 Hz), 4.57 (1H, ddt, J=13.2, 5.8, 1.3 Hz), 4.61 (1H, d, J=14.1 Hz), 4.62 (1H, m), 4.65 (1H, d, J=1.5 Hz), 5.29 (1H, ddd, J=10.5, 2.5, 1.3 Hz), 5.33 (1H, ddd, J=17.2, 2.5, 1.5 Hz), 5.92 (1H, ddt, J=17.2, 10.5, 5.8 Hz), 7.10 (2H, d, J=8.5 Hz), 7.23 (2H, d, J=8.5 Hz), 7.98 (1H, s), 8.10 (1H, s)

Preparative Example 11

Preparation of 2-propynyl-(1RS,2RS,3SR)-3-(4-chlorobenzyl)-2-hydroxy-1-methyl-2-(1H-1,2,4-triazol-1-ylmethyl)cyclopentanecarboxylate (compound (I-5): $R^1$=$CH_3$, $R^2$=$COOCH_2C\equiv CH$, A=N, Ym=4-Cl, configuration: CC)

The title compound was prepared by a method similar to that for preparation of the compound (I-3) described above, except that ethanol was replaced with 2-propyn-1-ol.

Yield: 91%

$^1$H-NMR (400 MHz, CDCl$_3$, TMS) δ=0.67 (3H, s), 1.56 (1H, m), 1.77 (2H, m), 2.05 (1H, m), 2.40 (1H, m), 2.55 (1H, t, J=2.4 Hz), 2.69 (1H, dd, J=13.9, 8.8 Hz), 2.75 (1H, dd, J=13.9, 6.1 Hz), 4.18 (1H, d, J=14.2 Hz), 4.56 (1H, d, J=14.2 Hz), 4.69 (1H, dd, J=15.5 Hz, 2.4 Hz), 4.75 (1H, dd, J=15.5, 2.4 Hz), 4.81 (1H, d, J=1.6 Hz), 7.12 (2H, d, J=8.4 Hz), 7.24 (2H, d, J=8.4 Hz), 7.99 (1H, s), 8.21 (1H, s)

Preparative Example 12

Preparation of n-propyl-(1RS,2RS,3SR)-3-(4-chlorobenzyl)-2-hydroxy-1-methyl-2-(1H-1,2,4-triazol-1-ylmethyl)cyclopentanecarboxylate (compound (I-6): $R^1$=$CH_3$, $R^2$=$COOC_3H_7$, A=N, Ym=4-Cl, configuration: CC)

The title compound was prepared by a method similar to that for preparation of the compound (I-3) described above, except that ethanol was replaced with n-propanol.

Yield: quantitative $^1$H-NMR (400 MHz, CDCl$_3$, TMS) δ=0.68 (3H, s), 0.93 (3H, t, J=7.4 Hz), 1.53 (1H, m), 1.65 (2H, m), 1.74 (2H, m), 2.02 (1H, m), 2.37 (1H, m), 2.68 (2H, m), 4.04 (2H, m), 4.19 (1H, d, J=14.0 Hz), 4.58 (1H, s), 4.65 (1H, d, J=14.0 Hz), 7.10 (2H, d, J=8.4 Hz), 7.23 (2H, d, J=8.4 Hz), 7.98 (1H, s), 8.12 (1H, s)

Preparative Example 13

Preparation of isopropyl-(1RS,2SR,3RS)-3-(4-chlorobenzyl)-2-hydroxy-1-methyl-2-(1H-1,2,4-triazol-1-ylmethyl)cyclopentanecarboxylate (compound (I-137): $R^1$=$CH_3$, $R^2$=$COOCH(CH_3)_2$, A=N, Ym=4-Cl, configuration: TC)

(1) Preparation of (1RS,4RS,5SR)-4-(4-chlorobenzyl)-1-methyl-5-[1,2,4]triazol-1-ylmethyl-6-oxabicyclo[3,2,0]heptan-7-one (compound (X-1): $R^1$=$CH_3$, A=N, Ym=4-Cl, configuration: TC)

Under argon atmosphere, compound (I-131) (0.100 mmol) was dissolved in dehydrated THF 1.8 ml; WSC (0.120 mmol), dimethylaminopyridine (0.010 mmol), and diisopropylethylamine (0.200 mmol) were added thereto; and the mixture was agitated at room temperature for 1 hour. After the reaction, ethyl acetate 10 ml was added thereto; the mixture was washed with 1 M HClaq. and saturated aqueous sodium chloride solution, and dehydrated over anhydrous sodium sulfate. The solvent was removed by distillation under reduced pressure; and the residue obtained was separated and purified by silica gel column chromatography, to give the title compound.

Yield: 100%

$^1$H-NMR (400 MHz, CDCl$_3$, TMS) δ=1.48 (3H, s), 1.49 (2H, m), 1.77 (1H, m), 1.96 (1H, m), 2.12 (1H, m), 2.51 (2H, d, J=7.1 Hz), 4.59 (1H, d, J=15.3 Hz), 4.63 (1H, d, J=15.3 Hz), 7.02 (2H, d, J=8.0 Hz), 7.26 (2H, d, J=8.0 Hz), 8.05 (1H, s), 8.17 (1H, s)

(2) Preparation of isopropyl-(1RS,2SR,3RS)-3-(4-chlorobenzyl)-2-hydroxy-1-methyl-2-(1H-1,2,4-triazol-1-ylmethyl)cyclopentanecarboxylate (compound (I-137): $R^1$=$CH_3$, $R^2$=$COOCH(CH_3)_2$, A=N, Ym=4-Cl, configuration: TC)

Under argon atmosphere, 2-propanol (0.0976 mmol) was added to dehydrated THF 100 μl; 1.58 M n-butyllithium/hexane solution (0.107 mmol) was added thereto over 1 minute, as the mixture was ice-cooled; and the mixture was agitated for 0.5 hour. The mixture was cooled to −78° C.; a solution of compound (X-1) (0.0325 mmol) in THF 224 μl was added dropwise over 3 minutes; and the mixture was warmed gradually to room temperature over 19 hours. After the reaction, water 0.5 ml was added thereto for termination of the reaction; the aqueous layer was extracted with ethyl acetate; and the extract was washed with saturated aqueous sodium chloride solution and dried over anhydrous sodium sulfate. The solvent was removed by distillation under reduced pressure; and the residue obtained was separated and purified by silica gel column chromatography, to give the title compound.

Yield: 87.9%

$^1$H-NMR (400 MHz, CDCl$_3$, TMS) δ=1.17 (3H, d, J=6.3 Hz), 1.21 (3H, d, J=6.3 Hz), 1.42 (3H, s), 1.59 (2H, m), 1.81 (1H, m), 2.21-2.45 (3H, m), 2.55 (1H, dd, J=13.6, 10.3 Hz), 4.21 (1H, d, J=14.3 Hz), 4.43 (1H, d, J=14.3 Hz), 4.82 (1H, sept. J=6.3 Hz), 5.47 (1H, s), 7.11 (2H, d, J=8.4 Hz), 7.24 (2H, d, J=8.4 Hz), 7.86 (1H, s), 8.18 (1H, s)

Preparative Example 14

Preparation of N-methyl-(1RS,2SR,3RS)-3-(4-chlorobenzyl)-2-hydroxy-1-methyl-2-(1H-1,2,4-triazol-1-ylmethyl)cyclopentane carboxyamide (compound (I-148): $R^1$=$CH_3$, $R^2$=$CONHCH_3$, A=N, Ym=4-Cl, configuration: TC)

Compound (X-1) (0.090 mmol) was dissolved in THF 0.9 ml; 40% aqueous methylamine solution (4.50 mmol) was added thereto and the mixture was left still at room temperature for 3.5 hours. After the reaction, the solvent was removed by distillation under reduced pressure, and the residue obtained was separated and purified by silica gel column chromatography, to give the title compound.

Yield: 99%

$^1$H-NMR (400 MHz, CDCl$_3$, TMS) δ=1.42 (3H, s), 1.47 (1H, m), 1.69 (1H, m), 1.83 (1H, m), 2.37 (2H, m), 2.55 (3H, d, J=4.8 Hz), 2.69 (2H, d, J=7.4 Hz), 4.16 (1H, d, J=14.4 Hz), 4.33 (1H, d, J=14.4 Hz), 5.68 (1H, brs), 6.78 (1H, s), 7.15 (2H, d, J=8.4 Hz), 7.25 (2H, d, J=8.4 Hz), 7.83 (1H, s), 8.20 (1H, s)

Preparative Example 15

Preparation of (1RS,2SR,3RS)-3-(4-fluorobenzyl)-2-hydroxy-1-methyl-2-(1H-1,2,4-triazol-1-ylmethyl)-1-cyclopentanemethanol (compound number (III-2): $R^1$=$CH_3$, A=N, Ym=4-Cl, configuration: CC) (Preparative Example, via Step 2E)

(1SR,4SR,5RS)-(4-fluorobenzyl)-1-hydroxymethyl-5-(1H-[1,2,4]triazol-1-ylmethyl)-6-oxabicyclo[3,2,0]heptane (compound number (XIII-1): A=N, Ym=4-F, configuration: CC) (0.173 mmol) was dissolved in THF 2 mL; lithium aluminum hydride (0.870 mmol) and aluminum chloride (0.517 mmol) were added thereto; and the mixture was agitated at room temperature for 4.5 hours. Lithium aluminum hydride (0.527 mmol) was added thereto additionally and the mixture was agitated for 1.5 hours.

After the reaction, the mixture was cooled in an ice bath; purified water, 2N aqueous sodium hydroxide solution, and ethyl acetate were added thereto; and the mixture was agitated at room temperature for 1 hour. Insoluble matter generated was removed by Celite filtration and the filtrate was extracted with ethyl acetate. The organic layer was washed with saturated aqueous sodium chloride solution and dried over anhydrous sodium sulfate, and the solvent was removed by distillation under reduced pressure. The residue was purified by silica gel column chromatography, to give the title compound III-2 as white solid.

Yield: 57.0%

Preparative Example 16

Preparation of (1RS,2SR,3RS)-3-benzyl-2-hydroxy-1-methyl-2-(1H-1,2,4-triazol-1-ylmethyl)-1-cyclopentanemethanol (compound number (III-3): $R^1$=$CH_3$, A=N, Ym=unsubstituted, configuration: CC) (Preparative Example via Step 2E)

The title compound (III-3) was obtained by a method similar to that for preparation of the compound (III-2) above, except that (1SR, 4SR, 5RS)-4-benzyl-1-hydroxymethyl-5-(1H-[1,2,4]triazol-1-ylmethyl)-6-oxabicyclo[3,2,0]heptane (compound number: XIII-2: A=N, Ym=unsubstituted, configuration: CC) was used as the raw material, replacing compound (XIII-1).

Yield: 42.7%

Preparative Example 17

Preparation of (1RS, 2SR,3RS)-3-(4-fluorobenzyl)-2-hydroxy-1-methyl-2-(1H-1,2,4-triazol-1-ylmethyl)-1-cyclopentanecarboxylic acid (compound (I-52): $R^1$=$CH_3$, $R^2$=COOH, A=N, Ym=4-F, configuration: CC)

The title compound (I-52) was prepared by a method similar to that for preparation of the compound (I-1) above, except that compound (III-2) was used as the raw material, replacing (1RS, 2SR,3RS)-3-(4-chlorobenzyl)-2-hydroxy-1-methyl-2-(1H-1,2,4-triazol-1-ylmethyl)-1-cyclopentanemethanol (compound (III-1).

$^1$H-NMR (400 MHz, $CDCl_3$, TMS) δ=0.75 (3H, s), 1.54-1.64 (1H, m), 1.67-1.74 (1H, m), 1.78-1.87 (1H, m), 2.10-2.17 (1H, m), 2.39-2.47 (1H, m), 2.70 (1H, dd, J=13.8, 9.4 Hz), 2.78 (1H, dd, J=13.8, 5.5 Hz), 4.22 (1H, d, J=14.1 Hz), 4.53 (1H, brs), 4.67 (1H, d, J=14.1 Hz), 6.93-6.98 (2H, m), 7.13-7.17 (2H, m), 8.02 (1H, s), 8.34 (1H, s)

Preparative Example 18

Preparation of methyl-(1RS, 2SR,3RS)-3-(4-fluorobenzyl)-2-hydroxy-1-methyl-2-(1H-1,2,4-triazol-1-ylmethyl)cyclopentanecarboxylate (compound (I-53): $R^1$=$CH_3$, $R^2$=$COOCH_3$, A=N, Ym=4-F, configuration: CC)

The title compound (I-53) was prepared by a method similar to that for preparation of the compound (I-2) above, except that (1RS, 2SR,3RS)-3-(4-fluorobenzyl)-2-hydroxy-1-methyl-2-(1H-1,2,4-triazol-1-ylmethyl)-1-cyclopentanecarboxylic acid (compound (I-52)) was used as the raw material, replacing compound I-1.

Yield: 63.9%

$^1$H-NMR (400 MHz, $CDCl_3$, TMS) δ=0.69 (3H, s), 1.51-1.57 (1H, m), 1.67-1.80 (2H, m), 2.02-2.09 (1H, m), 2.30-2.38 (1H, m), 2.62-2.70 (2H, m), 3.69 (3H, s), 4.19 (1H, d, J=14.1 Hz), 4.61 (1H, brs), 4.61 (1H, d, J=14.1 Hz), 6.94-6.98 (2H, m), 7.10-7.15 (2H, m), 7.99 (1H, s), 8.12 (1H, s)

Preparative Example 19

Preparation of 2-(4-fluorobenzyl)-8,8-dimethyl-7,9-dioxa-spiro[4,5]decan-1-one (compound (XVI-1): Ym=4-F)

55% sodium hydride (25.4 mmol) was washed with hexane; DMF 12 mL was added thereto; and the mixture was cooled in an ice bath. A compound (X: $R^5$=$CH_3$) (21.1 mmol) was added dropwise thereto over 10 minutes and then, 4-fluorobenzyl chloride (26.2 mol) was added dropwise over 10 minutes. After the dropwise addition, the mixture was agitated at room temperature for 3 hours. After the reaction, the reaction solution was poured into ice water and the mixture was agitated for 10 minutes. Saturated aqueous sodium chloride solution was added thereto and the mixture was extracted with ethyl acetate. The organic layers were combined, washed with saturated aqueous sodium chloride solution and dried over anhydrous sodium sulfate, and the solvent was removed by distillation under reduced pressure, to give a crude product of the compound (XIX-1: $R^5$=$CH_3$, Ym=4-F).

It was dissolved in THF 19 mL; 37% aqueous formaldehyde solution (84.4 mmol), and potassium carbonate (10.0 mmol) were added thereto; and the mixture was agitated vigorously at room temperature for 12 hours. After the reaction, THF was removed by distillation under reduced pressure. 1N hydrochloric acid was added thereto to pH 2; the mixture was agitated at room temperature for 3 hours and extracted with ethyl acetate. The organic layers were combined, washed with 1N hydrochloric acid, saturated aqueous sodium bicarbonate solution, and saturated aqueous sodium chloride solution, and dried over anhydrous sodium sulfate, and the solvent was removed by distillation under reduced pressure, to give a crude product of the compound (XVIII-1: $R^5$=$CH_3$, Ym=4-F). It was dissolved in acetone 10 mL; acetone dimethyl acetal (0.105 mol) and p-toluenesulfonic acid monohydrate (4.00 mmol) were added thereto; and the mixture was agitated at room temperature for 1 hour. p-toluenesulfonic acid monohydrate (3.48 mmol) was added thereto; the mixture was agitated additionally for 1.5 hours; and acetone dimethyl acetal (8.75 mmol) was added; and the mixture was agitated for 1 hour. After the reaction, saturated aqueous sodium bicarbonate solution 100 mL was added thereto and the mixture was extracted with ethyl acetate. The organic layers were combined, washed with saturated aqueous sodium chloride solution and dried over anhydrous sodium sulfate, and the solvent was removed by distillation under reduced pressure, to give a crude product of the compound (XVII-1: $R^5$=$CH_3$, Ym=4-F).

Toluene 2 mL and 25% aqueous sodium hydroxide solution 20 mL were added thereto and the mixture was agitated at 70° C. for 2 hours. The reaction solution was extracted with ethyl acetate. The organic layers were combined; as there was no phase separation when saturated aqueous sodium chloride solution was added, the solvent was removed by distillation under reduced pressure; ethyl acetate 200 mL was added thereto; and the resulting insoluble matter was removed by filtration. Ethyl acetate was removed by distillation under reduced pressure; hexane 200 mL was added thereto; and the insoluble matter was removed by filtration. Hexane was removed by distillation under reduced pressure; the residue was purified by silica gel column chromatography (silica gel 60N; neutral/spherical, produced by Kanto Chemical Co. Inc., hexane/ethyl acetate=5/1), to give the title compound (XVI-1).

Yield: 29.4% (4 steps)

Preparative Example 20

Preparation of 2-(4-fluorobenzyl)-8,8-dimethyl-1-[1,2,4]triazole-7,9-dioxa-spiro[4,5]decan-1-ol (compound (XV-1): A=N, Ym=4-F)

Triazole sodium salt (6.54 mmol) was dissolved in NMP 4 mL and the mixture was heated to 115° C. (internal temperature). 2-(4-Fluorobenzyl)-8,8-dimethyl-7,9-dioxaspiro[4,5]decan-1-one (compound (XVI-1): Ym=4-F) 1.27 g dissolved in NMP 3 mL was added thereto. After the internal temperature reached 116° C., sodium t-butoxide (2.61 mmol) and TMSOB (5.87 mmol) were added in portions over 2.3 hours to carry out the reaction. After all reagents were added, the mixture was agitated additionally for 25 minutes. The reaction solution was cooled to room temperature; saturated aqueous sodium chloride solution was added thereto; and the mixture was extracted with ethyl acetate. The organic layers were combined, washed with saturated aqueous sodium chloride solution and dried over anhydrous sodium sulfate, and the solvent was removed by distillation under reduced pressure. The residue was purified by silica gel column chromatography, to give the title compound (XV-1) as an isomer mixture.

Yield: 66.7%

Preparative Example 21

Preparation of (1SR, 4SR,5RS)-4-(4-fluorobenzyl)-1-hydroxymethyl-5-(1H-[1,2,4]triazol-1-ylmethyl)-6-oxabicyclo[3,2,0]heptane (compound (XIII-1): A=N, Ym=4-F, configuration: CC)

Methanol 10 mL and 1N hydrochloric acid 10 mL were added to a compound (XV-1: A=N, Ym=4-F) (3.81 mmol) and the mixture was agitated at room temperature for 2 hours. After the reaction, 2N aqueous sodium hydroxide solution was added thereto to pH 10 and the white solid precipitated formed was collected by filtration and washed with purified water. The white solid obtained was dried, to give a crude product of the compound (XIV-1: A=N, Ym=4-F). The filtrate obtained by the operation was extracted with ethyl acetate. The organic layers were combined, washed with saturated aqueous sodium chloride solution and dried over anhydrous sodium sulfate, and the solvent was removed by distillation under reduced pressure, to give a crude product of the compound (XIV-1: A=N, Ym=4-F).

THF 2 mL was added to 55% sodium hydride (5.61 mmol); the mixture was cooled in an ice bath; a suspension of a compound (XIV-1: A=N, Ym=4-F) 0.60 g in THF 8 mL was added dropwise thereto. The mixture was agitated at the same temperature for 10 minutes; after addition of p-toluenesulfonyl chloride (2.24 mmol), the mixture was agitated back at room temperature for 4 hours. Sodium hydride (2.29 mmol) was added thereto and the mixture was agitated additionally for 2 hours. After the reaction, purified water was added and the mixture was extracted with ethyl acetate. The organic layers were combined, washed with saturated aqueous sodium chloride solution and dried over anhydrous sodium sulfate, and solvent was removed by distillation under reduced pressure. The residue was purified by silica gel column chromatography, to give the title compound (XIII-1: A=N, Ym=4-F, configuration: CC).

Yield: 69.9% (2 steps)

$^1$H-NMR (400 MHz, $CDCl_3$, TMS) δ=1.47-1.56 (2H, m), 1.84-1.97 (3H, m), 2.62 (1H, dd, J=13.7, 8.2 Hz), 2.69 (1H, dd, J=13.7, 6.4 Hz), 3.45 (1H, dd, J=12.9, 9.9 Hz), 3.97 (1H, dd, J=12.9, 3.5 Hz), 4.15 (1H, d, J=6.3 Hz), 4.19 (1H, d, J=6.3 Hz), 4.22 (1H, d, J=15.0 Hz), 4.67 (1H, d, J=15.0 Hz), 4.69 (1H, dd, J=9.9, 3.5 Hz), 6.95-7.00 (2H, m), 7.01-7.05 (2H, m), 7.64 (1H, s), 7.97 (1H, s)

Preparative Example 22

Preparation of (1RS, 4SR, 5RS)-4-(4-fluorobenzyl)-5-[1,2,4]triazol-1-ylmethyl-6-oxabicyclo[3,2,0]heptane-1-carboxylic acid (compound (XII-1): A=N, Ym=4-F, configuration: CC) (Preparation, using Jones oxidation in Step 2D1)

A compound (XIII-1) (0.158 mmol) was dissolved in acetone 1 mL and purified water 0.5 mL, and sodium dichromate dihydrate (0.198 mmol) was added thereto. 1 mol/L aqueous sulfuric acid solution (0.630 mmol) was added dropwise thereto gradually and the mixture was agitated at room temperature for 3 hours. After the reaction, 2N aqueous sodium hydroxide solution was added thereto to pH 10 and the mixture was left still with added Celite at room temperature overnight. Celite was removed by filtration and washed with 2N aqueous sodium hydroxide solution. The filtrate was washed with ethyl acetate; 2N aqueous sulfuric acid solution was added thereto to pH 4; and the mixture was extracted with ethyl acetate. After the organic layer was washed with saturated aqueous sodium chloride solution and dried over anhydrous sodium sulfate, the solvent was removed by distillation under reduced pressure, to give the title compound (XII-1).

Yield: 97.8%

$^1$H-NMR (400 MHz, $CDCl_3$, TMS) δ=1.72-1.76 (1H, m), 1.83-1.91 (2H, m), 1.93-2.01 (1H, m), 2.40-2.50 (2H, m), 3.21-2.22 (1H, m), 4.06 (1H, d, J=6.2 Hz), 4.53-4.62 (3H, m), 6.88-6.92 (2H, m), 7.09-7.12 (2H, m), 7.89 (1H, s), 8.32 (1H, s).

Preparative Example 23

Preparation of methyl-(1RS, 2SR,3RS)-3-(4-fluorobenzyl)-1-chloromethyl-2-hydroxy-2-(1H-1,2,4-triazol-1-ylmethyl)cyclopentanecarboxylate (compound (I-78): $R^1$=$CH_2Cl$, $R^2$=$COOCH_3$, A=N, Ym=4-F, configuration: CC) (Preparation, using PDC oxidation in Step 2D1)

A compound (XIII-1) (0.158 mmol) was dissolved in DMF 1 mL and, after addition of PDC (0.190 mmol), the mixture was agitated at room temperature for 5 hours. After addition of PDC (0.080 mmol), the mixture was agitated additionally for 1 hour and also for 0.5 hour at 50° C. The mixture was treated below in a manner similar to Preparative Example 22, to give a compound (XII-1: A=N, Ym=4-F, configuration: CC).

It was dissolved in dehydrated methanol; 2M trimethylsilyl diazomethane hexane solution 0.1 mL (0.20 mmol) was added thereto; and the mixture was agitated at room temperature for 2.5 hours. After the reaction, saturated aqueous sodium chloride solution was added thereto and the mixture was extracted with ethyl acetate. The organic layer was washed with saturated aqueous sodium chloride solution and dried over anhydrous sodium sulfate, and the solvent was removed by distillation under reduced pressure, to give a compound (XI-1: $R^3$=$CH_3$, A=N, Ym=4-F, configuration: CC).

It was dissolved in DMF 1 mL; lithium chloride (0.217 mmol) and p-tosic acid monohydrate 8.9 mg (0.0516 mmol) were added thereto; and the mixture was agitated at 80° C. for 5 hours. After the reaction, saturated aqueous sodium chloride solution was added thereto and the mixture was extracted with ethyl acetate. The organic layer was dried over anhydrous sodium sulfate and the solvent was removed by distillation under reduced pressure. The residue was purified by silica gel column chromatography, to give the title compound (I-78).

Yield: 18.2% (3 steps)

$^1$H-NMR (CDCl$_3$) δ=1.52-1.61 (1H, m), 1.72-1.86 (1H, m), 1.92-1.99 (1H, m), 2.17-2.21 (1H, m), 2.25-2.32 (1H, m), 2.41 (1H, dd, J=13.7, 4.8 Hz), 2.56 (1H, dd, J=13.7, 10.1 Hz), 3.27 (1H, d, J=10.6 Hz), 3.54 (1H, d, J=10.6 Hz), 3.78 (3H, s), 4.28 (1H, d, J=14.2 Hz), 4.36 (1H, d, J=14.2 Hz), 5.13 (1H, s), 6.92-6.96 (2H, m), 7.02-7.05 (2H, m), 8.02 (1H, s), 8.20 (1H, s).

Formulation Example 1

Wettable Powder

Compound (I-2) 50 parts,
lignin sulfonate salt 5 parts,
alkylsulfonate salt 3 parts, and
diatomaceous earth 42 parts
were pulverized and mixed, to give a wettable powder. It was used, as it was diluted with water.

Formulation Example 2

Powder

Compound (I-2) 3 parts,
clay 40 parts, and
talc 57 parts
were pulverized and mixed and the product was used as a powder.

Formulation Example 3

Granule

Compound (I-2) 5 parts,
bentonite 43 parts,
clay 45 parts, and
ligninsulfonate salt 7 parts
were mixed uniformly; the mixture was kneaded with water and processed and dried in an extruding granulator into a granular formulation.

Formulation Example 4

Emulsion

Compound (I-2) 20 parts,
polyoxyethylene alkylarylether 10 parts,
polyoxyethylene sorbitan monolaurate 3 parts, and
xylene 67 parts
were mixed and dissolved uniformly, to give an emulsion.

Test Example 1

Study on Antimicrobial Activity to Wheat Leaf Blight-Causing Microbes

In this Test Example, antimicrobial activity of the inventive compounds to wheat leaf blight-causing microbe was determined and compared with that of the comparative compound (1).

Comparative Compound (1)

(1RS,5SR)-5-(4-chlorobenzyl)-2-dimethyl-1-(1H-1,2,4-triazol-1-ylmethyl)cyclopentanol

[C. 30]

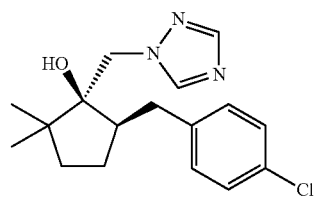

(1)

An inventive compound was dissolved in dimethylsulfoxide 2 ml. The solution 0.6 ml was added to a PDA medium (potato-dextrose-agar medium) 60 ml at around 60° C. The mixture was mixed thoroughly in a 100 ml Erlenmeyer flask and poured into a petri-dish, allowing solidification of the mixture, to give a flat plate containing the inventive compound.

A flat plate containing a test microbe (wheat leaf blight-causing microbe) cultured separately was punched into pieces with a cork borer having a diameter of 4 mm and the circular plate obtained was placed on the flat plate media containing the chemical described above. The plates were cultured at 25° C. for 14 days after inoculation and the diameter of the microbial colony was determined. Hyphal expansion-inhibiting rate was calculated according to the following equation:

$$R=100(dc-dt)/dc$$

(wherein, R: hyphal expansion-inhibiting rate (%), dc: diameter of microbial colony on non-treated flat plate, dt: diameter of microbial colony on chemically-treated flat plate).

The results thus obtained were evaluated into five grades according to the following criteria:
<Growth Inhibition>
5: hyphal expansion-inhibiting rate: 80% or more
4: hyphal expansion-inhibiting rate: 60% or more and less than 80%
3: hyphal expansion-inhibiting rate: 40% or more and less than 60%
2: hyphal expansion-inhibiting rate: 20% or more and less than 40%
1: hyphal expansion-inhibiting rate: less than 20%

TABLE 13

| Compound number | Concentration (mg/L) | Growth inhibition |
|---|---|---|
| I-132 | 50 | 5 |
| I-2 | 50 | 5 |
| I-148 | 50 | 5 |
| I-133 | 50 | 5 |
| I-134 | 50 | 5 |
| I-135 | 50 | 5 |
| I-3 | 50 | 5 |
| I-4 | 50 | 5 |
| I-5 | 50 | 5 |
| I-136 | 50 | 5 |
| I-6 | 50 | 5 |
| I-137 | 50 | 5 |
| I-392 | 50 | 5 |
| I-78 | 50 | 5 |
| I-53 | 50 | 5 |
| 化合物 (1) | 50 | 5 |

As shown in Table 13, compounds I-132, I-2, I-148, I-134, I-135, I-3, I-4, I-5, I-136, I-6, I-137, I-392, I-78, and I-53 show an antimicrobial activity similar to that of a known compound (1) commercially available under the name of Metconazole. When the test was performed at a test sample concentration of 1.25 mg/L, instead of 50 mg/L in Table 13, the compound (1) showed a hyphal expansion-inhibiting rate of 60% or more and less than 80%, while compounds I-2, I-3, I-5, I-6, and I-53 showed a hyphal expansion-inhibiting rate of 80% or more, indicating that these compounds have an activity higher than that of the compound (1).

Test Example 2

Study on Wheat Leaf Rust-Controlling Activity

The formulation in the shape of wettable powder prepared in Formulation Example 1 was applied on wheat (type: Norin No. 61) in the second leaf stage grown in a square plastic pot (6 cm×6 cm), as it is diluted and suspended with water to a concentration of 2 mg/L, at a rate of 1,000 L/ha. After the leaves sprayed were dried in air, spores of a wheat leaf rust-causing microbe (adjusted to 200 counts/visual field, Gramin S is added at a concentration of 60 ppm) were inoculated by spraying, and the wheat was left at 25° C. under high-humidity condition for 48 hours.

The wheat was then grown in greenhouse. The incidence rate of the wheat leaf rust was determined 9 to 14 days after inoculation and the controlling rate was calculated according to the following equation:

Controlling rate (%)=(1−Average incidence rate in compound-treated region/Average incidence rate in non-treated region)×100

TABLE 14

| Incidence rate | Areal rate of disease |
|---|---|
| 0 | No disease |
| 0.5 | Areal rate of disease: less than 1% |
| 1 | Areal rate of disease: 1% or more and less than 5% |
| 2 | Areal rate of disease: 5% or more and less than 10% |
| 3 | Areal rate of disease: 10% or more and less than 30% |
| 4 | Areal rate of disease: 30% or more and less than 50% |
| 5 | Areal rate of disease: 50% more |

TABLE 15

| Leaf rust-controlling index | |
|---|---|
| Controlling index | Controlling rate |
| 1 | 0 to 20 |
| 2 | 21 to 40 |
| 3 | 41 to 60 |
| 4 | 61 to 80 |
| 5 | 81 to 100 |

TABLE 16

| Compound number | Concentration (g/ha) | Controlling index |
|---|---|---|
| I-132 | 25 | 5 |
| I-2 | 25 | 5 |
| I-148 | 25 | 5 |
| I-133 | 25 | 5 |
| I-134 | 25 | 5 |
| I-135 | 25 | 5 |
| I-3 | 25 | 5 |
| I-4 | 25 | 5 |
| I-5 | 25 | 5 |
| I-136 | 25 | 5 |
| I-6 | 25 | 5 |
| I-137 | 25 | 5 |
| I-392 | 25 | 5 |
| I-78 | 25 | 5 |
| I-53 | 25 | 5 |
| Compound (1) | 25 | 5 |

As shown in Table 16, compounds I-132, I-2, I-148, I-134, I-135, I-3, I-4, I-5, I-136, I-6, I-137, I-392, I-78, and I-53 show a controlling activity to wheat leaf rust similar to that of a known compound (1) commercially available under the name of Metconazole. When the test was performed at a test sample concentration of 1 g/ha, instead of 25 g/ha in Table 16, the compound (1) had a controlling index of 4, while compounds I-132, I-2, I-137, and I-53 had a controlling index of 5, showing that these compounds have a controlling activity higher than that of the compound (1).

Test Example 3

Study on Antimicrobial Activity to Various Pathogenic Microbes and Hazardous Microorganisms In this Test Example, the antimicrobial activity of the inventive compounds to various plant disease-causing fungi and industrial material-eroding microorganisms was studied by the method described in Example 1.

The results thus obtained were evaluated in 5 stages according to the criteria below:

<Growth Inhibition>

5: hyphal expansion-inhibiting rate: 80% or more
4: hyphal expansion-inhibiting rate: 60% or more and less than 80%
3: hyphal expansion-inhibiting rate: 40% or more and less than 60%
2: hyphal expansion-inhibiting rate: 20% or more and less than 40%
1: hyphal expansion-inhibiting rate: less than 20%

TABLE 17

| Compound number | Concentration (mg/L) | P.n | P.h | F.g | U.n | P.o | G.f | A.m | S.s | B.c | F.c | R.sec |
|---|---|---|---|---|---|---|---|---|---|---|---|---|
| I-132 | 50 | 5 | 5 | 5 | 5 | 5 | 5 | 5 | 5 | 5 | 5 | 5 |
| I-2 | 50 | 5 | 5 | 5 | 5 | 5 | 5 | 5 | 5 | 5 | 5 | 5 |
| I-148 | 50 | 5 | 5 | 5 | 5 | 5 | 5 | 5 | 5 | 5 | 5 | 5 |
| I-133 | 50 | 5 | 5 | 5 | 5 | 5 | 5 | 5 | 5 | 5 | 5 | 5 |
| I-134 | 50 | 5 | 5 | 5 | 5 | 5 | 5 | 5 | 5 | 5 | 5 | 5 |
| I-135 | 50 | 5 | 5 | 5 | 5 | 5 | 5 | 5 | 5 | 5 | 5 | 5 |
| I-3 | 50 | 5 | 5 | 5 | 5 | 5 | 5 | 5 | 5 | 5 | 5 | 5 |
| I-4 | 50 | 5 | 5 | 5 | 5 | 5 | 5 | 5 | 5 | 5 | 5 | 5 |
| I-5 | 50 | 5 | 5 | 5 | 5 | 5 | 5 | 5 | 5 | 5 | 5 | 5 |
| I-136 | 50 | 5 | 5 | 5 | 5 | 5 | 5 | 5 | 5 | 5 | 5 | 5 |
| I-6 | 50 | 5 | 5 | 5 | 5 | 5 | 5 | 5 | 5 | 5 | 5 | 5 |
| I-137 | 50 | 5 | 5 | 5 | 5 | 5 | 5 | 5 | 5 | 5 | 5 | 5 |
| I-392 | 50 | 5 | 5 | 5 | 5 | 5 | 5 | 5 | 5 | 5 | 5 | 5 |
| I-78 | 50 | 5 | 5 | 5 | 5 | 5 | 5 | 5 | 5 | 5 | 5 | 5 |
| I-53 | 50 | 5 | 5 | 5 | 5 | 5 | 5 | 5 | 5 | 5 | 5 | 5 |

Wheat glume blotch-causing microbe (*Phaeosphaeria nodorum*) P.n
Wheat eye spot-causing microbe (*Pseudocercoporella herpotrichoides*) P.h
Wheat *fusarium* blight-causing microbe (*Fusarium graminearum*) F.g
Barley loose smut-causing microbe (*Ustilago nuda*) U.n
Rice blast-causing microbe (*Pyricularia oryzae*) P.o
Rice bakanae disease-causing microbe (*Gibberella fujikuroi*) G.f
Apple *alternaria* blotch-causing microbe (*Alternaria alternata*) A.m
*Sclerotinia* rot-causing microbe (*Sclerotinia sclerotiorum*) S.s
Gray mold-causing microbe (*Botrytis cinerea*) B.c
Cucumber *Fusarium* wilt-causing microbe (*Fusarium oxysporum*) F.c
Barley scald-causing microbe (*Rhynchosporium secalis*) R.sec As shown in Table 17, compounds I-132, I-2, I-148, I-134, I-135, I-3, I-4, I-5, I-136, I-6, I-137, I-392, I-78, and I-53 show high antimicrobial activity to a wide variety of pathogenic microbes. In other words, compounds I-132, I-2, I-148, I-134, I-135, I-3, I-4, I-5, I-136, I-6, I-137, I-392, I-78, and I-53 have a wide microbial spectrum.

Test Example 4

Control Activity of Wheat Leaf Rust by Seed Treatment

Controlling activity to wheat leaf rust was examined in a pot test. An inventive compound 1-2 and a comparative compound (1) were dissolved in DMSO (18 μl) respectively in an amount of 2 mg. The solution prepared was applied to wheat seeds 10 g in a vial and 8 wheat seeds were seeded in a 80 $cm^2$ pot. The seeds were grown in greenhouse, as water was supplied from below; a wheat leaf rust-causing microbe was inoculated 21 days after seeding; and the pot was stored in a constant-humidity box for 2 days. The plant was grown in green house, as water was supplied from below, and the incidence rate was determined and the controlling rate calculated 12 days after seeding.

The controlling rate was calculated according to the equation below and used as the wheat leaf rust-controlling rate.

Controlling rate=(1−Incidence rate in treated region/ Incidence rate in non-treated region)×100(%)

As a result, compound (1) had a controlling rate of 88, while compound (I-2) had a controlling rate of 95.

Test Example 5

Damage (Necrosis) to Wheat by Seed Treatment

Damage (necrosis) to wheat was examined in a pot test. An inventive compound 1-2 and a comparative compound (1) were dissolved in DMSO (18 μl) respectively in an amount of 2 mg. The solution thus prepared was applied to wheat seeds 1 g in a vial and 8 seeds were seeded in a 80 $cm^2$ pot. The plant was grown in green house, as water was supplied from below, and the damage was determined 12 days after seeding.

As a result, treatment with compound (1) gave necrotic symptom, while treatment with compound 1-2 gave no necrotic symptom.

Test Example 6

Controlling Activity to Wheat Powdery Mildew of Seed Treatment

Controlling activity to wheat powdery mildew was examined in a pot test. Each of the inventive compounds I-132, I-2, I-148, I-133, I-134, I-3, I-4, I-5, I-136, I-6, I-137, I-392, I-53, and a comparative compound (1) was weighed in an amount of 2 mg and dissolved in DMSO (18 μl). The solution thus prepared was applied to wheat seeds 1 g in a vial, 8 wheat seeds were seeded in a 80 $cm^2$ pot. The wheat was grown, as water was supplied from blow, in a greenhouse where wheat powdery mildew-causing microbes are present abundantly. The incidence rate was determined and the controlling rate and additionally the controlling index calculated 14 to 28 days after seeding.

The controlling rate was calculated and the wheat powdery mildew controlling index determined according to the following equation:

Controlling rate=(1−Incidence rate in treated region/ Incidence rate in non-treated region)×100(%)

TABLE 18

| Controlling index | Controlling rate |
|---|---|
| 0 | Controlling rate: 0 |
| 1 | Controlling rate: 10 or less |
| 2 | Controlling rate: 20 or less |
| 3 | Controlling rate: 30 or less |
| 4 | Controlling rate: 40 or less |
| 5 | Controlling rate: 40 or more |

As a result, compounds I-132, I-2, I-148, I-133, I-134, I-3, I-4, I-5, I-136, I-6, I-137, I-392, and I-53 had a controlling index of 5, which was similar in effectiveness to the compound (1) commercially available under the name of Metconazole.

Test Example 7

Damage to Wheat (Growth Inhibition) by Seed Treatment

Damage to wheat (growth inhibition) was examined in a pot test. Each of the compounds I-132, I-2, I-148, I-133, I-134, I-3, I-5, I-136, I-6, I-137, I-392, and a comparative compound (1) was weighed in an amount of 2 mg and dissolved in DMSO (18 µl). The solution thus prepared was applied to wheat seeds 1 g in a vial and 8 seeds were seeded in a 80 cm² pot. The seeds were grown in green house, as water was supplied from below, and the damage (growth inhibition) was determined and the damage index (growth inhibition) calculated 14 to 28 days after seeding.

The damage index (growth inhibition) was determined according to the criteria shown in the Table below. When the growth inhibition index is larger, the damage by growth inhibition of chemical treatment is smaller.

TABLE 19

| Growth (compared to non-treated region) | Damage index (growth inhibition) |
| --- | --- |
| 80% or more | 0 |
| 60% or more and less than 80% | 1 |
| 40% or more and less than 60% | 2 |
| 20% or more and less than 40% | 3 |
| 1% or more and less than 20% | 4 |
| No growth inhibition | 5 |

As a result, all of the inventive compounds gave damage (growth inhibition) less severe than the known compound (1) commercially available under the name of Metconazole.

The controlling activity to wheat powdery mildew and the damage (growth inhibition) by seed treatment are summarized in the following Table.

TABLE 20

| Compound number | Controlling index Wheat powdery mildew | Damage index Growth inhibition |
| --- | --- | --- |
| I-132 | 5 | 5 |
| I-2 | 5 | 1 |
| I-148 | 5 | 5 |
| I-133 | 5 | 4 |
| I-134 | 5 | 3 |
| I-3 | 5 | 1 |
| I-5 | 5 | 1 |
| I-136 | 5 | 4 |
| I-6 | 5 | 3 |
| I-137 | 5 | 5 |
| I-392 | 5 | 3 |

TABLE 20-continued

| Compound number | Controlling index Wheat powdery mildew | Damage index Growth inhibition |
| --- | --- | --- |
| I-53 | 5 | 1 |
| Compound (1) | 5 | 0 |

INDUSTRIAL APPLICABILITY

The azole derivative according to the present invention can be used favorably as an active ingredient in fungicides and plant growth-regulating agents for agriculture and horticulture and also as an active ingredient in industrial material-protecting agents.

The invention claimed is:

1. An intermediate compound of Formula (XI)

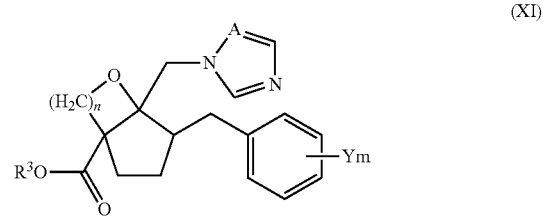

(XI)

wherein Y represents a halogen atom, a $C_1$-$C_4$-alkyl group, a $C_1$-$C_4$-haloalkyl group, a $C_1$-$C_4$-alkoxy group, a $C_1$-$C_4$-haloalkoxy group, a phenyl group, a cyano group, or a nitro group;
m is 0 to 5;
n is 1 to 6; and
A represents a nitrogen atom or a methine group;
$R^3$ represents a hydrogen atom, a $C_1$-$C_6$-alkyl group, a $C_2$-$C_6$-alkenyl group, or a $C_2$-$C_6$-alkynyl group
wherein the intermediate compound is used for the production of an azole derivative represented by the following General Formula (I):

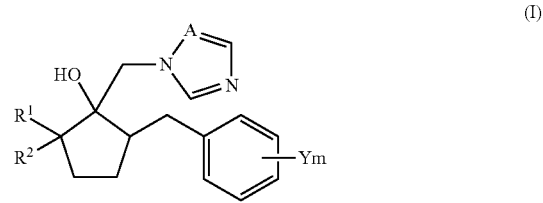

(I)

wherein $R^1$ represents a halogen atom-substituted $C_1$-$C_6$-alkyl group;
$R^2$ represents $COOR^3$, wherein the carbon atom in the carbonyl group is bound to the carbon atom in the cyclopentane ring substituted with $R^1$;
$R^3$ and $R^4$ each represent a hydrogen atom, a $C_1$-$C_6$-alkyl group, a $C_2$-$C_6$-alkenyl group, or a $C_2$-$C_6$-alkynyl group; and Y, m, and A are as defined above.

* * * * *